United States Patent
Lee et al.

(10) Patent No.: US 10,672,990 B2
(45) Date of Patent: Jun. 2, 2020

(54) COMPOUND FOR ORGANIC OPTOELECTRONIC DEVICE, COMPOSITION FOR ORGANIC OPTOELECTRONIC DEVICE AND ORGANIC OPTOELECTRONIC DEVICE AND DISPLAY DEVICE

(71) Applicants: SAMSUNG SDI CO., LTD., Yongin-si (KR); SAMSUNG ELECTRONICS CO., LTD., Suwon-si, Gyeonggi-do (KR)

(72) Inventors: Hanill Lee, Suwon-si (KR); Jun Seok Kim, Suwon-si (KR); Eun Sun Yu, Suwon-si (KR); Kipo Jang, Suwon-si (KR); Sung-Hyun Jung, Suwon-si (KR); Sujin Han, Suwon-si (KR)

(73) Assignees: SAMSUNG SDI CO., LTD., Yongin-si, Gyeonggi-do (KR); SAMSUNG ELECTRONICS CO., LTD., Suwon-si, Gyeonggi-do (KR)

( * ) Notice: Subject to any disclaimer, the term of this patent is extended or adjusted under 35 U.S.C. 154(b) by 322 days.

(21) Appl. No.: 15/475,222

(22) Filed: Mar. 31, 2017

(65) Prior Publication Data
US 2017/0373255 A1 Dec. 28, 2017

(30) Foreign Application Priority Data
Jun. 23, 2016 (KR) .................. 10-2016-0078890

(51) Int. Cl.
*H01L 51/00* (2006.01)
*C07D 251/24* (2006.01)
(Continued)

(52) U.S. Cl.
CPC ........ *H01L 51/0067* (2013.01); *C07D 251/24* (2013.01); *C07D 401/10* (2013.01); *C09K 11/025* (2013.01); *H01L 51/0054* (2013.01); *H01L 51/0058* (2013.01); *H01L 51/0072* (2013.01); *H01L 51/0085* (2013.01); *H01L 51/5016* (2013.01); *H01L 51/5024* (2013.01);
(Continued)

(58) Field of Classification Search
None
See application file for complete search history.

(56) References Cited

U.S. PATENT DOCUMENTS

| 2011/0121274 A1 | 5/2011 | Parham et al. |
| 2012/0211736 A1* | 8/2012 | Kim ............ C09K 11/06 257/40 |
| 2016/0028021 A1 | 1/2016 | Zeng et al. |

FOREIGN PATENT DOCUMENTS

| CN | 102597158 A | 7/2012 |
| CN | 107922359 A | 4/2018 |

(Continued)

OTHER PUBLICATIONS

Chinese Office Action dated Sep. 25, 2019 and the Search Report dated Sep. 18, 2019 for corresponding Chinese Patent Application No. 201710230858.0.

*Primary Examiner* — Jay Yang
(74) *Attorney, Agent, or Firm* — Lee IP Law, P.C.

(57) ABSTRACT

Disclosed are a compound for an organic optoelectronic device represented by Chemical Formula 1, a composition for an organic optoelectronic device, an organic optoelectronic device including the same, and a display device. Details of Chemical Formula 1 are the same as defined in the specification.

9 Claims, 1 Drawing Sheet

(51) Int. Cl.
*C07D 401/10* (2006.01)
*C09K 11/02* (2006.01)
*H01L 51/50* (2006.01)

(52) U.S. Cl.
CPC .. *H01L 51/5072* (2013.01); *H01L 2251/5384* (2013.01)

(56) References Cited

FOREIGN PATENT DOCUMENTS

| | | |
|---|---|---|
| KR | 10-2012-0116282 A | 10/2012 |
| KR | 10-2012-0140603 A | 12/2012 |
| KR | 10-2014-0135524 A | 11/2014 |
| KR | 10-1542714 B | 8/2015 |
| KR | 10-2015-0115648 A | 10/2015 |
| KR | 10-2015-0120875 A | 10/2015 |
| KR | 10-2016-0011036 A | 1/2016 |
| WO | WO 2012-033061 A1 | 3/2012 |
| WO | WO-2017/016630 A1 * | 2/2017 |

* cited by examiner

[FIG. 1]
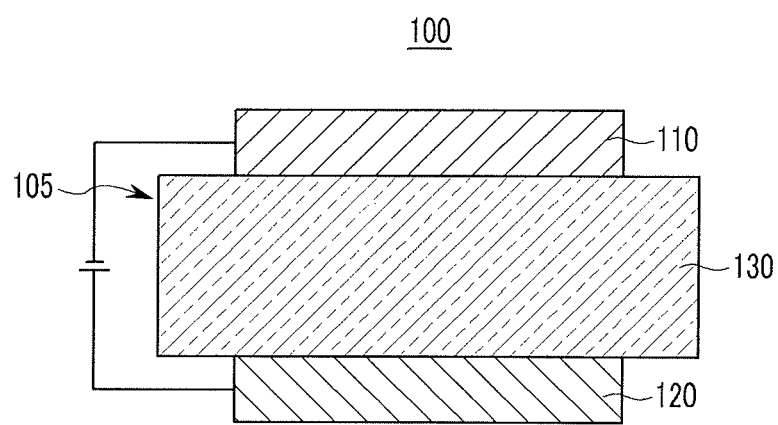
[FIG. 2]
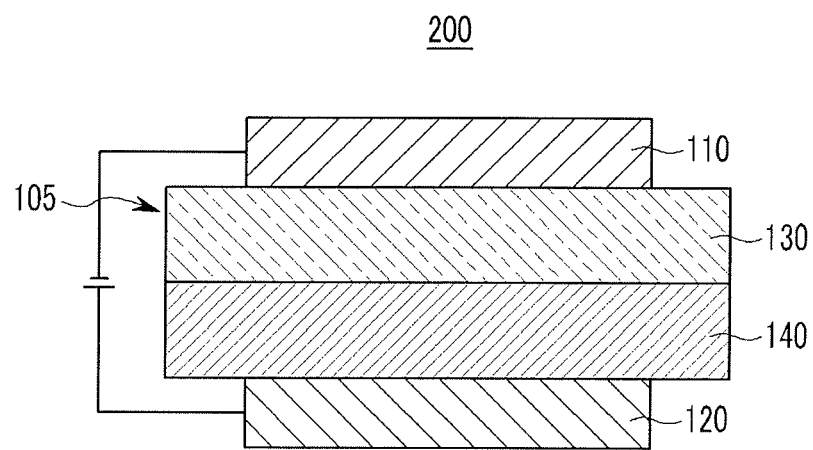

COMPOUND FOR ORGANIC OPTOELECTRONIC DEVICE, COMPOSITION FOR ORGANIC OPTOELECTRONIC DEVICE AND ORGANIC OPTOELECTRONIC DEVICE AND DISPLAY DEVICE

CROSS-REFERENCE TO RELATED APPLICATION

This application claims priority to and the benefit of Korean Patent Application No. 10-2016-0078890 filed in the Korean Intellectual Property Office on Jun. 23, 2016, the entire contents of which are incorporated herein by reference.

BACKGROUND OF THE INVENTION

1. Field

A compound for an organic optoelectronic device, a composition for an organic optoelectronic device, an organic optoelectronic device, and a display device are disclosed.

2. Description of the Related Art

An organic optoelectronic device (organic optoelectronic diode) is a device that converts electrical energy into photoenergy, and vice versa An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of an organic optoelectronic device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include a light-emitting layer and optionally an auxiliary layer, and the auxiliary layer may be, for example at least one selected from a hole injection layer, a hole transport layer, an electron blocking layer, an electron transport layer, an electron injection layer, and a hole blocking layer for improving efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

SUMMARY OF THE INVENTION

An embodiment provides a compound for an organic optoelectronic device capable of realizing an organic optoelectronic device having high efficiency and a long life-span.

Another embodiment provides a composition for an organic optoelectronic device including the compound for an organic optoelectronic device.

Yet another embodiment provides an organic optoelectronic device including the compound.

Still another embodiment provides a display device including the organic optoelectronic device.

According to an embodiment, a compound for an organic optoelectronic device represented by Chemical Formula 1 is provided.

[Chemical Formula 1]

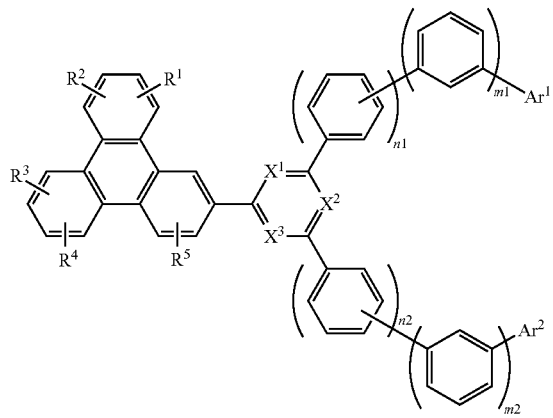

In Chemical Formula 1, $X^1$ to $X^3$ are independently N or $CR^a$, at least one of $X^1$ to $X^3$ is N, $R^a$, and $R^1$ to $R^5$ are independently hydrogen, deuterium, a substituted or unsubstituted C1 to C10 alkyl group, or a substituted or unsubstituted C6 to C12 aryl group, $Ar^1$ and $Ar^2$ are independently hydrogen, deuterium, a substituted or unsubstituted C6 to C30 aryl group, a substituted or unsubstituted C2 to C30 heterocyclic group, or a combination thereof, at least one of $Ar^1$ and $Ar^2$ is a substituted or unsubstituted fluorenyl group, n1, n2, m1, and m2 are independently an integer of 0 to 2, $1 \leq m1+m2 \leq 4$, and the "substituted" refers to replacement of at least one hydrogen by deuterium, a C1 to C4 alkyl group, a C6 to C18 aryl group, or a C2 to C18 heteroaryl group.

According to another embodiment, a composition for an organic optoelectronic device includes a first compound for an organic optoelectronic device described above; and a second compound for an organic optoelectronic device represented by Chemical Formula 2.

[Chemical Formula 2]

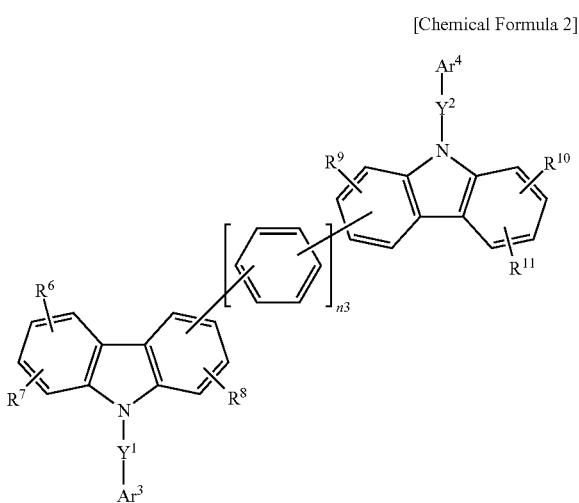

In Chemical Formula 2, $Y^1$ and $Y^2$ are independently a single bond, a substituted or unsubstituted C6 to C30 arylene group, a substituted or unsubstituted C2 to C30 heteroarylene group, or a combination thereof, $Ar^3$ and $Ar^4$ are independently a substituted or unsubstituted C6 to C30 aryl group, a substituted or unsubstituted C2 to C30 heterocyclic group, or a combination thereof, $R^6$ to $R^{11}$ are independently hydrogen, deuterium, a substituted or unsubstituted C1 to C20 alkyl group, a substituted or unsubstituted C6 to C30 aryl group, a substituted or unsubstituted C2 to C50 heterocyclic group, or a combination thereof, n3 is an integer of 0 to 2; and the "substituted" refers to replacement of at least one hydrogen by deuterium, C1 to C4 alkyl group, C6 to C18 aryl group, or C2 to C18 heteroaryl group.

According to another embodiment, an organic optoelectronic device includes an anode and a cathode facing each other and at least one organic layer disposed between the anode and the cathode, wherein the organic layer includes the compound for an organic optoelectronic device, or the composition for an organic optoelectronic device.

According to yet another embodiment, a display device including the organic optoelectronic device is provided.

An organic optoelectronic device having high efficiency and a long life-span may be realized.

BRIEF DESCRIPTION OF THE DRAWINGS

FIGS. 1 and 2 are cross-sectional views showing organic light emitting diodes according to embodiments.

DETAILED DESCRIPTION

Hereinafter, embodiments of the present invention are described in detail. However, these embodiments are exemplary, the present invention is not limited thereto and the present invention is defined by the scope of claims.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example of the present invention, "substituted" refers to replacement of at least one hydrogen of a substituent or a compound by deuterium, C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In one specific example of the present invention, "substituted" "substituted" refers to replacement of at least one hydrogen of a substituent or a compound by deuterium, a C1 to C30 alkyl group, a C6 to C18 aryl group, or a C2 to C20 heteroaryl group. In one more specific example of the present invention, "substituted" "substituted" refers to replacement of at least one hydrogen of a substituent or a compound by deuterium, a C1 to C4 alkyl group, a C6 to C18 aryl group, or a C2 to C18 heteroaryl group.

As used herein, when a definition is not otherwise provided, "hetero" refers to one including one to three heteroatoms selected from N, O, S, P, and Si, and remaining carbons in one functional group.

As used herein, when a definition is not otherwise provided, "an alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

As used herein, an "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one heteroatom selected from N, O, S, P, and Si instead of carbon (C) in a cyclic compound such as aryl group, a cycloalkyl group, a fused ring thereof, or a combination thereof. When the heterocyclic group is a fused ring, the entire ring or each ring of the heterocyclic group may include one or more heteroatoms.

For example, a "heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused.

When the heteroaryl group is a fused ring, each ring may include one to three heteroatoms.

Specific examples of the heteroaryl group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted isoquinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

In the present specification, hole characteristics refer to an ability to donate an electron to form a hole when an electric field is applied, and that a hole formed in the anode may be easily injected into a light-emitting layer, and a hole formed in a light-emitting layer may be easily transported into an anode and transported in a light-emitting layer due to conductive characteristics according to a highest occupied molecular orbital (HOMO) level.

In addition, electron characteristics refer to an ability to accept an electron when an electric field is applied and that an electron formed in a cathode may be easily injected into a light-emitting layer, and an electron formed in a light-emitting layer may be easily transported into a cathode and transported in a light-emitting layer due to conductive characteristics according to a lowest unoccupied molecular orbital (LUMO) level.

Hereinafter, a compound for an organic optoelectronic device according to an embodiment is described.

A compound for an organic optoelectronic device according to an embodiment is represented by Chemical Formula 1.

[Chemical Formula 1]

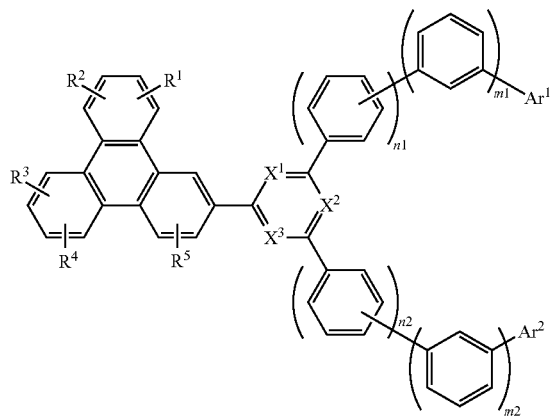

In Chemical Formula 1, $X^1$ to $X^3$ are independently N or $CR^a$, at least two of $X^1$ to $X^3$ are N, $R^a$ and $R^1$ to $R^5$ are independently hydrogen, deuterium, a substituted or unsubstituted C1 to C10 alkyl group, or a substituted or unsubstituted C6 to C12 aryl group, $Ar^1$ and $Ar^2$ are independently hydrogen, deuterium, a substituted or unsubstituted C6 to C30 aryl group, a substituted or unsubstituted C2 to C30 heterocyclic group, or a combination thereof, at least one of $Ar^1$ and $Ar^2$ is a substituted or unsubstituted fluorenyl group, n1, n2, m1, and m2 are independently an integer of 0 to 2, 1≤m1+m2≤4, and the "substituted" refers to replacement of at least one hydrogen by deuterium, a C1 to C4 alkyl group, a C6 to C18 aryl group, or a C2 to C18 heteroaryl group. In one example of the present invention, the "substituted" refers to replacement of at least one hydrogen by deuterium, a methyl group, an ethyl group, a n-propyl group, an iso-propyl group, a phenyl group, a meta-biphenyl group, a para-biphenyl group, a pyridinyl group, a pyrimidinyl group, a triazinyl group, a quinolinyl group, an isoquinolinyl group, a quinazolinyl group, or an isoquinazolinyl group. For example, the "substituted" refers to replacement of at least one hydrogen by deuterium, methyl group, ethyl group, phenyl group, meta-biphenyl group, para-biphenyl group, pyridinyl group, pyrimidinyl group, or triazinyl group.

The compound for an organic optoelectronic device according to the present invention includes pyrimidine or triazine directly linked with triphenylene and thus may make a LUMO electron cloud be expanded to the triphenylene, have low LUMO energy, and thus realize a low driving voltage.

In addition, the compound includes at least one meta-bound phenylene and thus may lower a deposition temperature and improve process stability.

Furthermore, the compound includes a fluorenyl group that is a fused substituent, and thus may prevent a sharp decrease of the deposition temperature. In addition, the compound may not be easily crystallized due to a fluorene group having high Tg and thus more stabilize a device.

In other words, the compound has a polar group and thus may make the LUMO electron cloud of pyrimidine or triazine capable of interacting with an electrode be expanded to the triphenylene and thus improve charge injection and transport characteristics and lower a driving voltage.

In addition, the meta-bound phenylene structure of the compound may suppress an interaction among molecules and thus prevent crystallization, and the compound includes a fluorenyl group and thus may lower a deposition temperature and thus realize a manufacture yield and a life-span of a device.

In an example embodiment of the present invention, $R^1$ to $R^5$ may independently be hydrogen, or a substituted or unsubstituted C6 to C12 aryl group, and may be for example hydrogen, a substituted or unsubstituted phenyl group, or a substituted or unsubstituted biphenyl group.

In an example embodiment of the present invention, $R^a$ may be hydrogen, or a substituted or unsubstituted C1 to C4 alkyl group, for example hydrogen.

In an example embodiment of the present invention, $Ar^1$ and $Ar^2$ may independently be hydrogen, deuterium, a substituted or unsubstituted phenyl group, a substituted or unsubstituted biphenyl group, a substituted or unsubstituted terphenyl group, a substituted or unsubstituted fluorenyl group, a substituted or unsubstituted pyridinyl group, a substituted or unsubstituted pyrimidinyl group, a substituted or unsubstituted triazinyl group, a substituted or unsubstituted quinazolinyl group, a substituted or unsubstituted isoquinazolinyl group, or a combination thereof, and may be for example selected from hydrogen, deuterium, or a substituted or unsubstituted substituents of Group I.

[Group I]

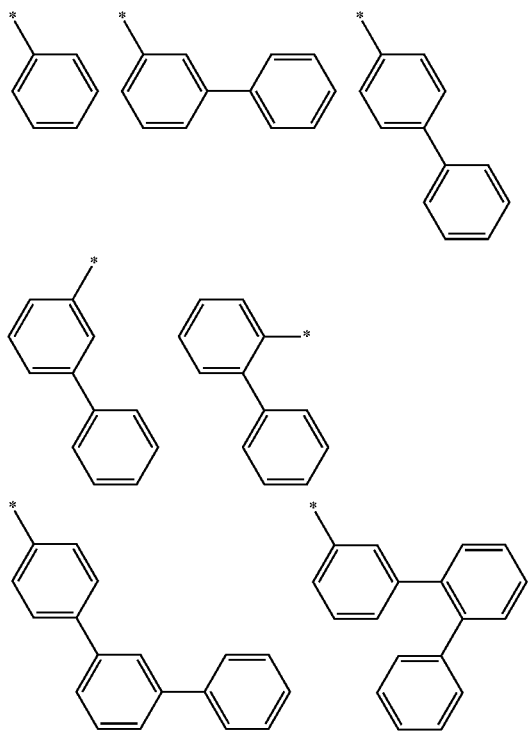

-continued

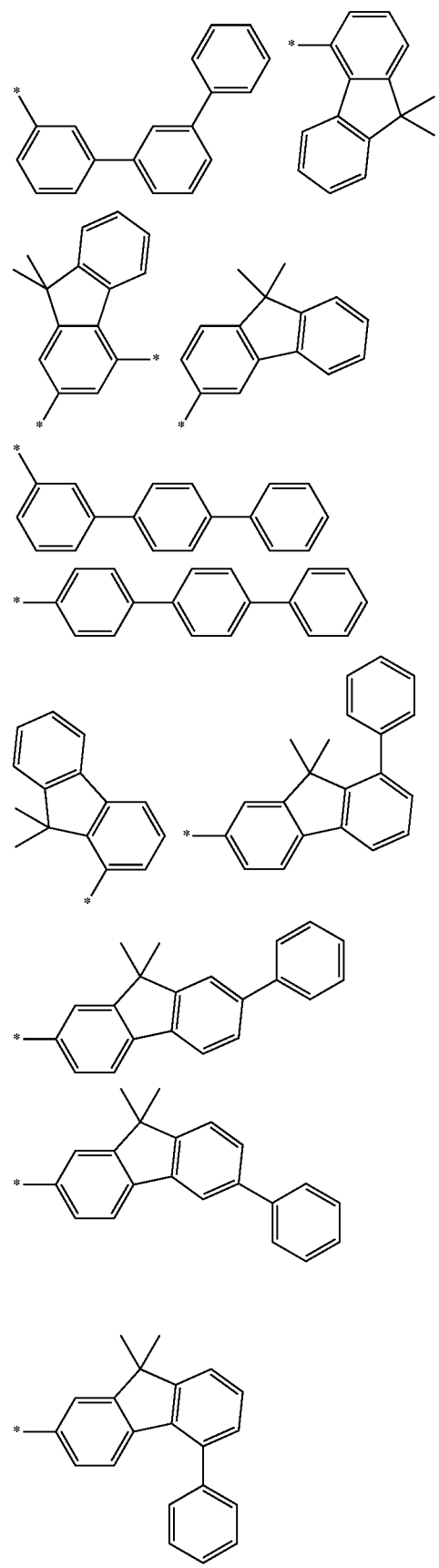

-continued

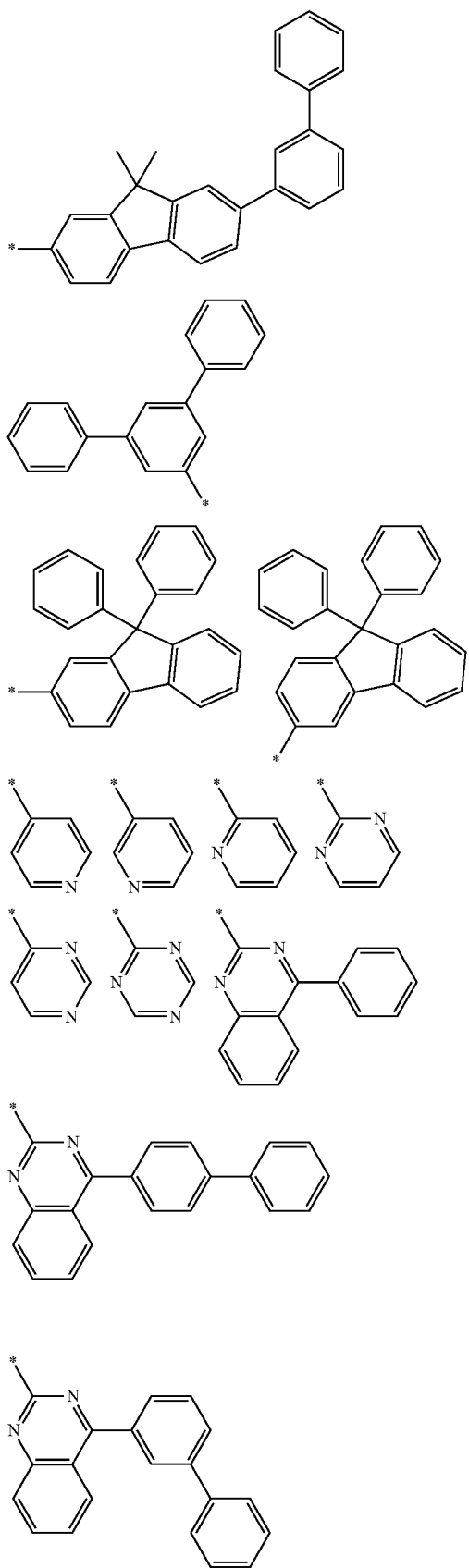
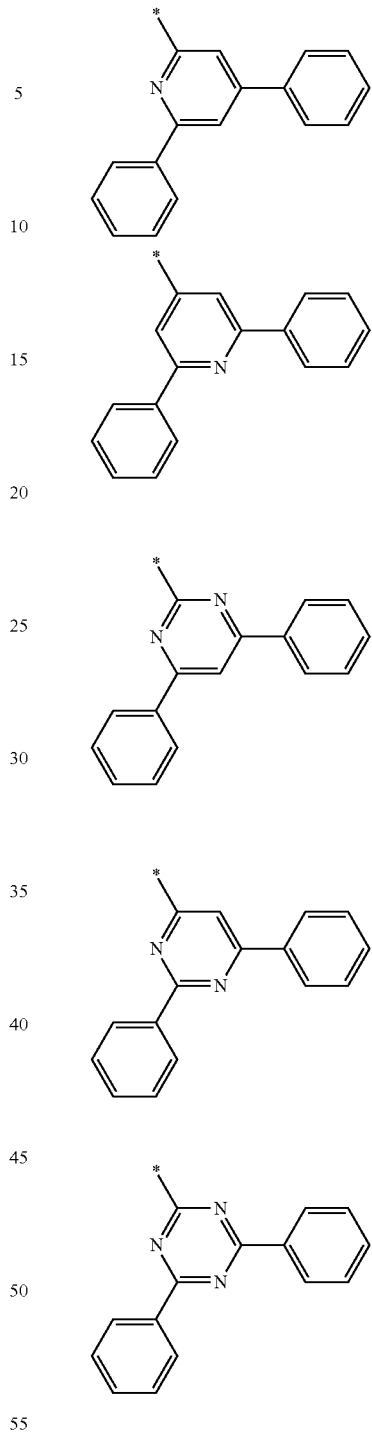

In Group I, * is a binding site with an adjacent atom.

In one example of the present invention, at least one of m1 and m2 is 1. That is, at least one meta-bound phenylene is necessarily included.

In one example of the present invention, the six membered ring including $X^1$ to $X^3$ may be pyrimidine where two of $X^1$ to $X^3$ are N or triazine where $X^1$ to $X^3$ are all N, and the compound may be for example represented by one of Chemical Formula 1-I, 1-II, and 1-III.

[Chemical Formula 1-I]

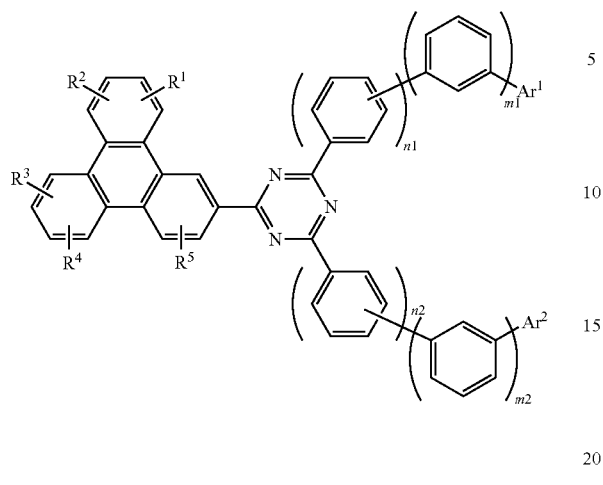

mulae 1-1 to 1-4 according to a presence of a substituent of triphenylene and a position of the substituent.

[Chemical Formula 1-1]

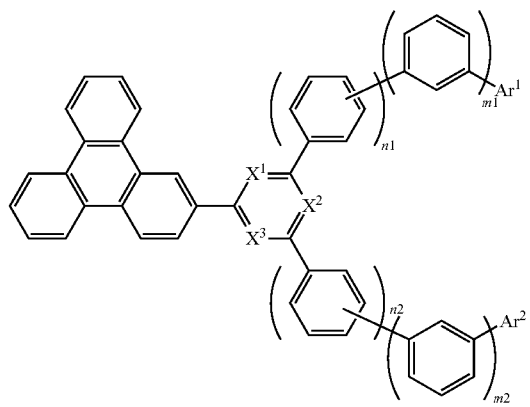

[Chemical Formula 1-II]

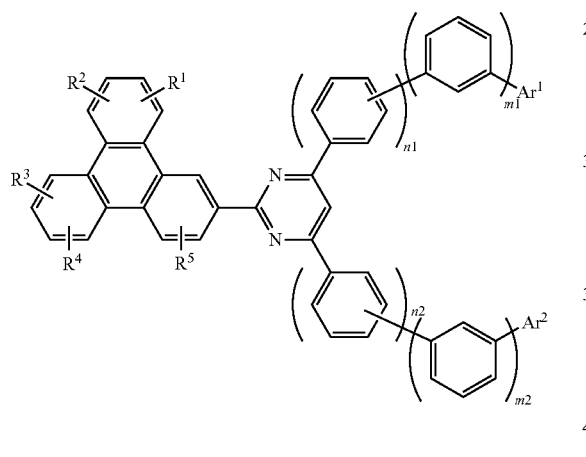

[Chemical Formula 1-2]

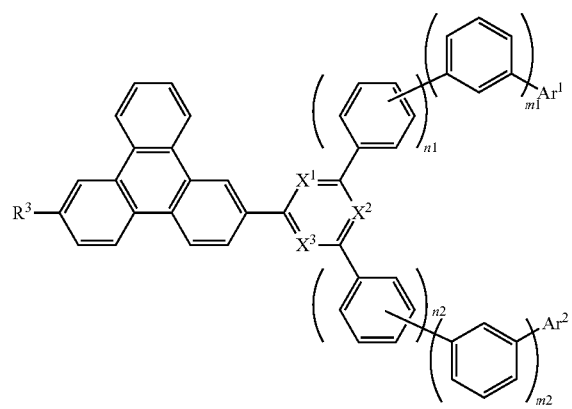

[Chemical Formula 1-III]

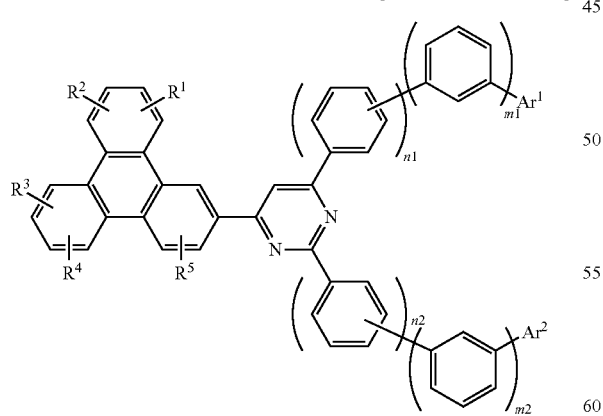

[Chemical Formula 1-3]

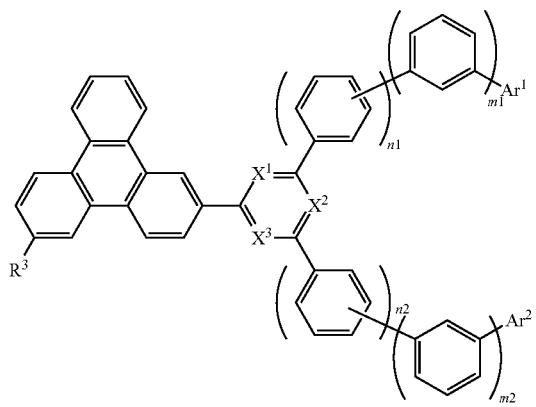

In Chemical Formulae 1-I, 1-II, and 1-III, $R^1$ to $R^5$, $Ar^1$ and $Ar^2$, n1, n2, m1, and m2 are the same as described above.

In one example of the present invention, the compound may be for example represented by one of Chemical For-

[Chemical Formula 1-4]

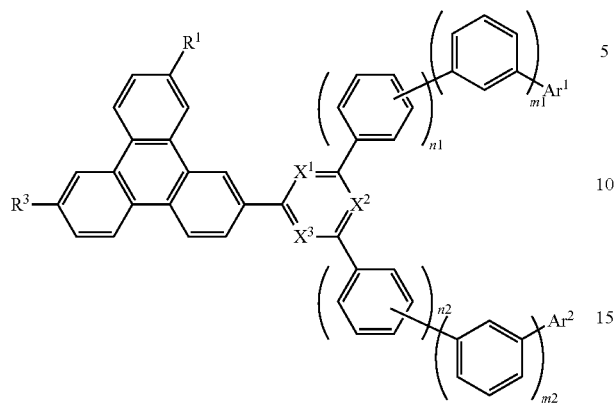

In Chemical Formulae 1-1 to 1-4, Ar¹, Ar², n1, n2, m1, m2, X¹ to X³, R¹, and R³ are the same as described above.

In addition, the compound may be for example represented by one of Chemical Formulae 1-A, 1-B, 1-C, 1-D, and 1-E according to a position of the meta-bound phenylene.

[Chemical Formula 1-A]

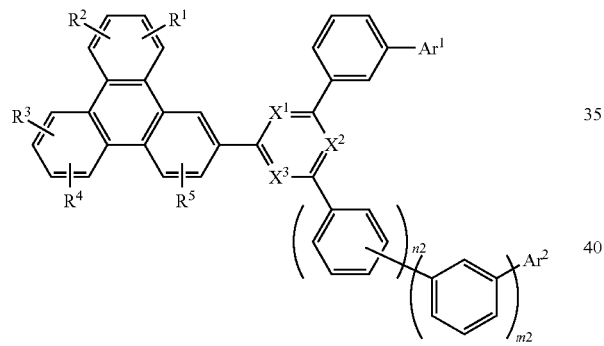

[Chemical Formula 1-B]

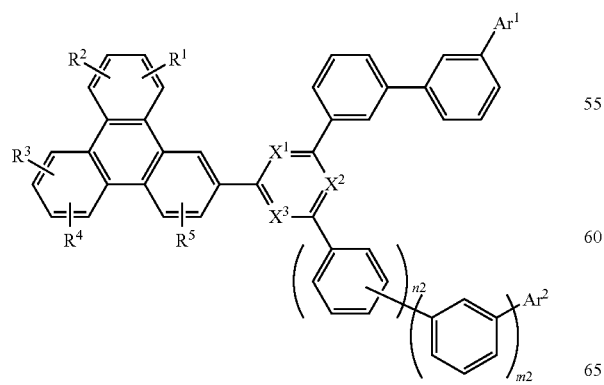

[Chemical Formula 1-C]

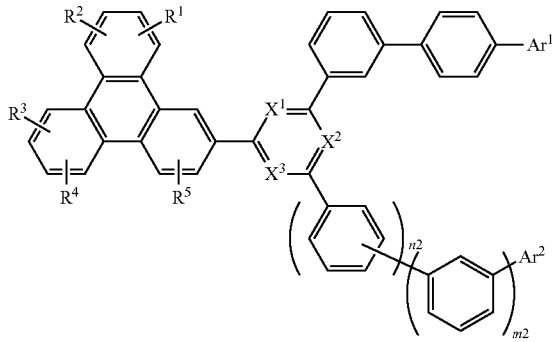

[Chemical Formula 1-D]

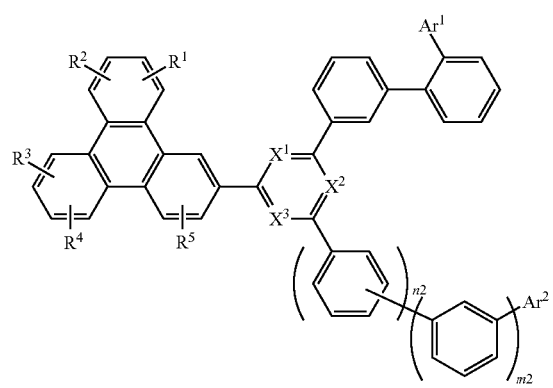

[Chemical Formula 1-E]

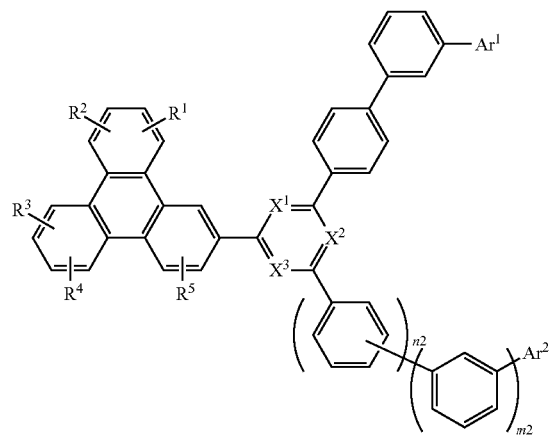

In Chemical Formulae 1-A to 1-E, Ar¹ and Ar², n2, m2, and R¹ to R⁵ are the same as described above, X¹ to X³ are independently N or CH, and at least two of X¹ to X³ are N.

In a specific example embodiment, Chemical Formula 1 may be represented by one of Chemical Formulae 1-a1 to 1-a4, 1-b1, 1-b2, 1-c1, 1-d1, and 1-e1.

[Chemical Formula 1-a1]
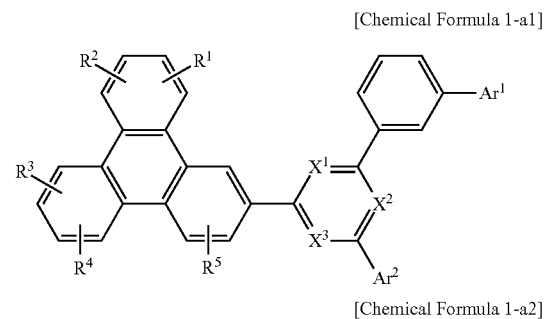

[Chemical Formula 1-a2]
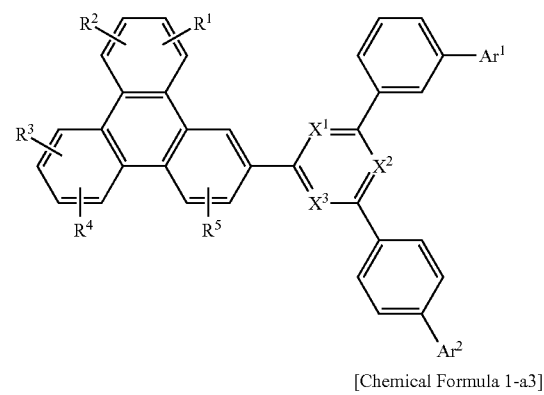

[Chemical Formula 1-a3]
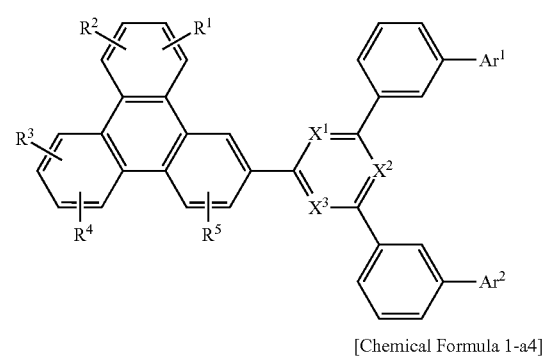

[Chemical Formula 1-a4]
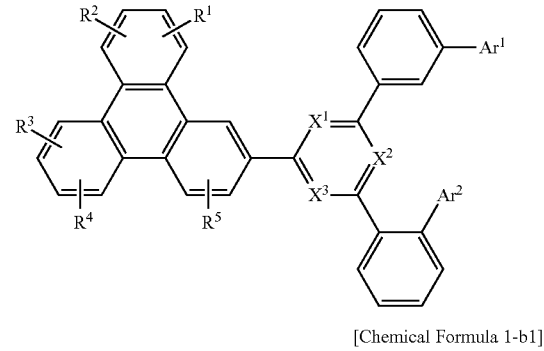

[Chemical Formula 1-b1]
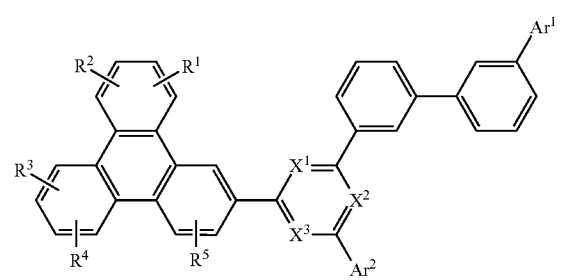

[Chemical Formula 1-b2]
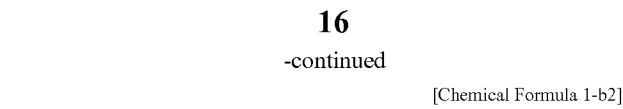

[Chemical Formula 1-c1]
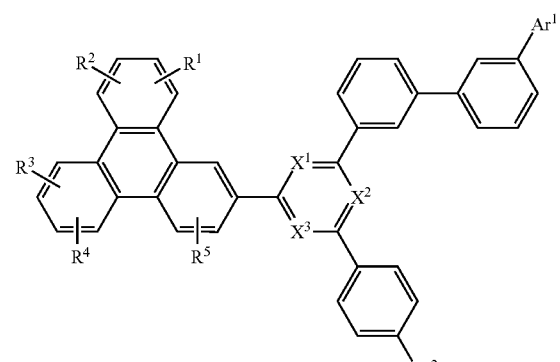

[Chemical Formula 1-d1]
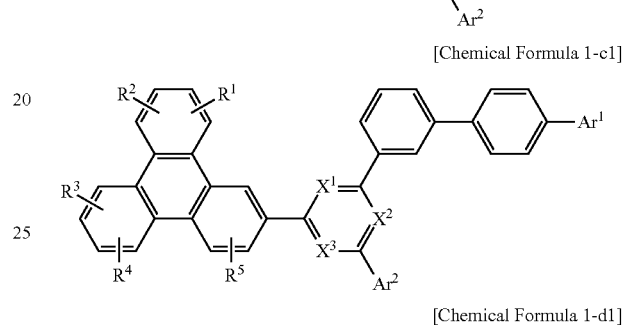

[Chemical Formula 1-e1]
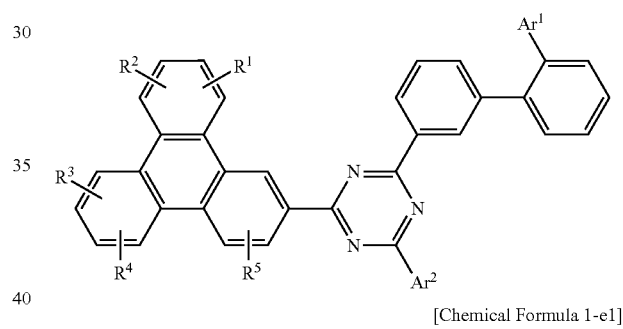

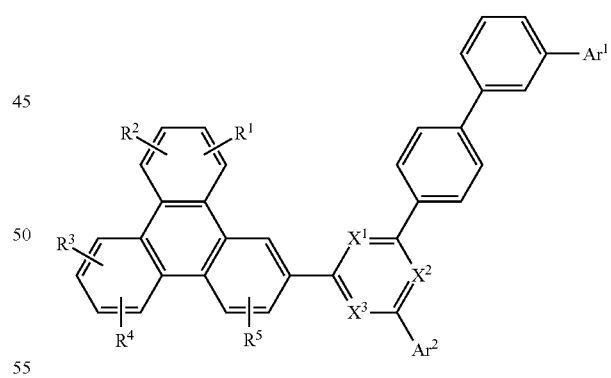

In Chemical Formulae 1-a1 to 1-e1, $Ar^1$ and $Ar^2$, $X^1$ to $X^3$ and $R^1$ to $R^5$ are the same as described above.

At least one of $Ar^1$ and $Ar^2$ may be a substituted or unsubstituted fluorenyl group. Specifically, the substituted or unsubstituted fluorenyl group may be selected from substituents of Group II.

[Group II]

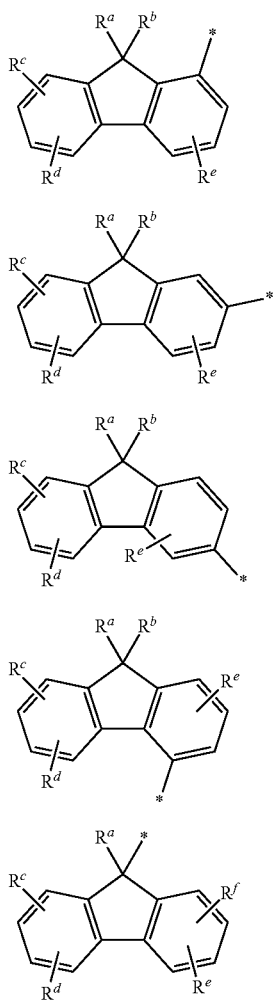

[F-1]

[F-2]

[F-3]

[F-4]

[F-5]

In Group II, $R^a$ and $R^b$ are independently, a substituted or unsubstituted C1 to C10 alkyl group, a substituted or unsubstituted C6 to C12 aryl group, $R^c$ to $R^f$ are independently hydrogen, deuterium, a substituted or unsubstituted C1 to C10 alkyl group, a substituted or unsubstituted C6 to C12 aryl group, * is a linking point with an adjacent atom, and the "substituted" refers to replacement of at least one hydrogen by deuterium, a C1 to C4 alkyl group, a C6 to C18 aryl group, or a C2 to C18 heteroaryl group. For example the "substituted" refers to replacement of at least one hydrogen by deuterium, a phenyl group, or a biphenyl group.

For example, the substituted or unsubstituted fluorenyl group may be represented by F-1, F-2, or F-3 of Group More specifically, it may be selected from substituents of Group II-1.

[Group II-1]

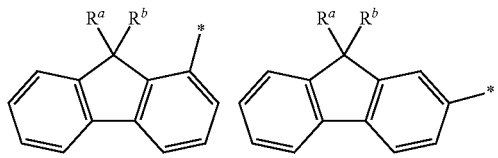

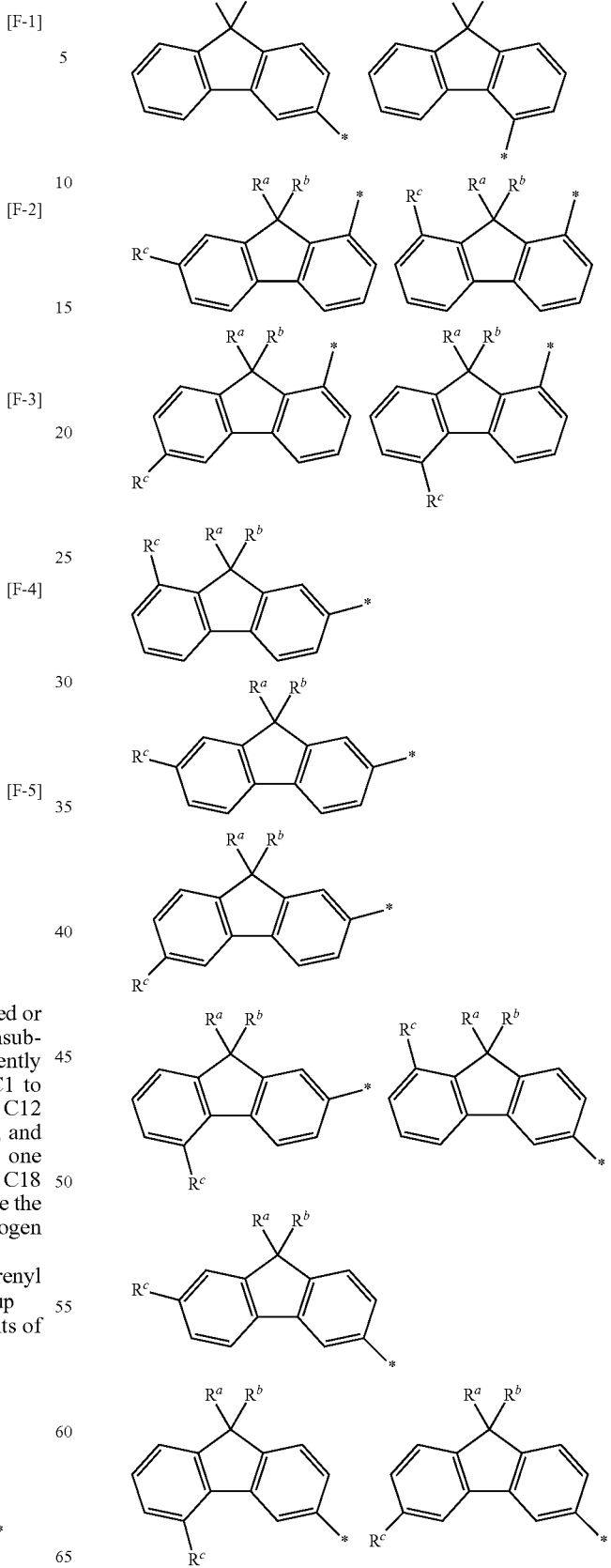

-continued

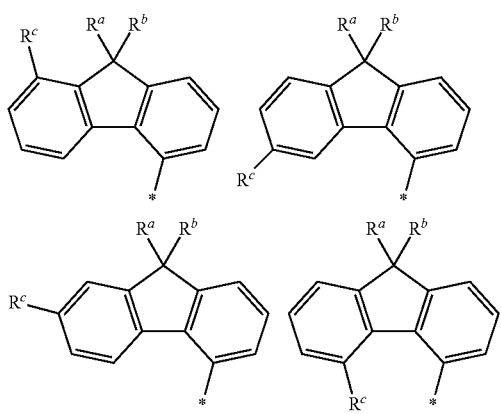

In Group II-1, $R^a$ to $R^e$ are independently a substituted or unsubstituted C1 to C10 alkyl group, a substituted or unsubstituted C6 to C12 aryl group, and * is a linking point with an adjacent atom.

In one example of the present invention, Chemical Formula 1 may be represented by Chemical Formula 1-1.

In one example of the present invention, Chemical Formula 1 may be represented by Chemical Formula 1-A, 1-B, 1-C, or 1-D, and more specifically Chemical Formula 1-A or 1-C, for example Chemical Formula 1-a1, 1-a2, or 1-c1. The compound for an organic optoelectronic device represented by Chemical Formula 1 may be for example selected from compounds of Group 1, but is not limited thereto.

[Group 1]

1

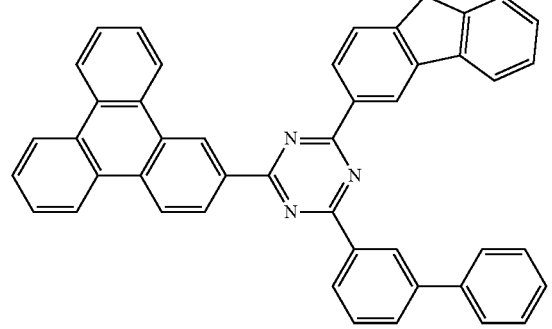

2

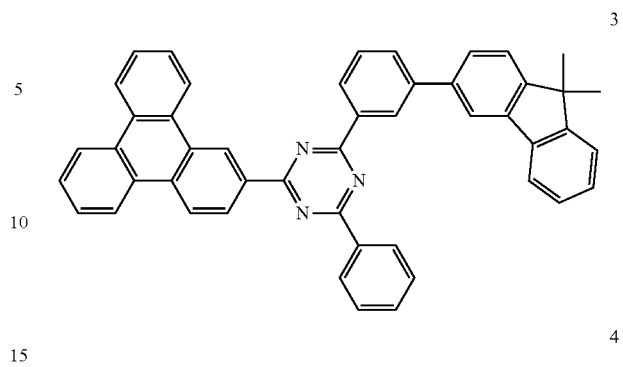

3

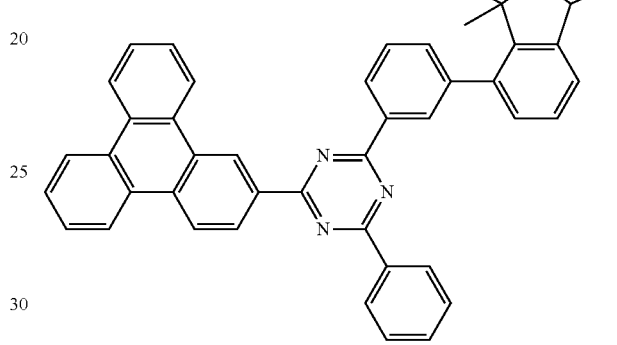

4

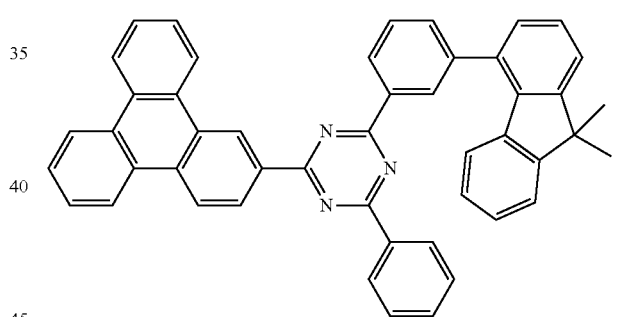

5

6

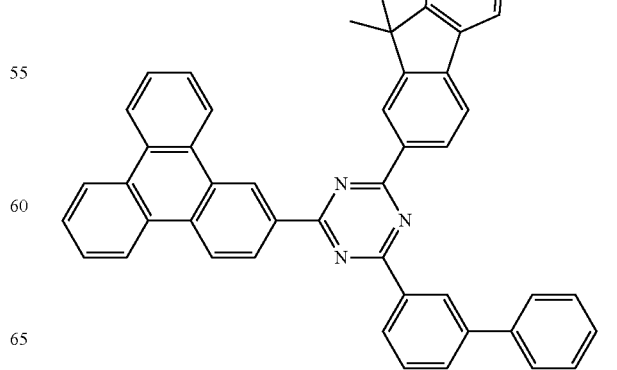

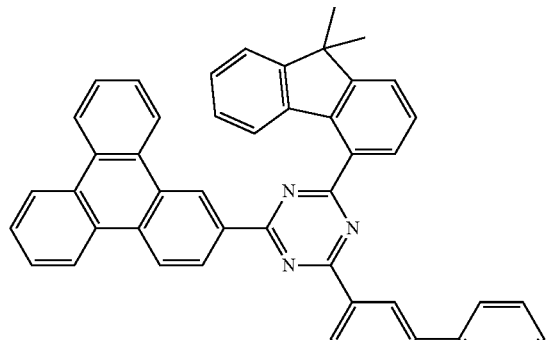
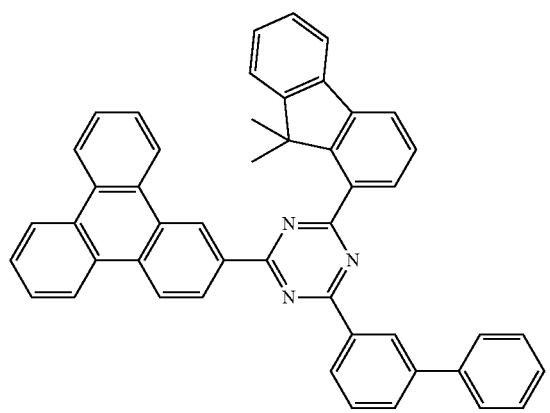
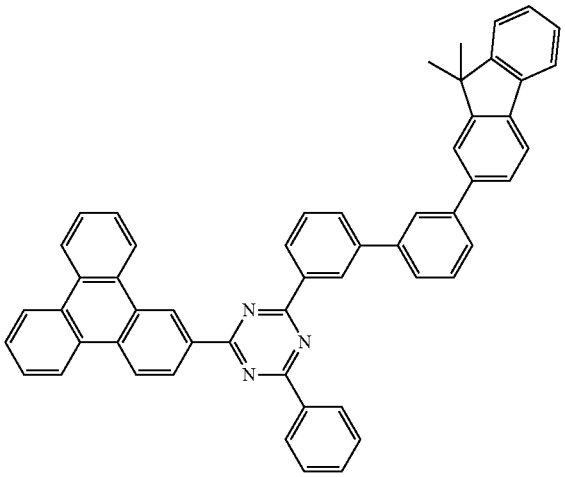
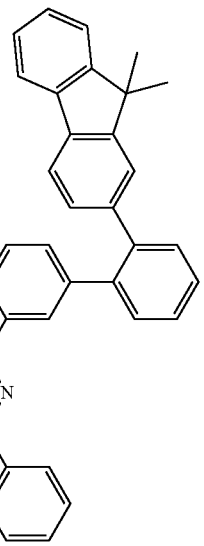
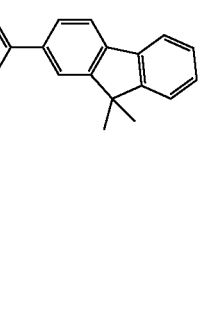
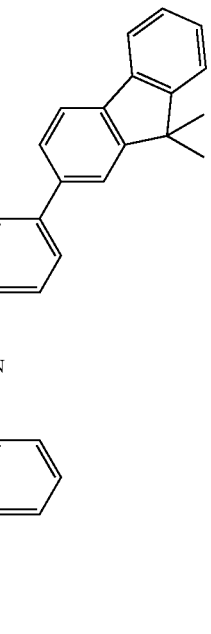

14
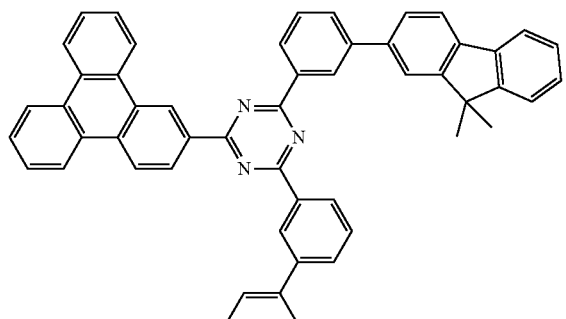
15
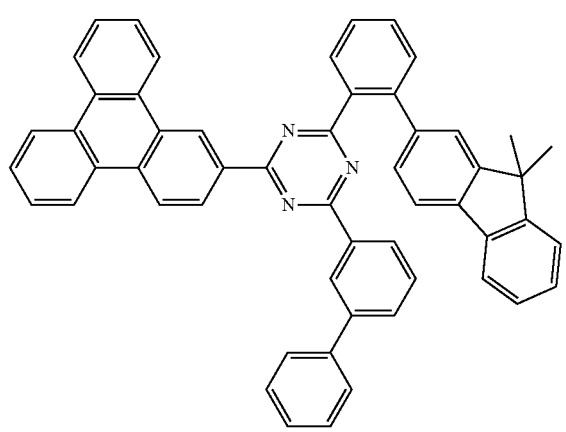
16
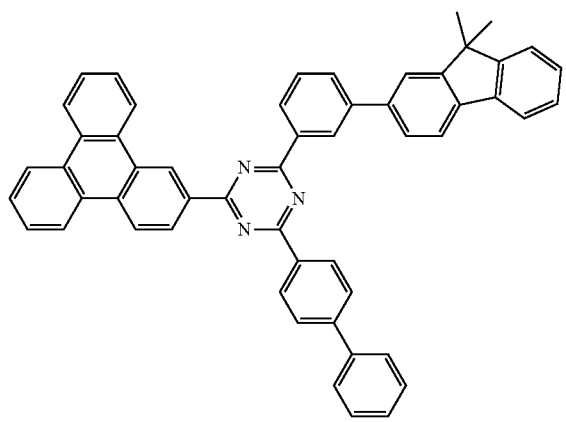
17
18
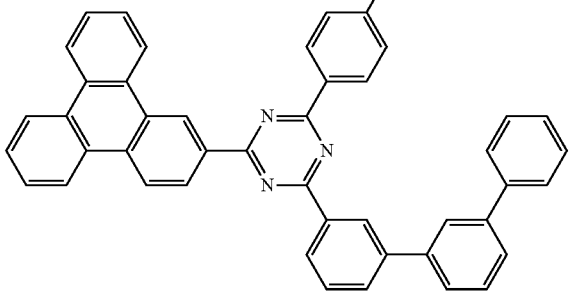
19
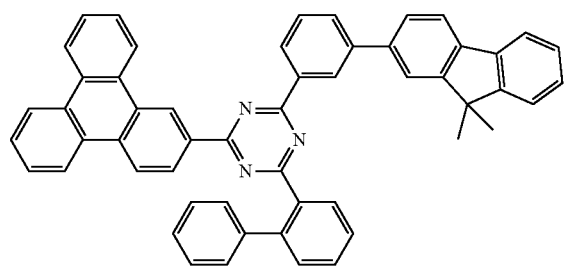
20
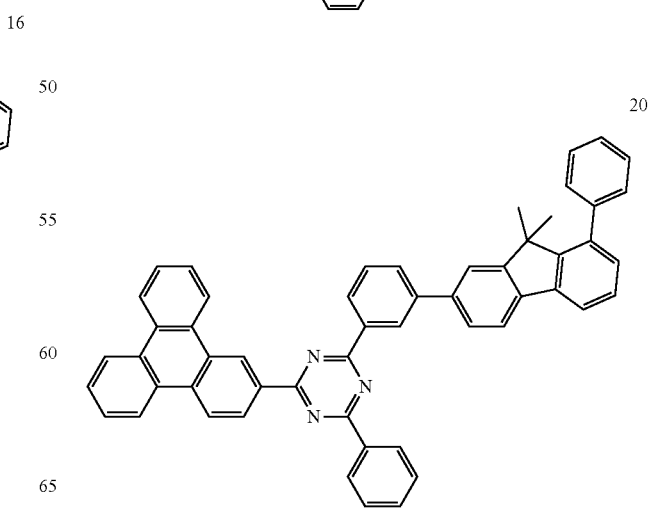

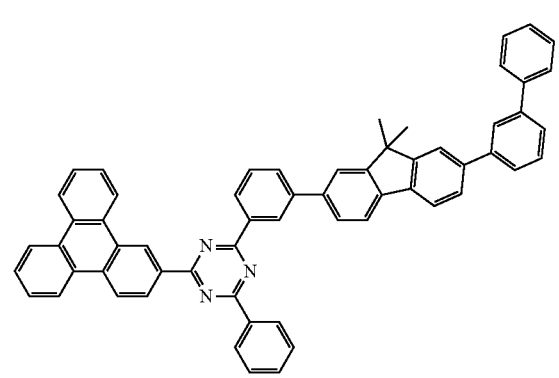
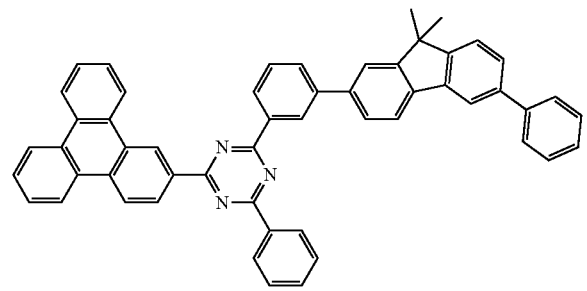
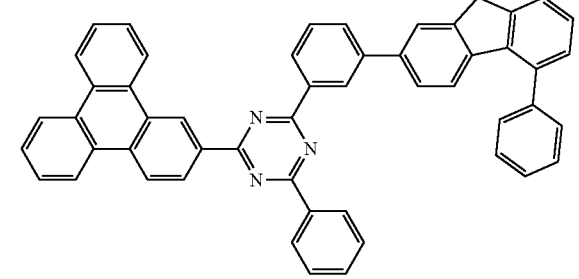
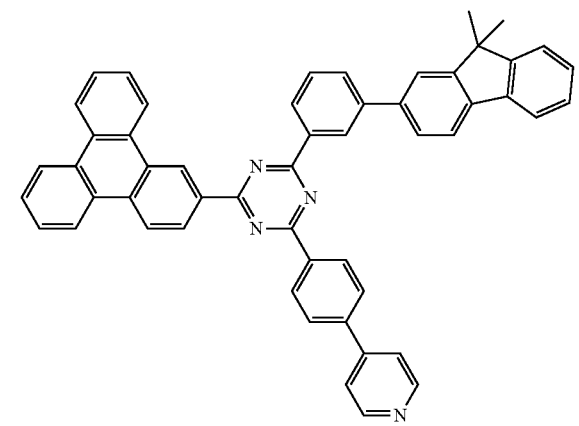
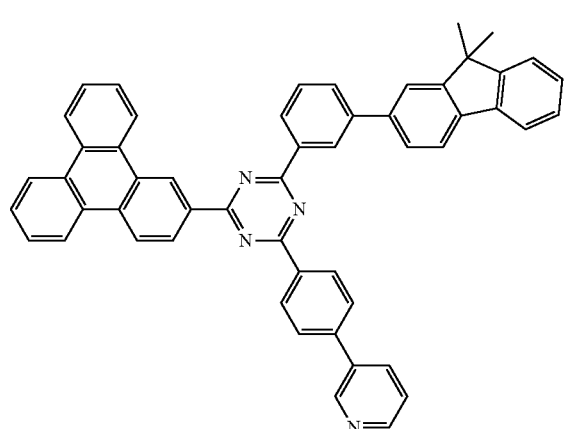
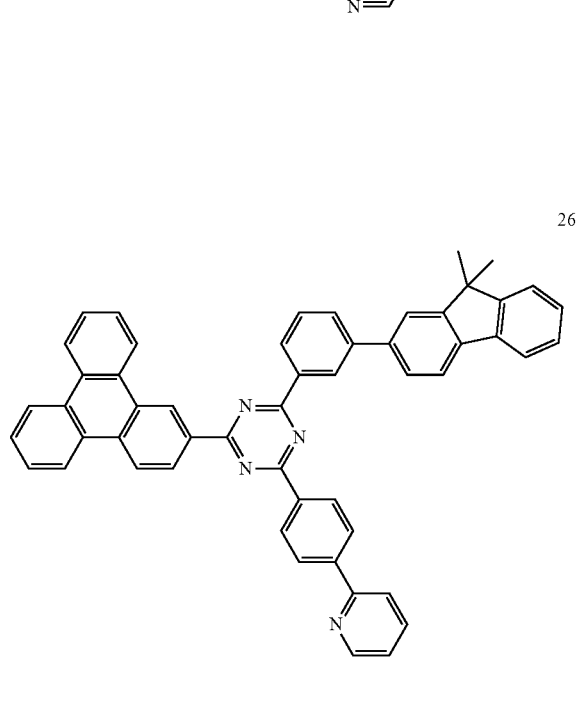
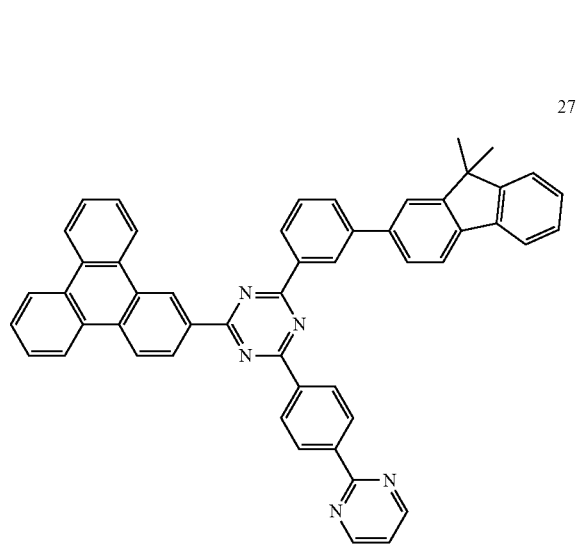

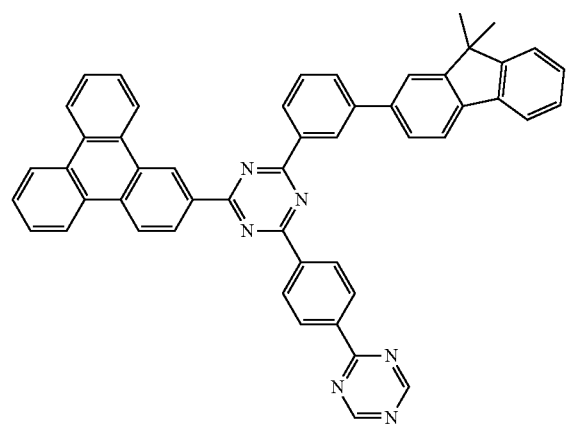
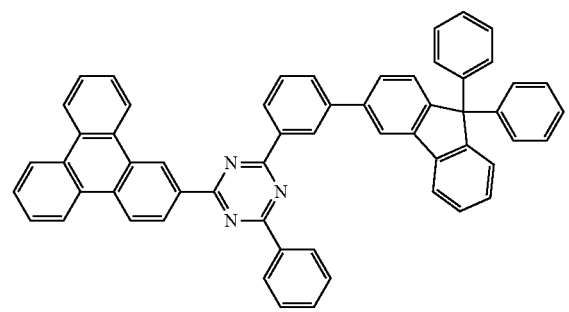
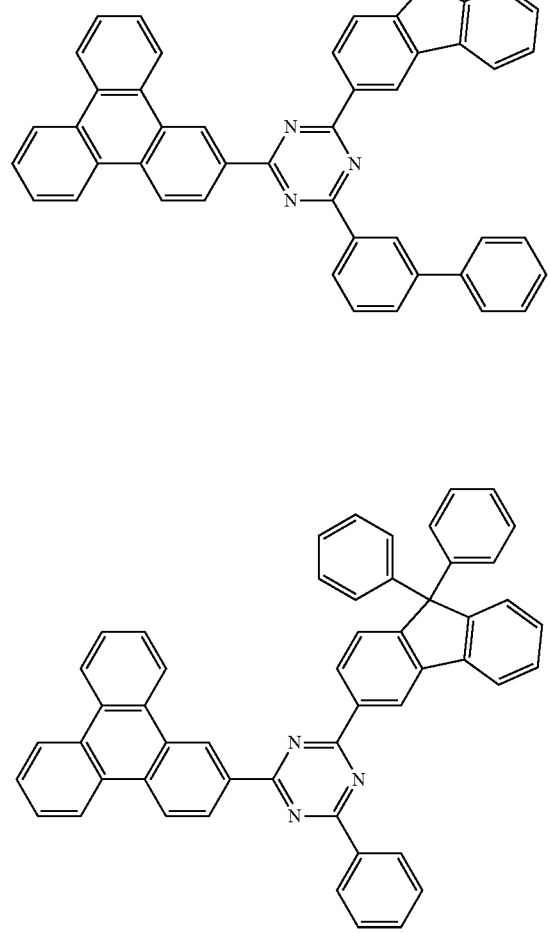
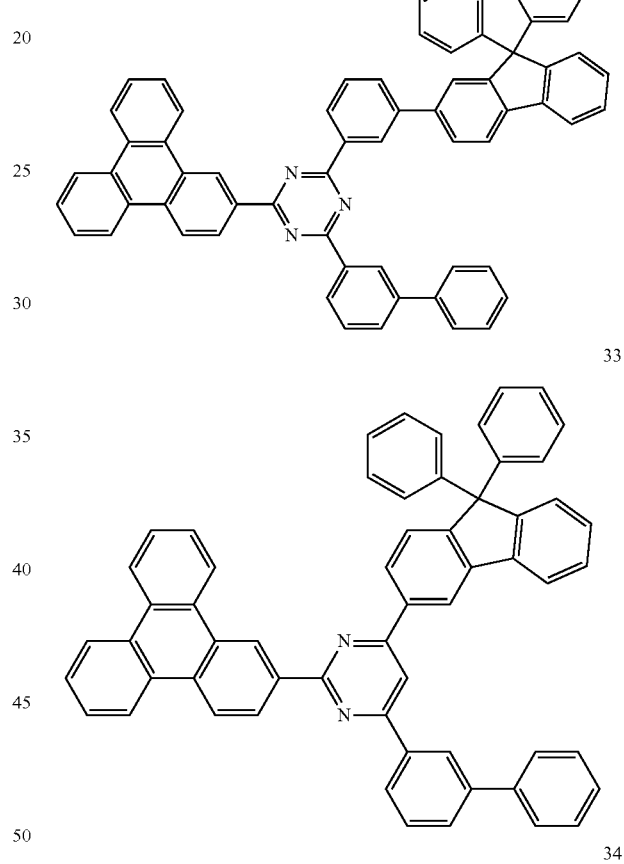

35
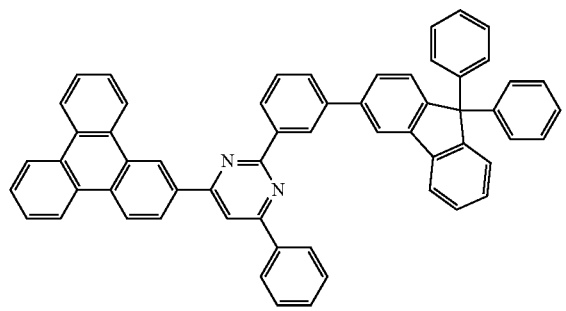
36
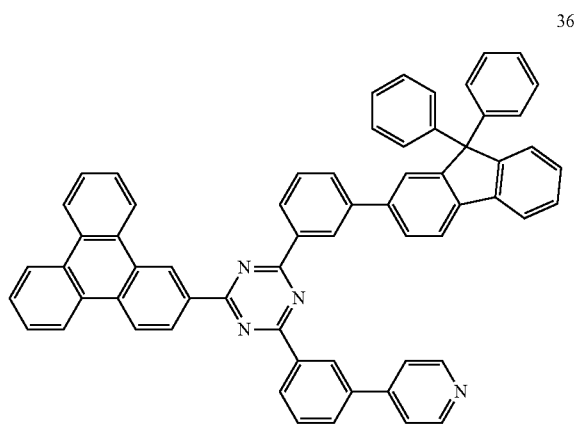
37
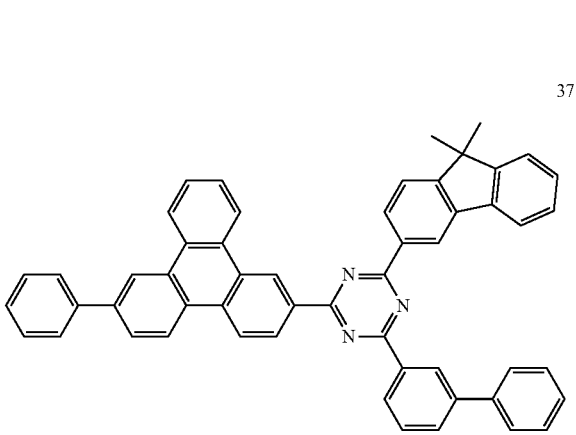
38
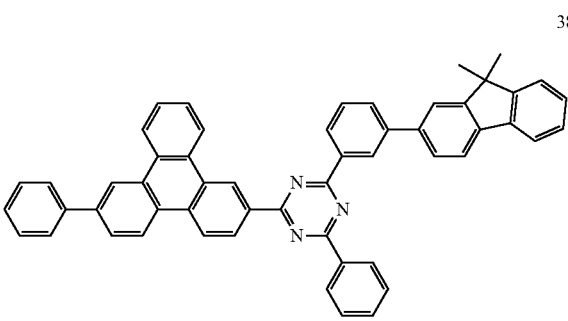
39
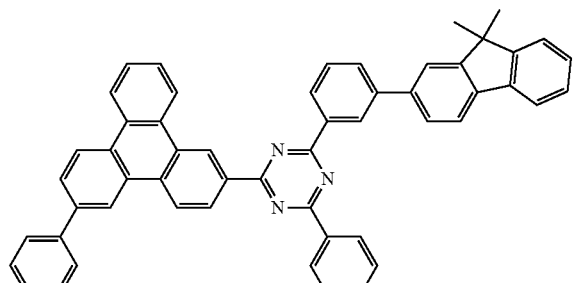
40
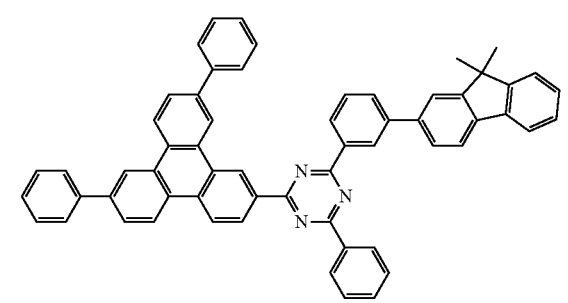
41
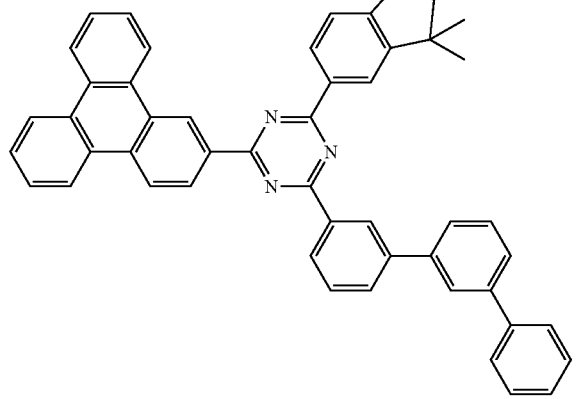
42
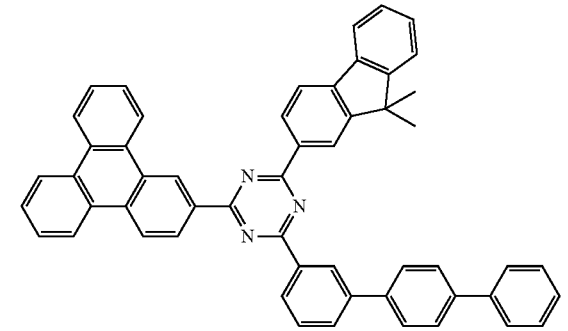

43
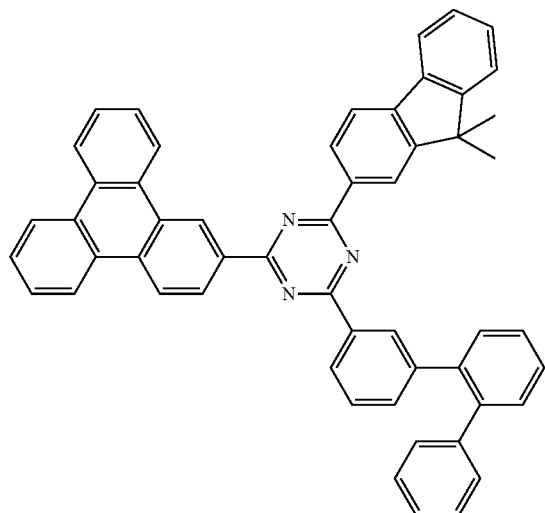
44
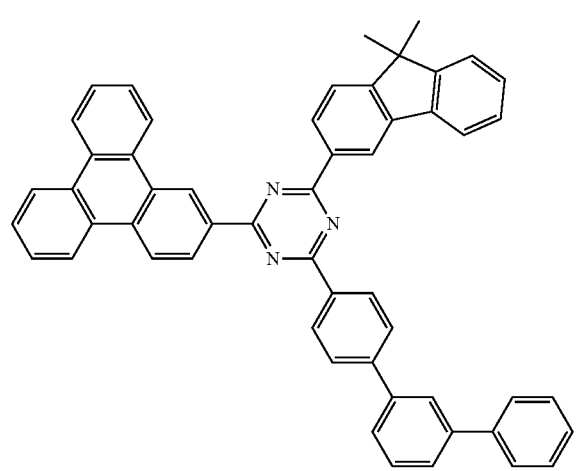
45
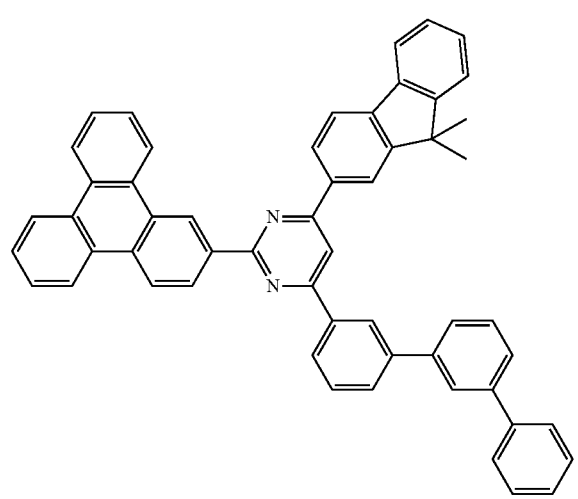
46
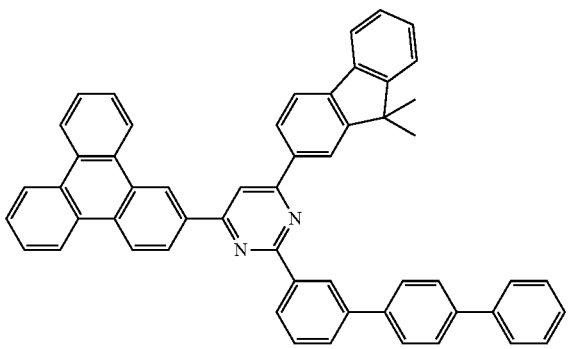
47
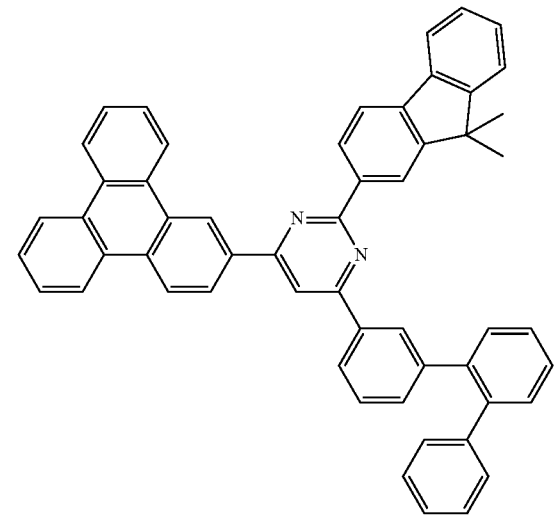
48

-continued

49

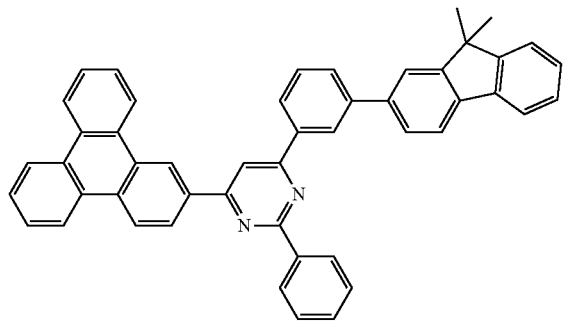

50

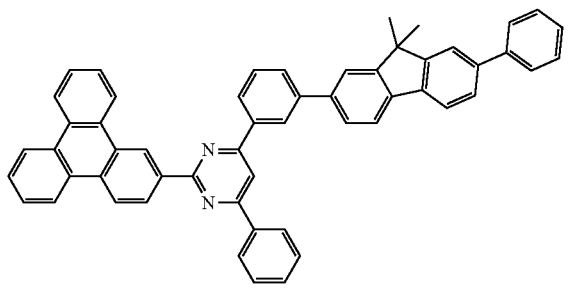

51

The first compound for an organic optoelectronic device may be applied to an organic optoelectronic device and may be applied to an organic optoelectronic device alone or with another compound for an organic optoelectronic device. When the compound for an organic optoelectronic device is used with another compound for an organic optoelectronic device, they may be applied in a form of a composition.

Hereinafter, a composition for an organic optoelectronic device including the first compound for an organic optoelectronic device is for example described.

A composition for an organic optoelectronic device according to another embodiment of the present invention includes the first compound for an organic optoelectronic device; and a second compound for an organic optoelectronic device represented by Chemical Formula 2.

[Chemical Formula 2]

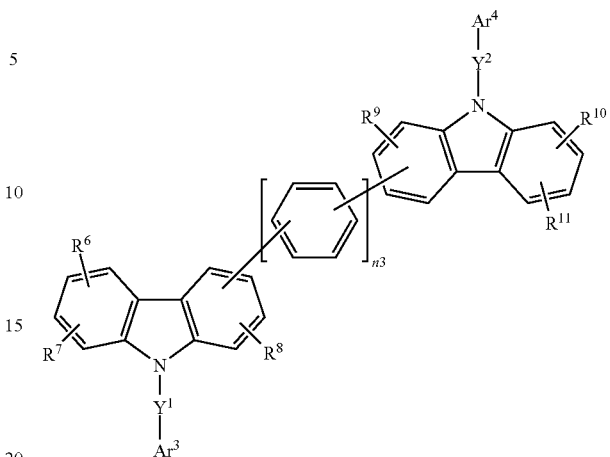

In Chemical Formula 2, $Y^1$ and $Y^2$ are independently a single bond, a substituted or unsubstituted C6 to C30 arylene group, a substituted or unsubstituted C2 to C30 heteroarylene group, or a combination thereof, $Ar^3$ and $Ar^4$ are independently a substituted or unsubstituted C6 to C30 aryl group, a substituted or unsubstituted C2 to C30 heterocyclic group, or a combination thereof, $R^6$ to $R^{11}$ are independently hydrogen, deuterium, a substituted or unsubstituted C1 to C20 alkyl group, a substituted or unsubstituted C6 to C30 aryl group, a substituted or unsubstituted C2 to C50 heterocyclic group, or a combination thereof, and n3 is an integer of 0 to 2;

wherein the "substituted" refers to replacement of at least one hydrogen by deuterium, a C1 to C4 alkyl group, a C6 to C18 aryl group, or a C2 to C18 heteroaryl group. In a specific example of the present invention, the "substituted" refers to replacement of at least one hydrogen by deuterium, a phenyl group, an ortho-biphenyl group, a meta-biphenyl group, a para-biphenyl group, a terphenyl group, a naphthyl group, a dibenzofuranyl group, or a dibenzothiophenyl group.

In an example embodiment of the present invention, $Y^1$ and $Y^2$ of Chemical Formula 2 may independently be a single bond, or a substituted or unsubstituted C6 to C18 arylene group.

In an example embodiment of the present invention, $Ar^3$ and $Ar^4$ of Chemical Formula 2 may independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolyl group, a substituted or unsubstituted isoquinazolyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof. Specifically, they may be a substituted or unsubstituted phenyl group, a substituted or unsubstituted biphenyl group, a substituted or unsubstituted terphenyl group, a substituted or unsubstituted naphthyl group, a substituted or unsubstituted triphenylenyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted quinazolyl group, a substituted or unsubstituted isoquinazolyl group, a substituted or unsubstituted dibenzothiophenyl group, a substituted or unsubstituted dibenzofuranyl group, a substituted or unsubstituted carbazolyl group, or a substituted or unsubstituted fluorenyl group, and more specifically substituted or unsubstituted phenyl group, a substituted or unsubstituted biphenyl group, a substituted or unsubstituted terphenyl group, a substituted or unsubstituted naphthyl group, a substituted or unsubstituted triphenylenyl group, a substituted or unsubstituted pyridinyl group, a substituted or unsubstituted pyrimidinyl group, a substituted or unsubstituted dibenzothiophenyl group, a substituted or unsubstituted dibenzofuranyl group, a substituted or unsubstituted carbazolyl group, or a substituted or unsubstituted fluorenyl group.

In an example embodiment of the present invention, $R^6$ to $R^{11}$ of Chemical Formula 2 may independently be hydrogen, deuterium, or a substituted or unsubstituted C6 to C12 aryl group, and may be for example hydrogen, deuterium, a phenyl group, or a biphenyl group.

In an example embodiment of the present invention. n3 of Chemical Formula 2 may be 0 or 1.

in a specific example the present invention, Chemical Formula 2 may have one of structures of Group III and *—$Y^1$—$Ar^3$ and *—$Y^2$—$Ar^4$ may be one of substituents of Group IV.

[Group III]

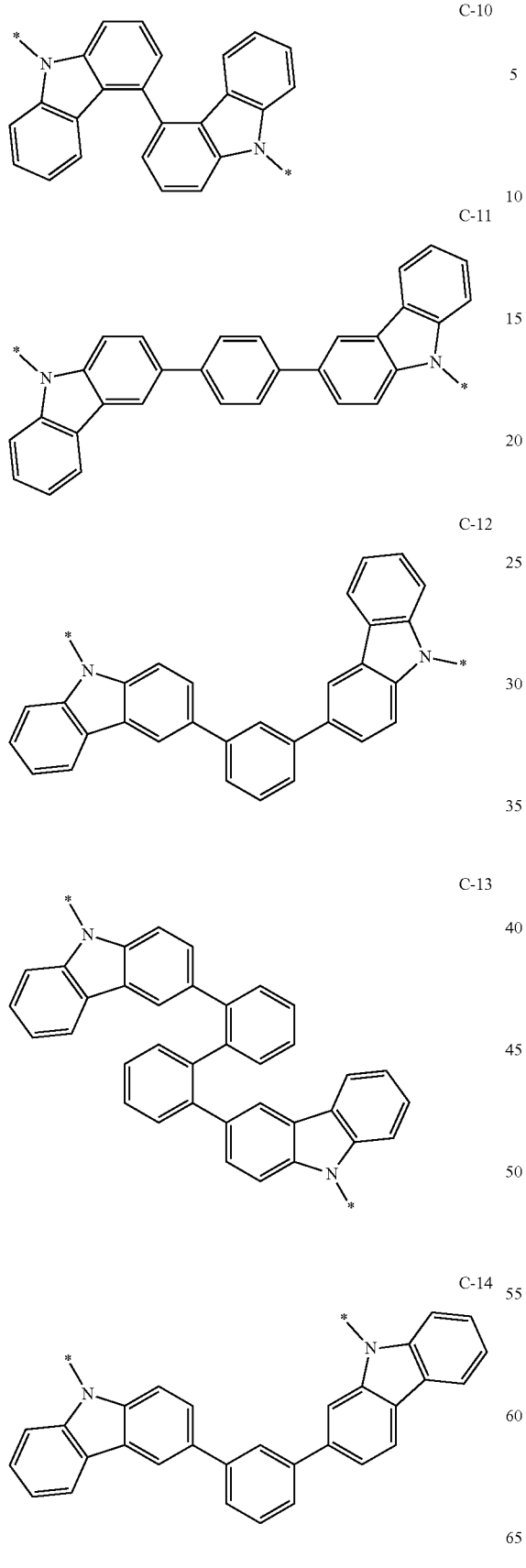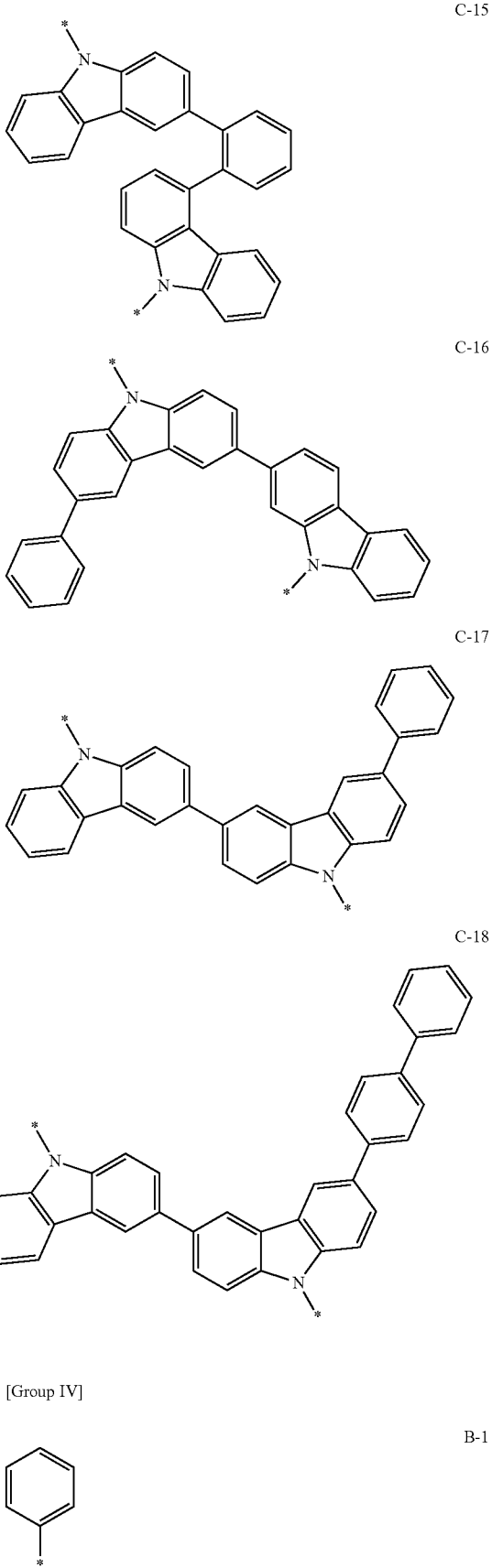

-continued
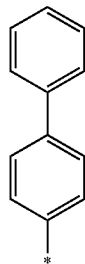
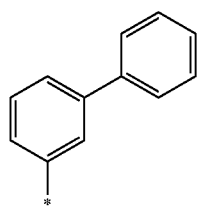
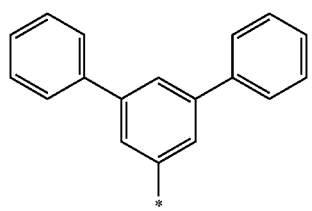
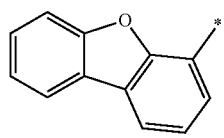
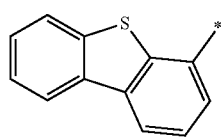
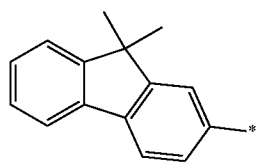
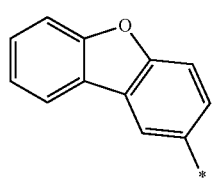
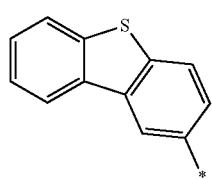
-continued
B-2
B-3
B-4
B-5
B-6
B-7
B-8
B-9
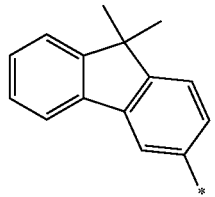
B-10
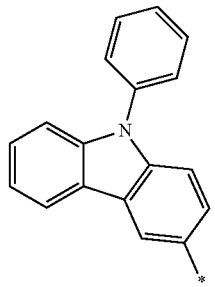
B-11
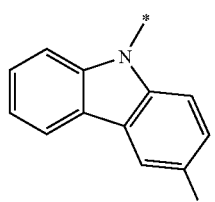
B-12
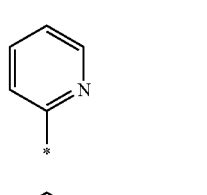
B-13
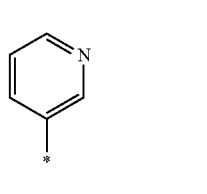
B-14
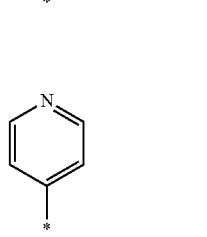
B-15
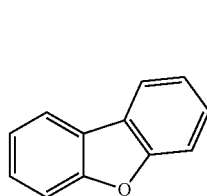
B-16
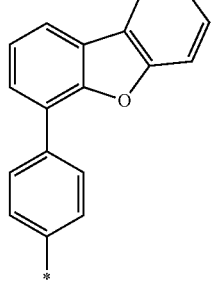

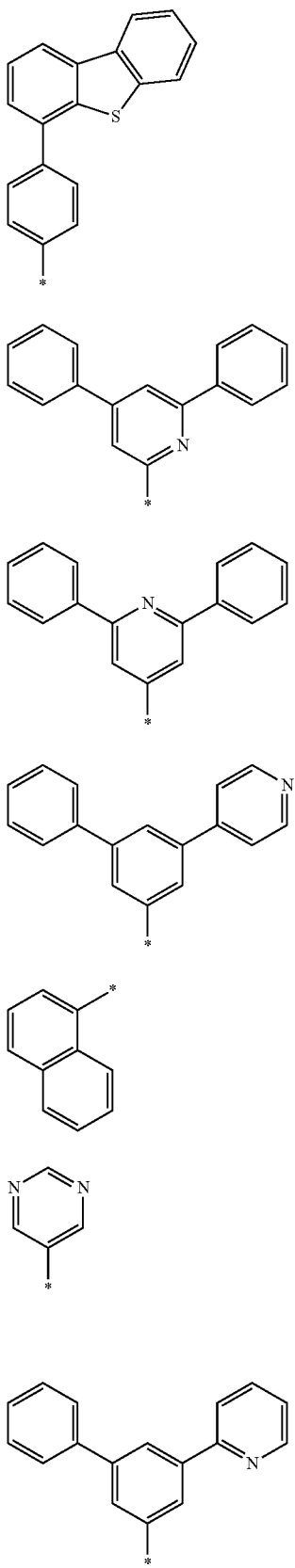

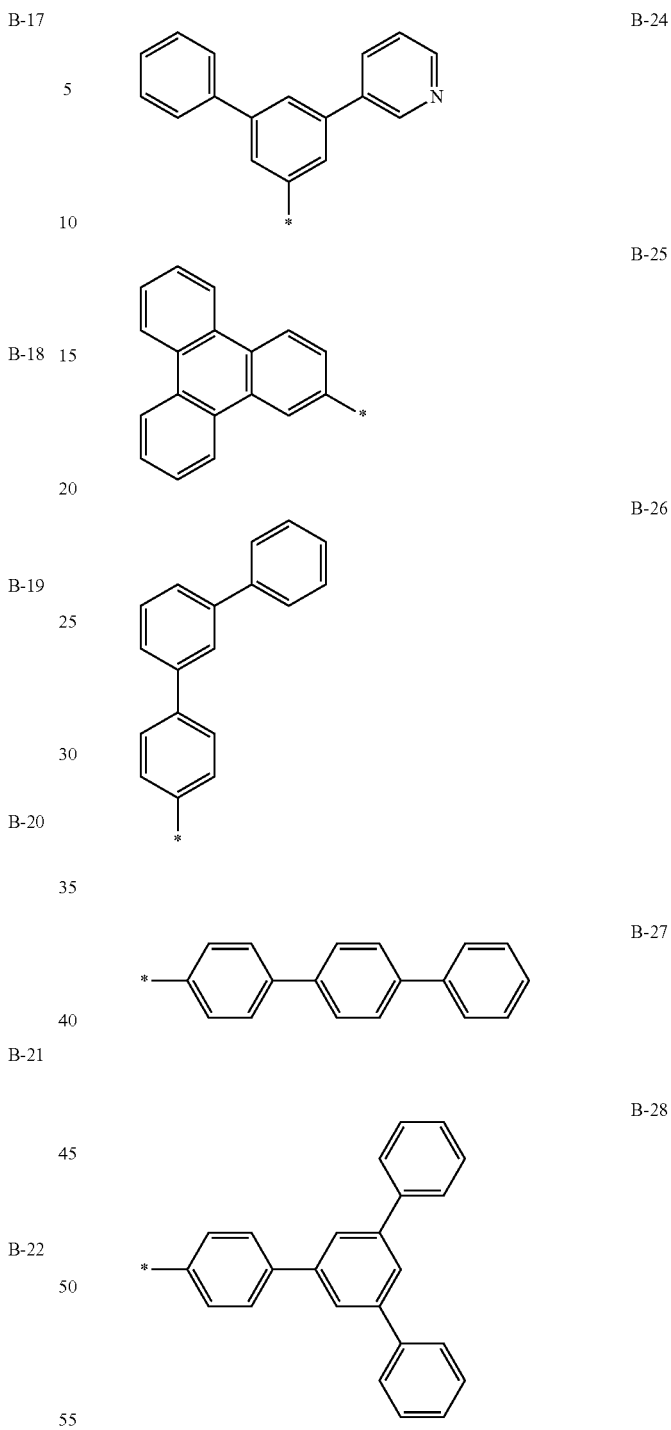

In Group III and Group IV, * is a linking point.

In an example the present invention, Chemical Formula 2 may be selected from c-5, c-6, c-8, and c-17 of Group III, *—Y$^L$—Ar$^3$ and *—Y$^2$—Ar$^4$ of Chemical Formula 2 may be selected from substituents, B-1, B-2, B-3, B-13, B-18, B-25, B-26, and B-28 of Group IV.

The second compound for an organic optoelectronic device represented by Chemical Formula 2 may be for example compounds of Group 2, but is not limited thereto.

[Group 2]
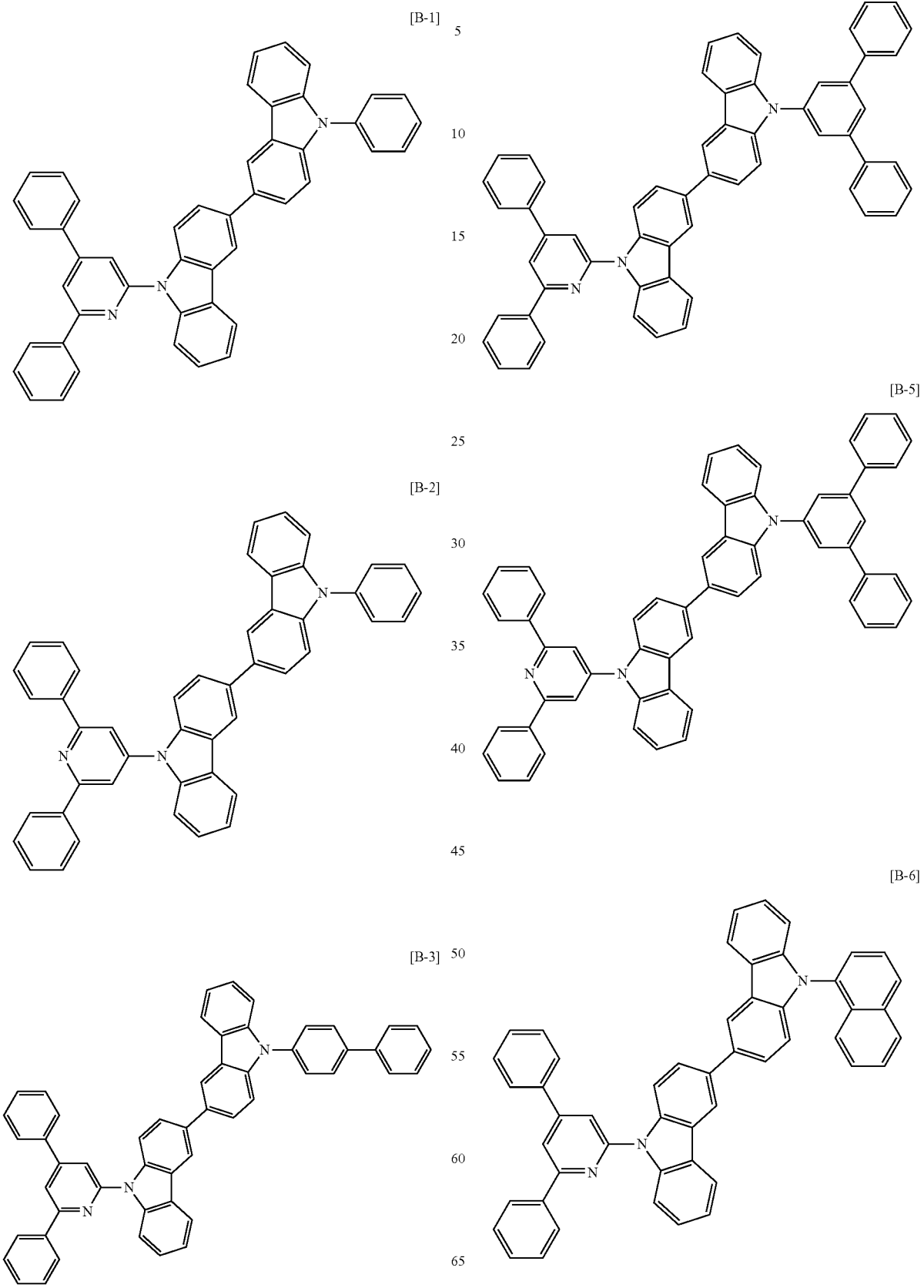

[B-7]
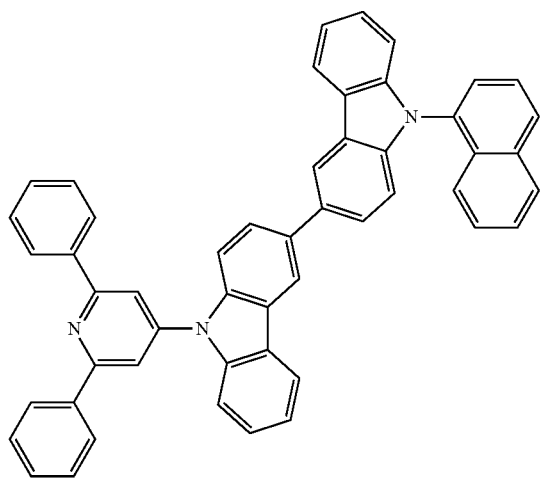
[B-8]
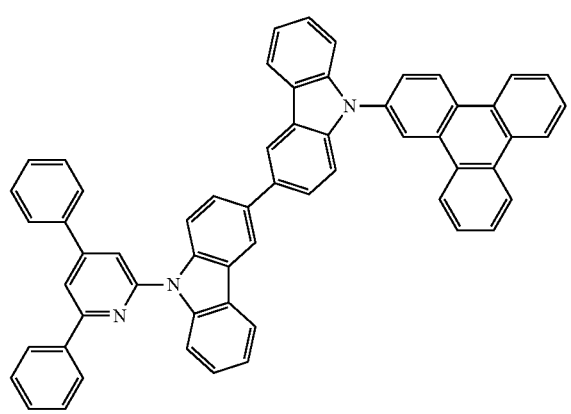
[B-9]
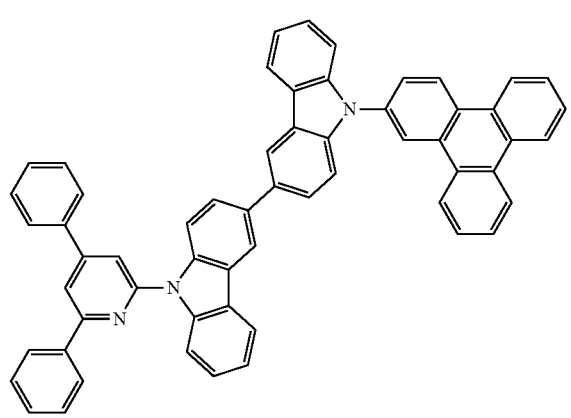
[B-10]
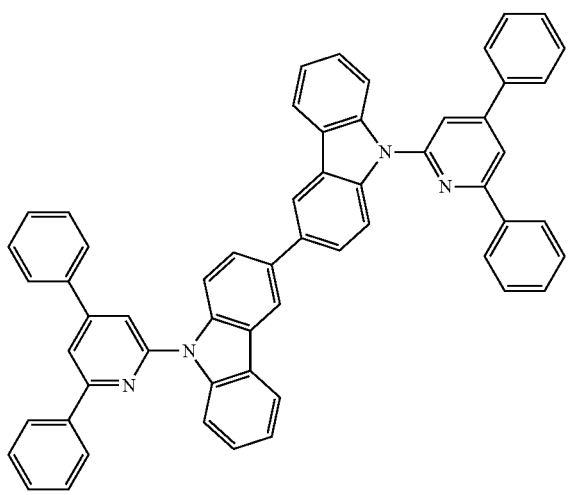
[B-11]
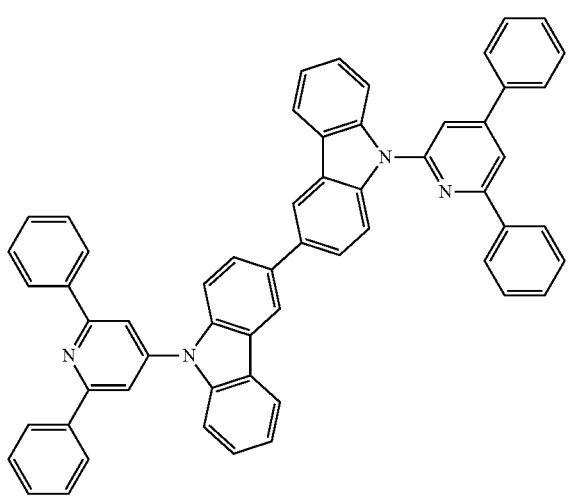
[B-12]
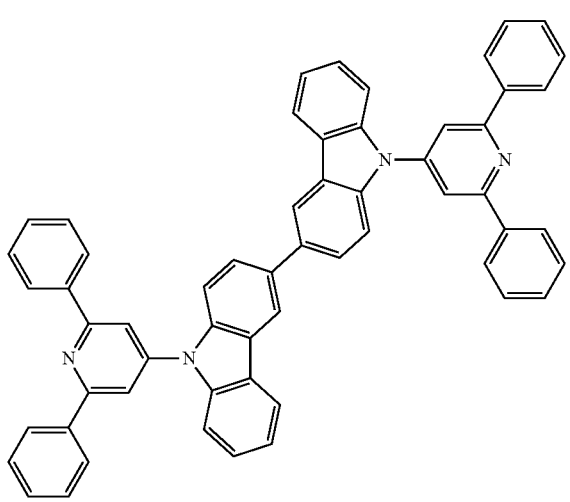

[B-13]
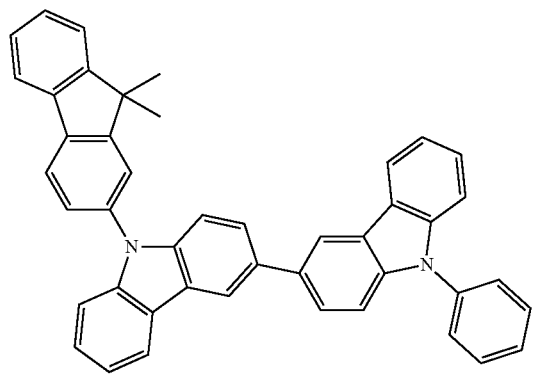
[B-16]
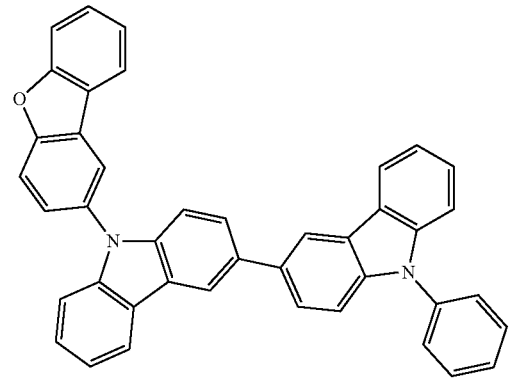
[B-14]
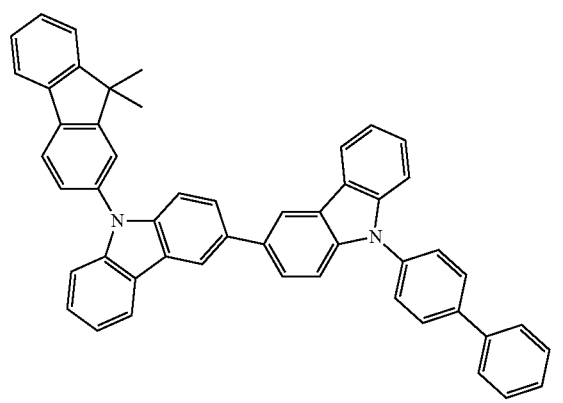
[B-17]
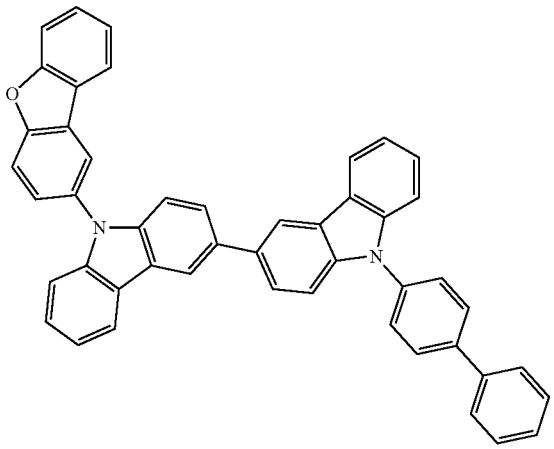
[B-15]
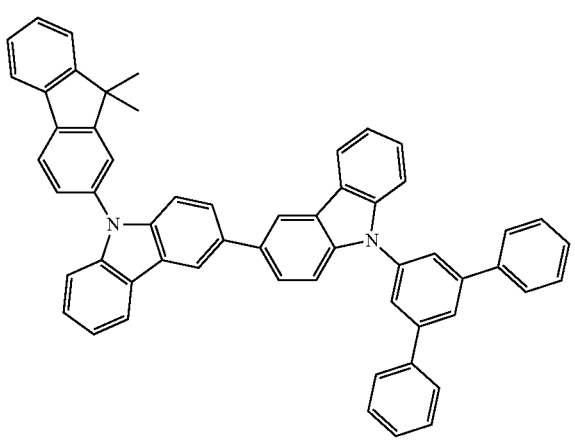
[B-18]
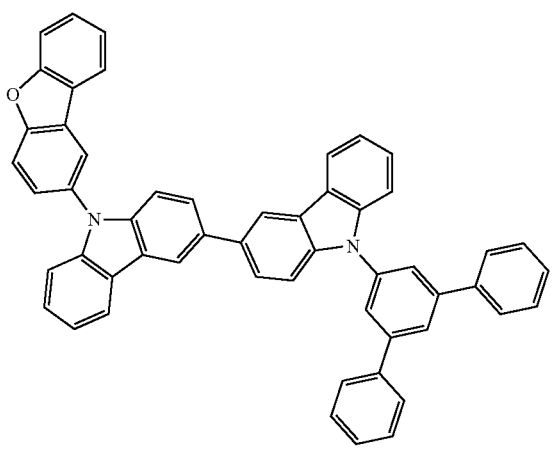

-continued
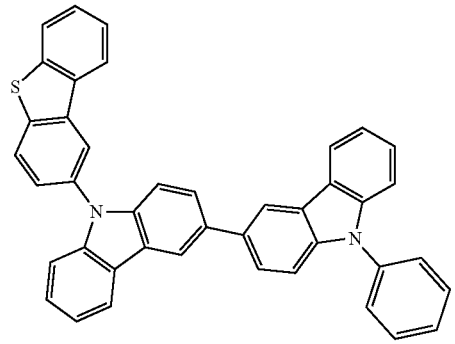
[B-19]
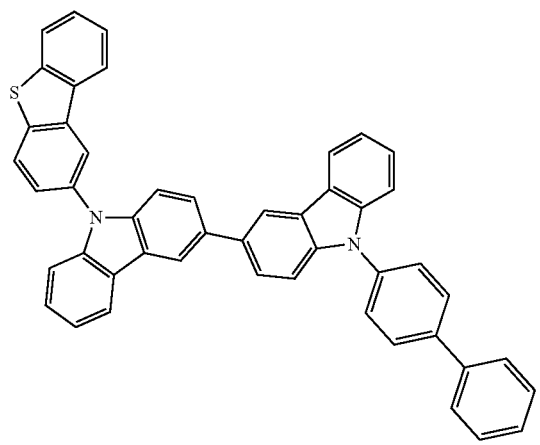
[B-20]
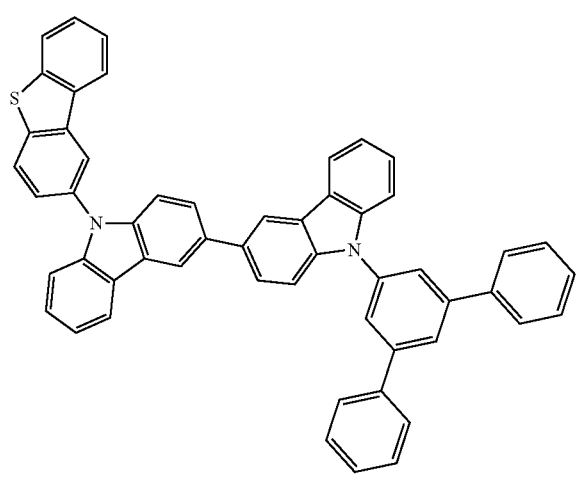
[B-21]
-continued
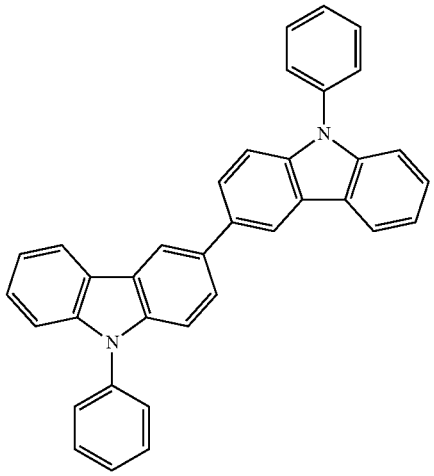
[B-22]
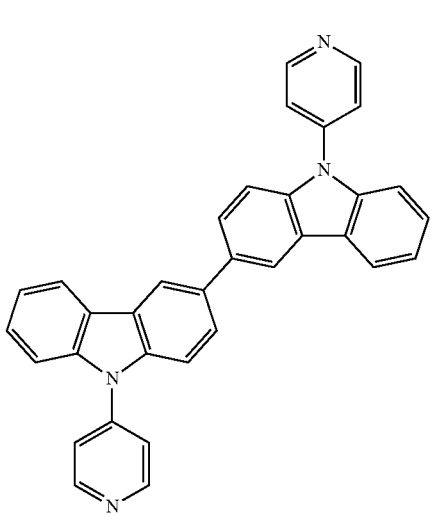
[B-23]
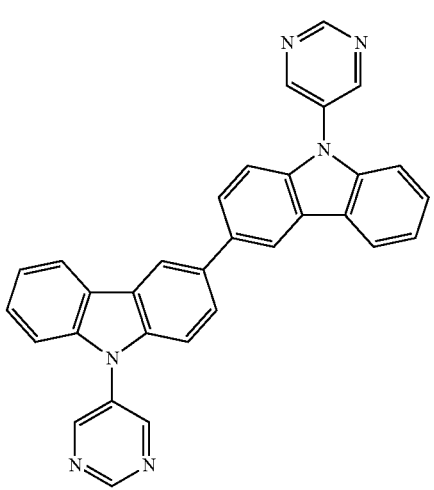
[B-24]

[B-25]
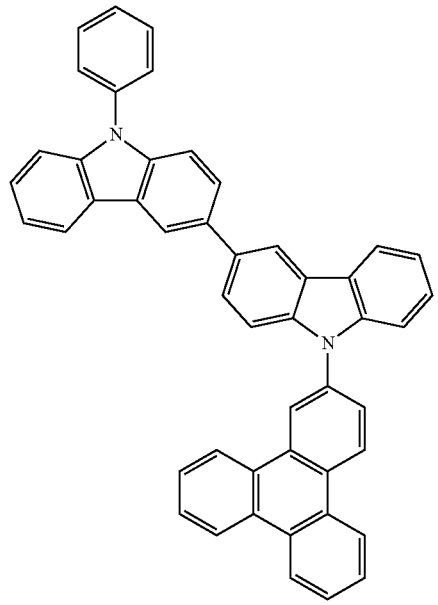
[B-27]
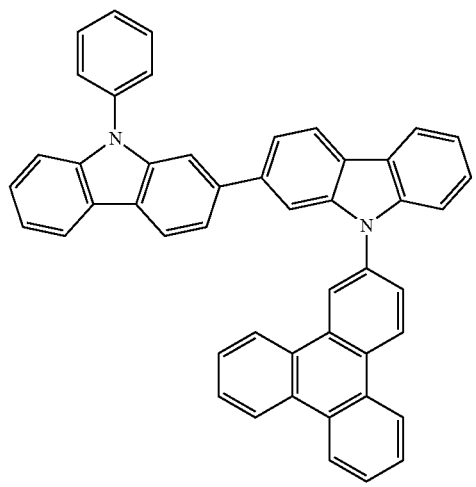
[B-28]
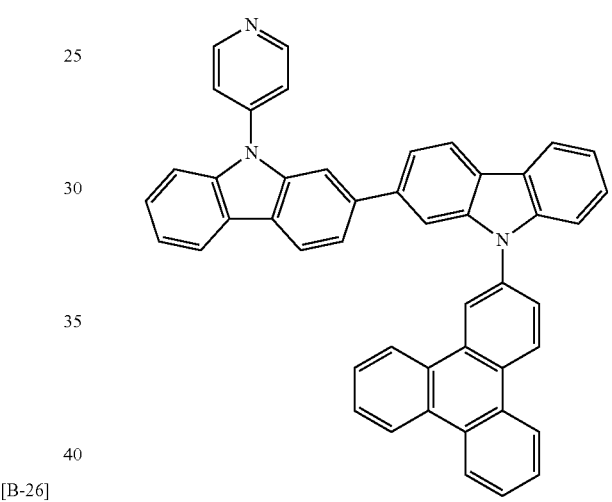
[B-26]
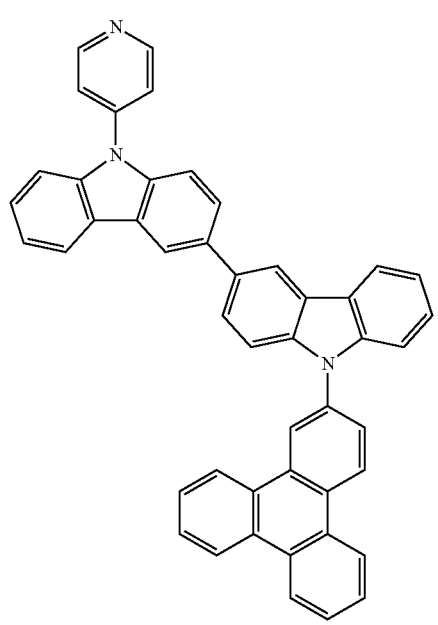
[B-29]
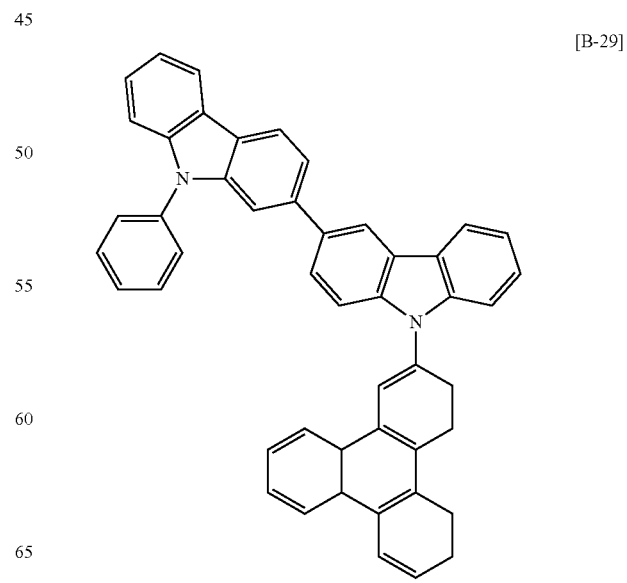

[B-30]
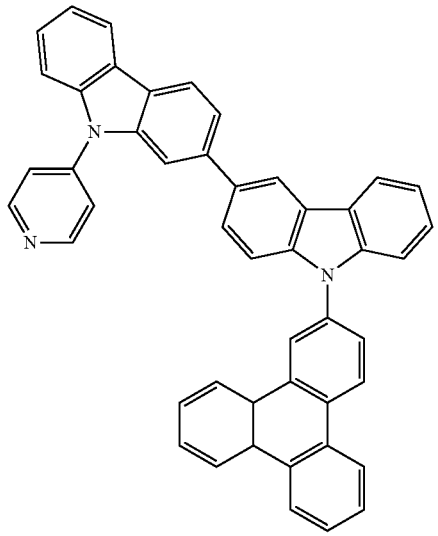
[B-32]
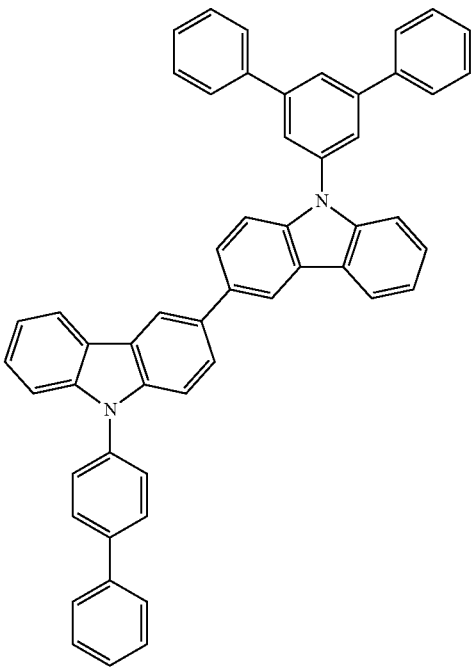
[B-31]
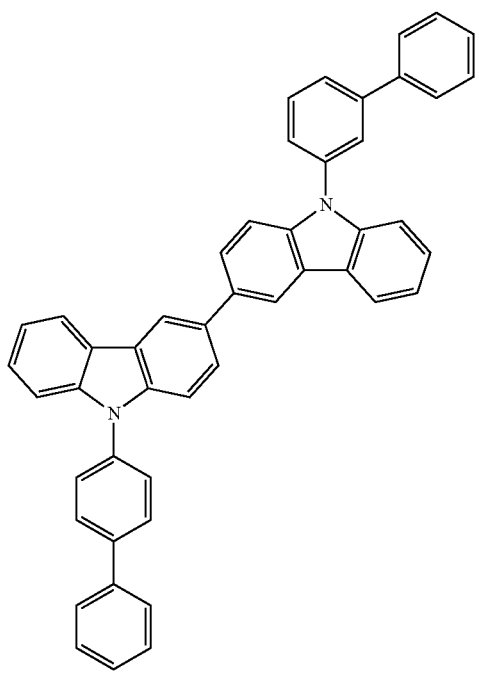
[B-33]
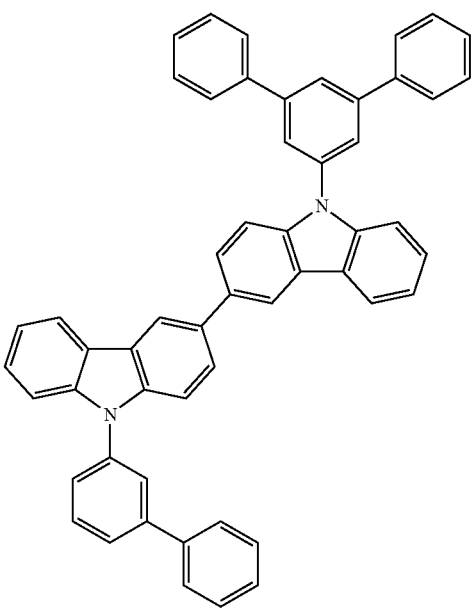

[B-34]
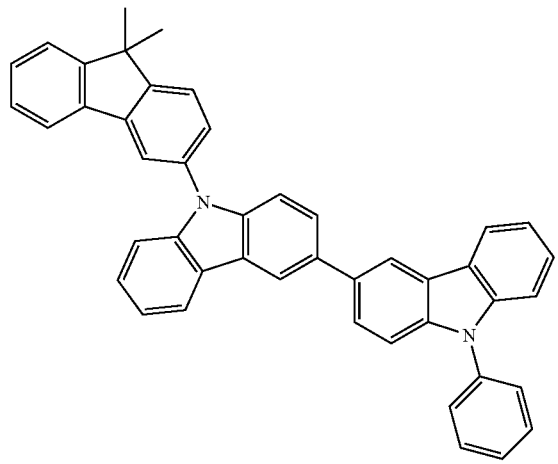
[B-35]
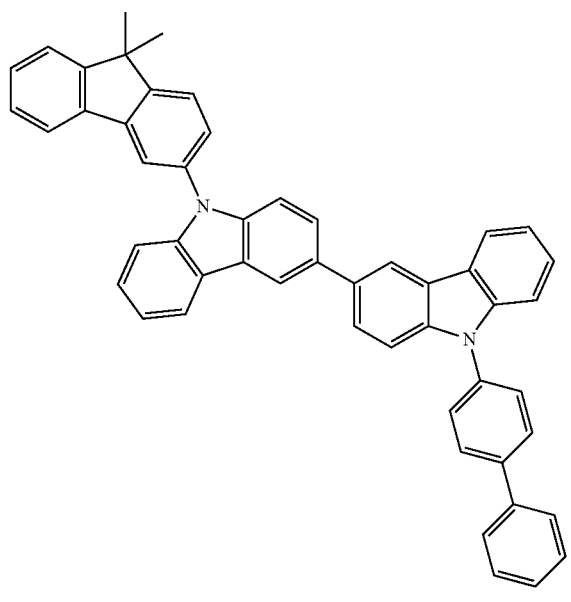
[B-36]
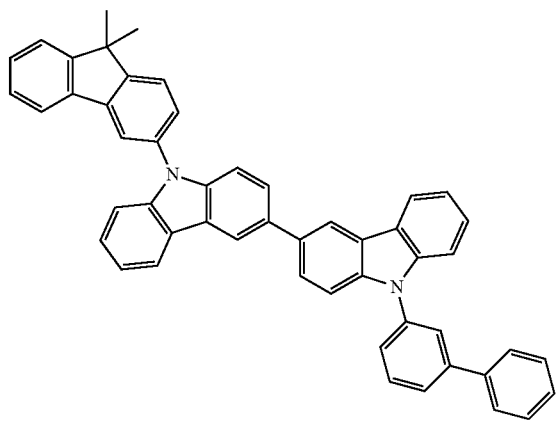
[B-37]
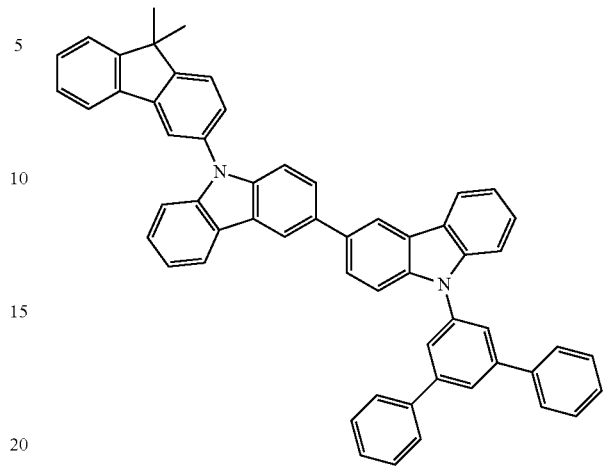
[B-38]
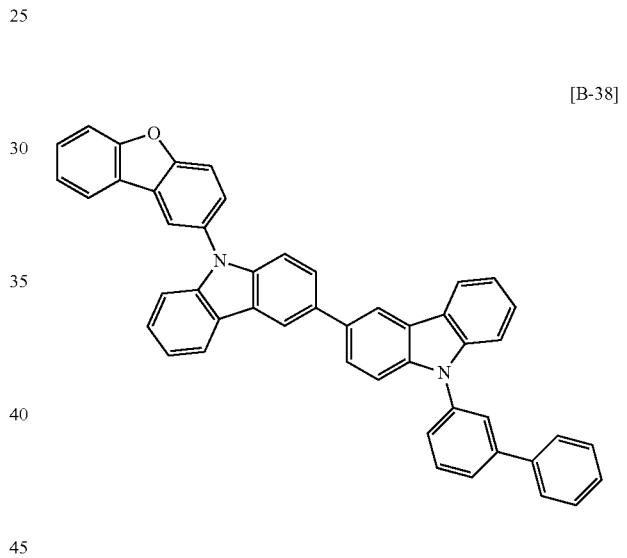
[B-39]
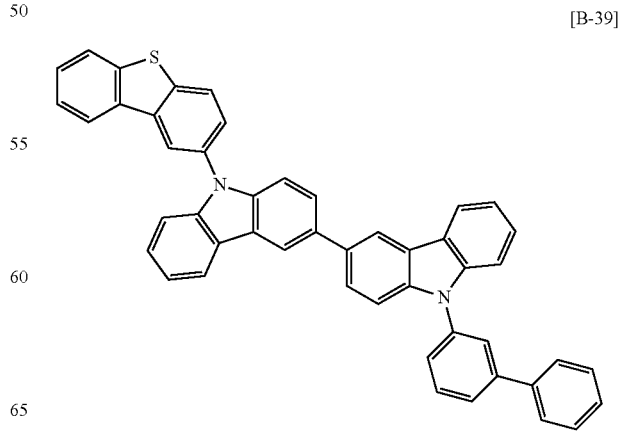

[B-40]
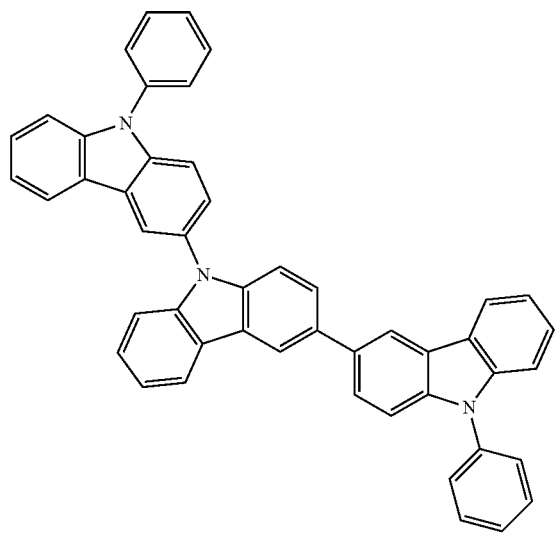
[B-41]
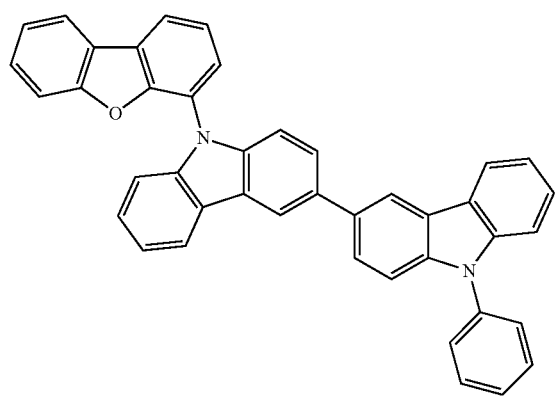
[B-42]
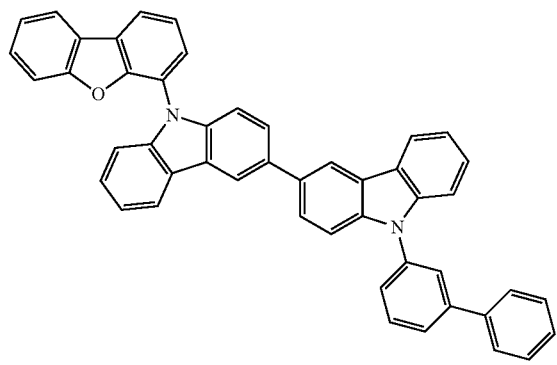
[B-43]
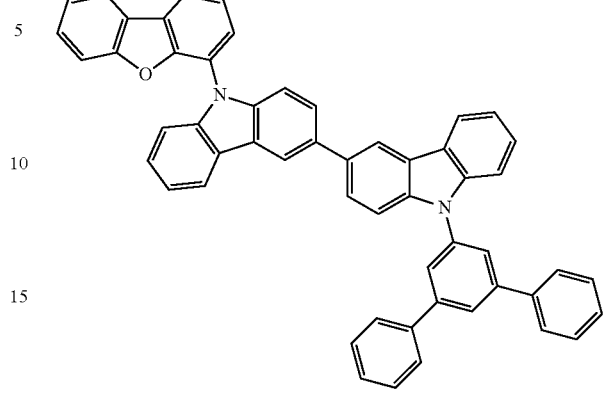
[B-44]
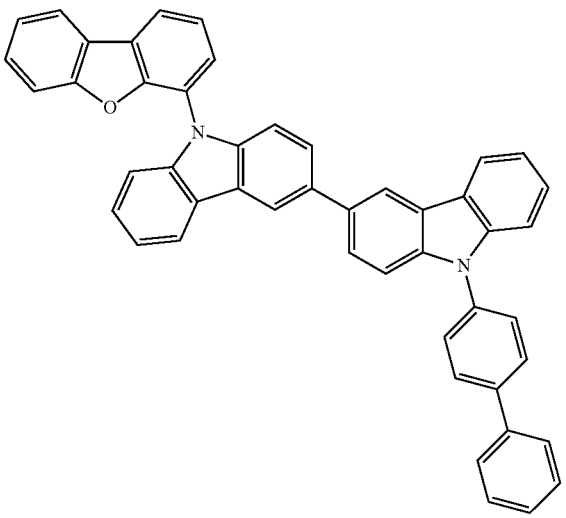
[B-45]
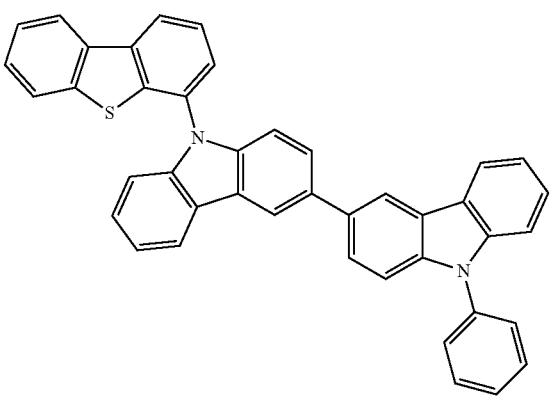

[B-46]
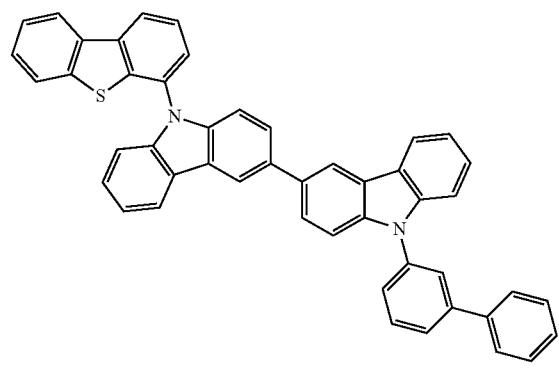
[B-49]
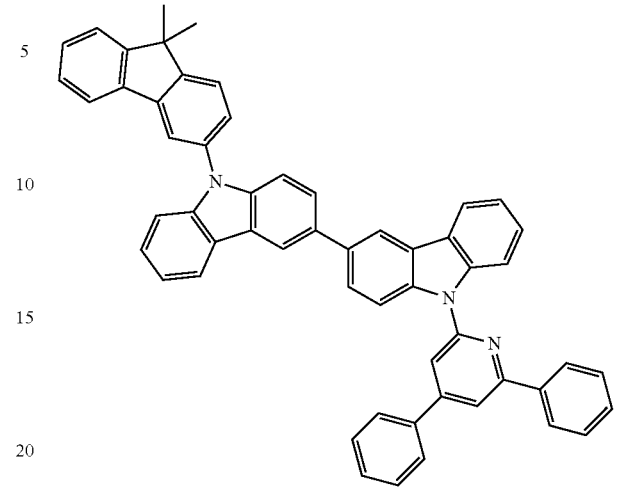
[B-47]
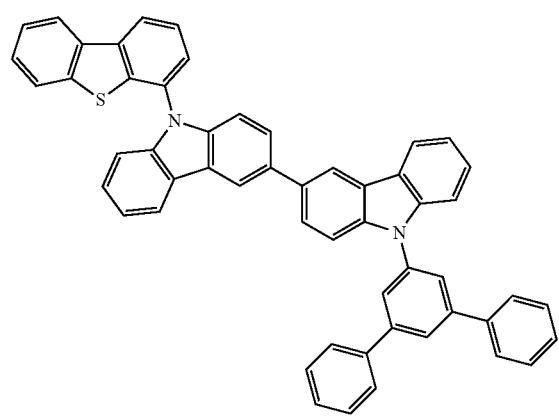
[B-50]
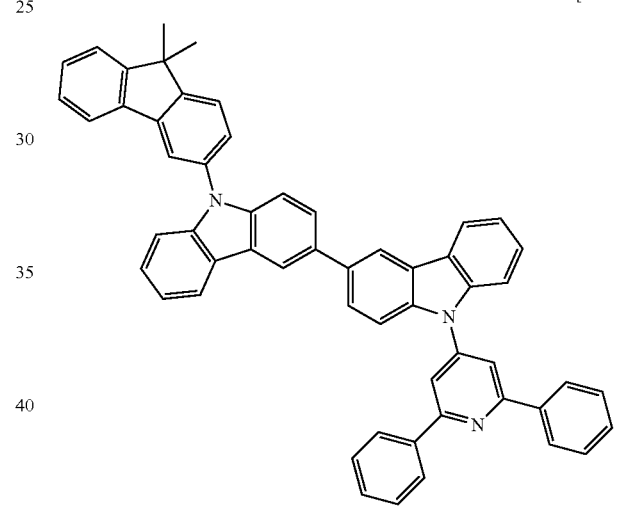
[B-48]
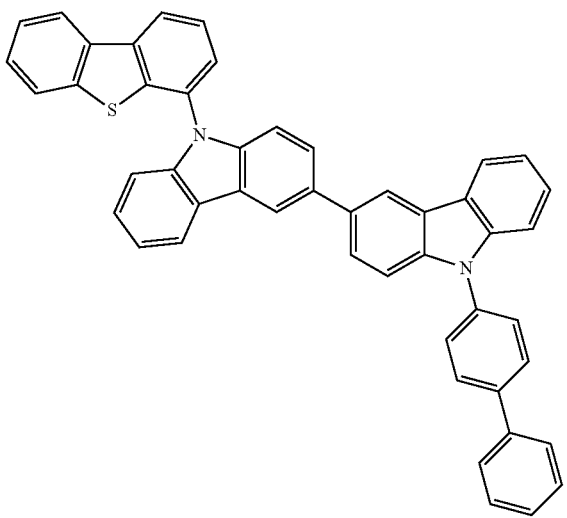
[B-51]
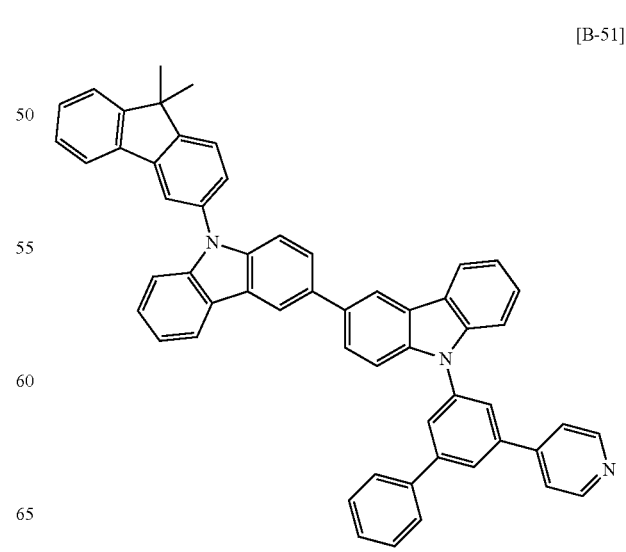

[B-52]
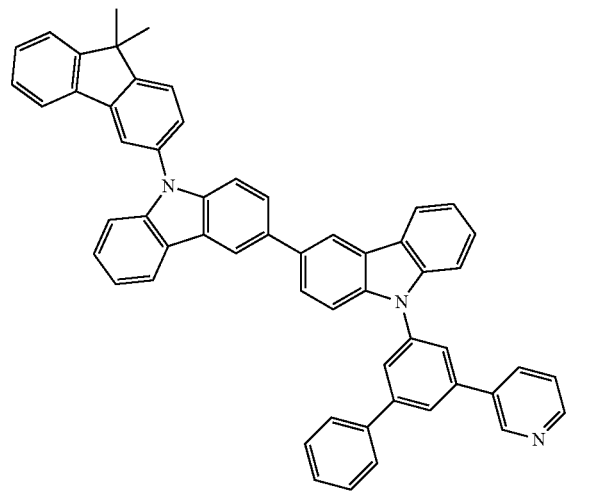
[B-55]
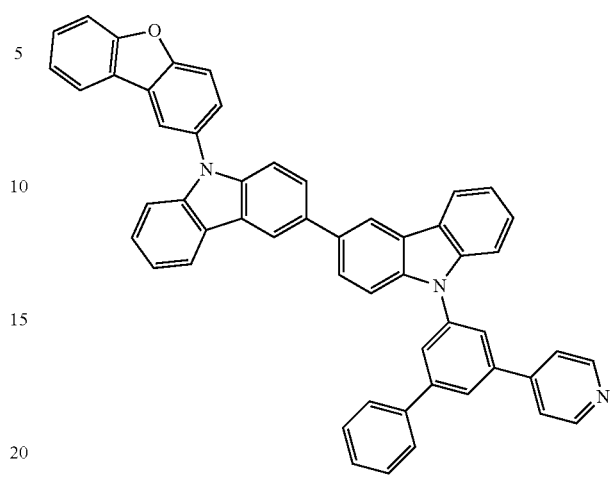
[B-53]
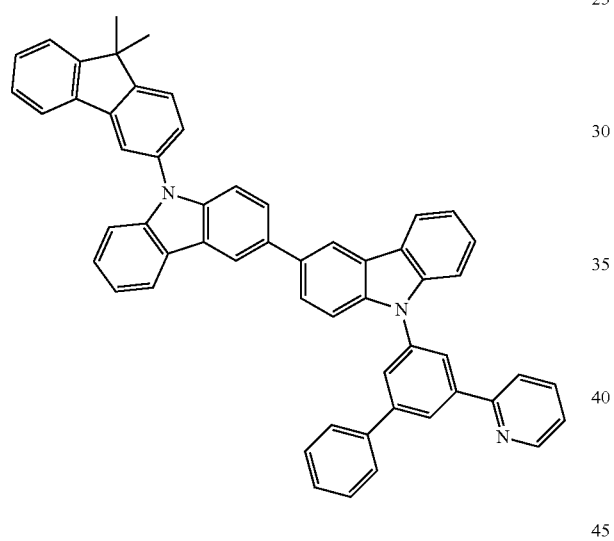
[B-56]
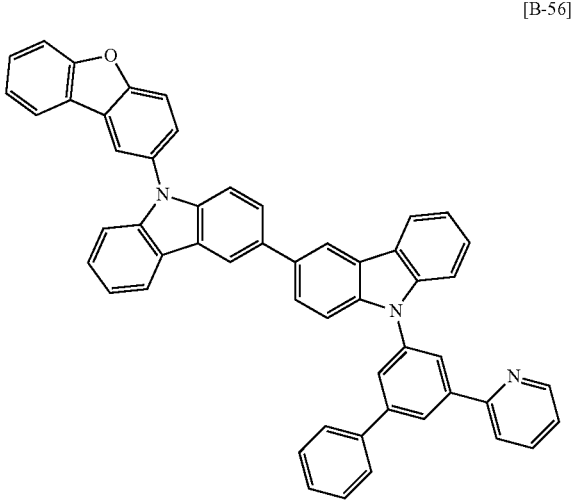
[B-54]
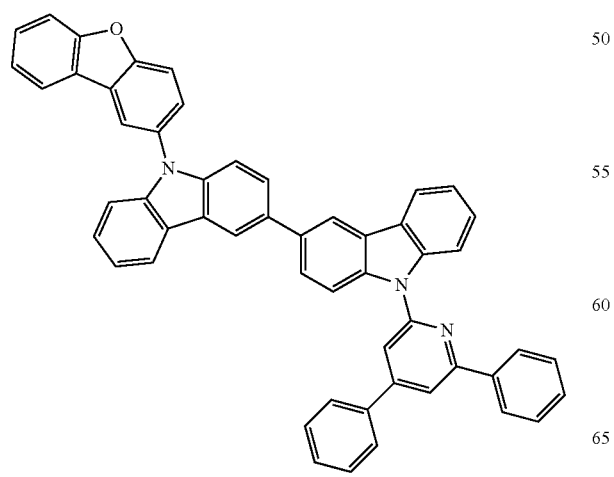
[B-57]
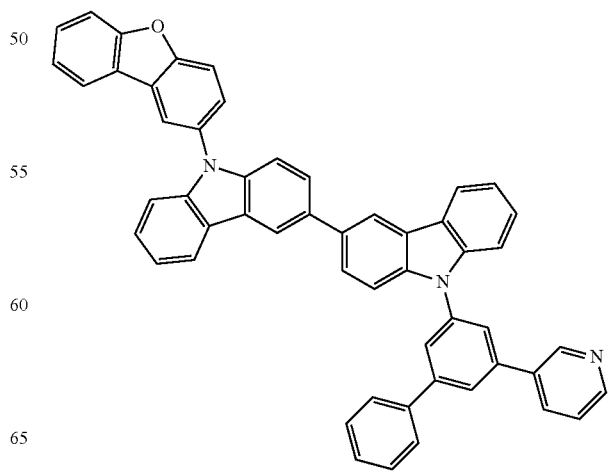

[B-58]
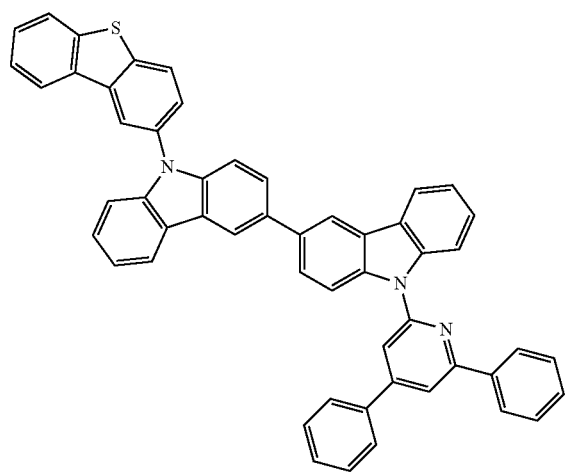
[B-61]
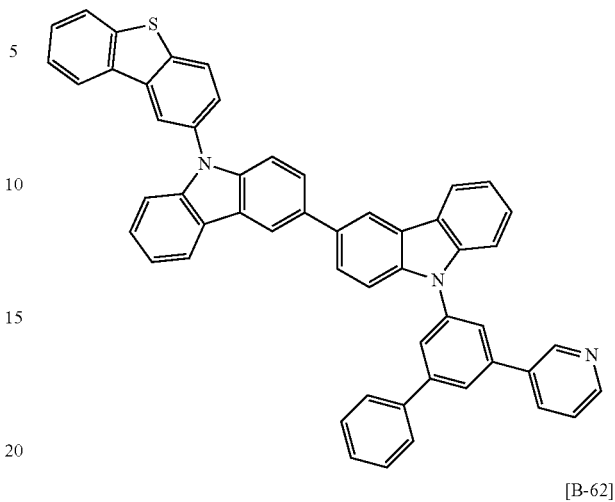
[B-59]
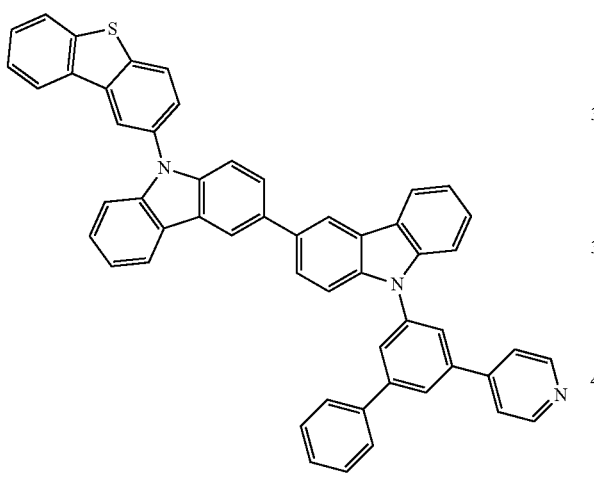
[B-62]
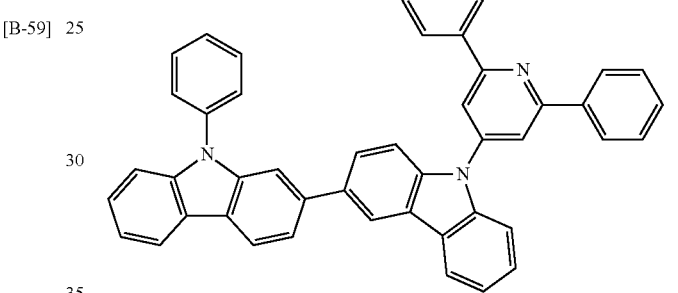
[B-63]
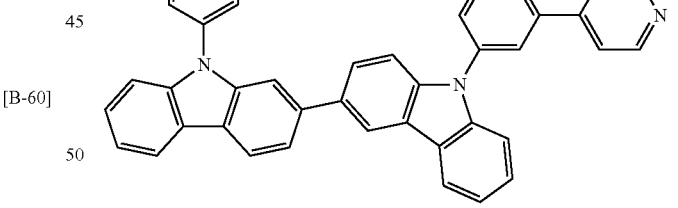
[B-60]
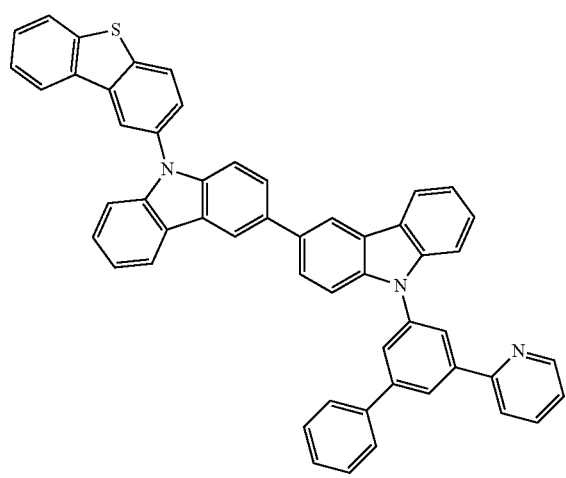
[B-64]
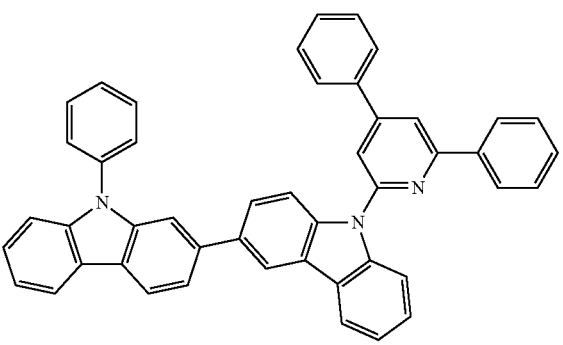

-continued
[B-65]
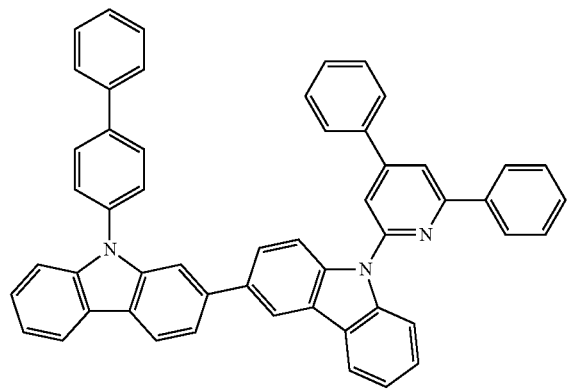
[B-66]
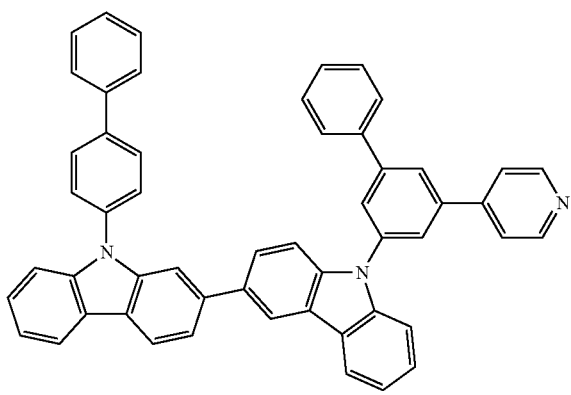
[B-67]
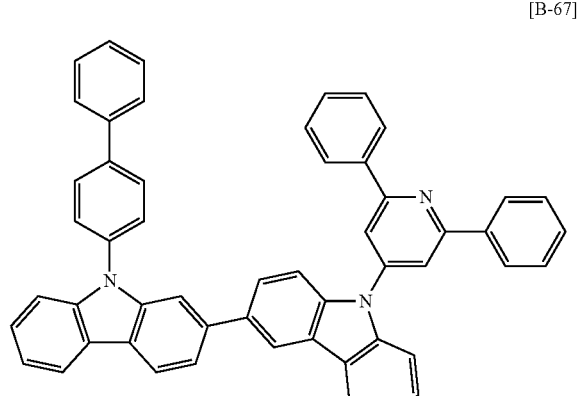
[B-68]
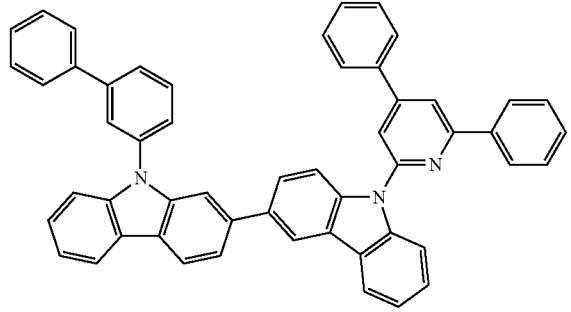
-continued
[B-69]
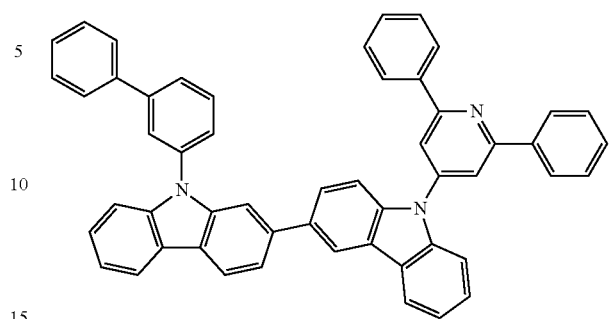
[B-70]
[B-71]
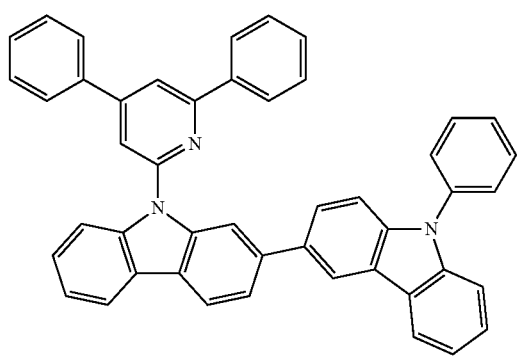
[B-72]
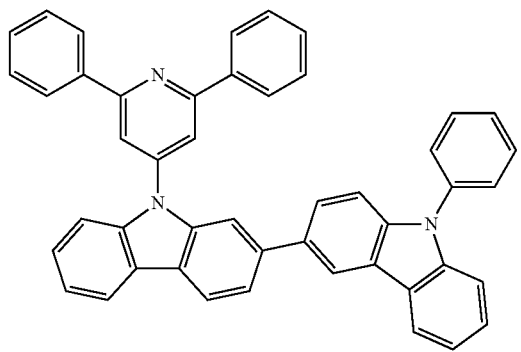

[B-73]
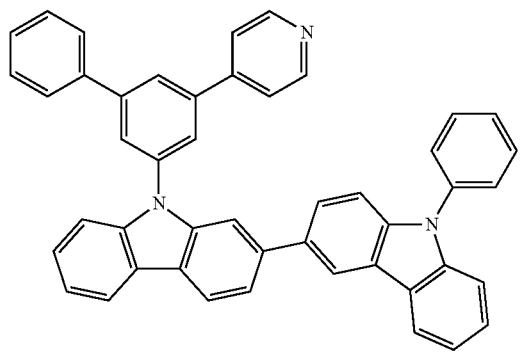
[B-74]
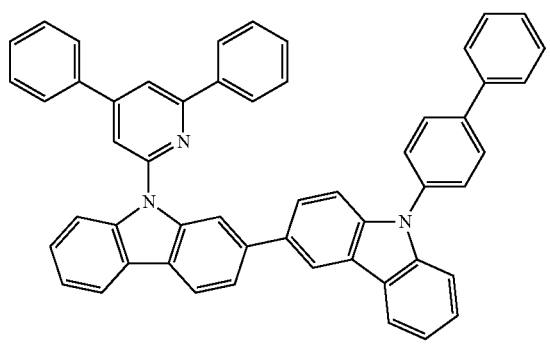
[B-75]
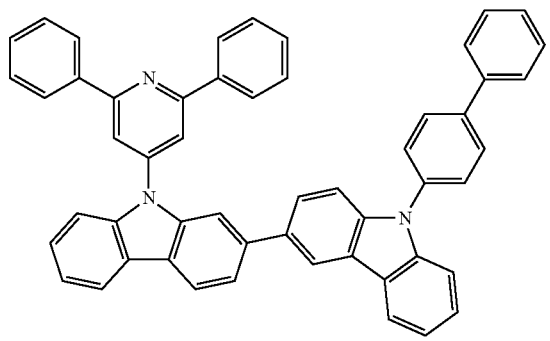
[B-76]
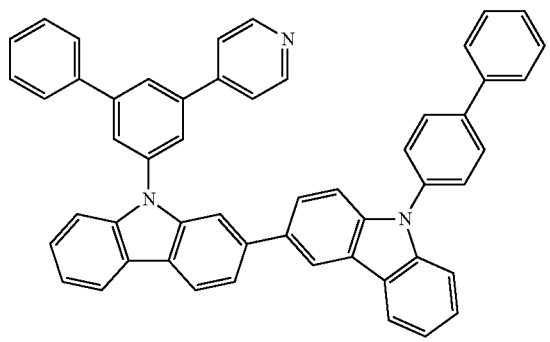
[B-77]
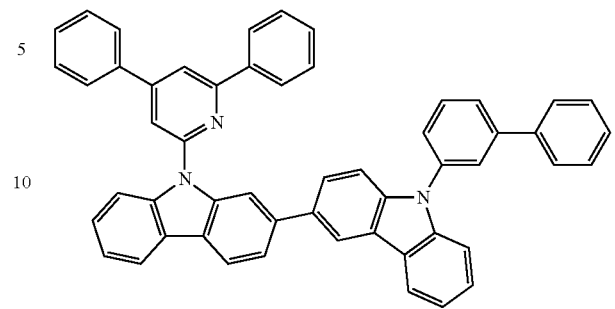
[B-78]
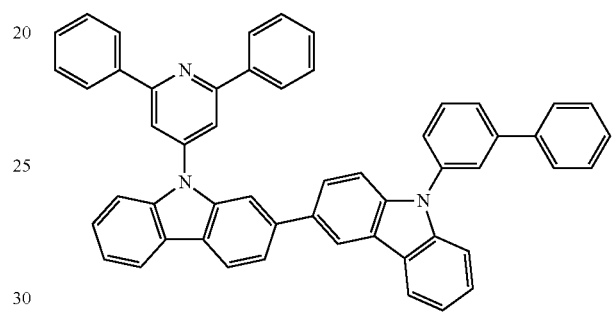
[B-79]
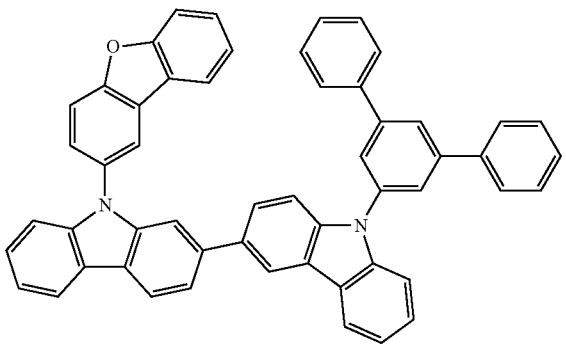
[B-80]

[B-81]
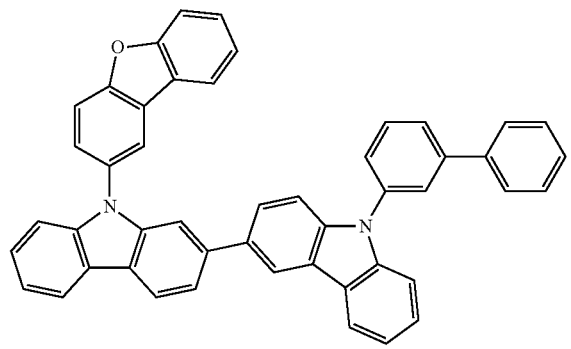
[B-85]
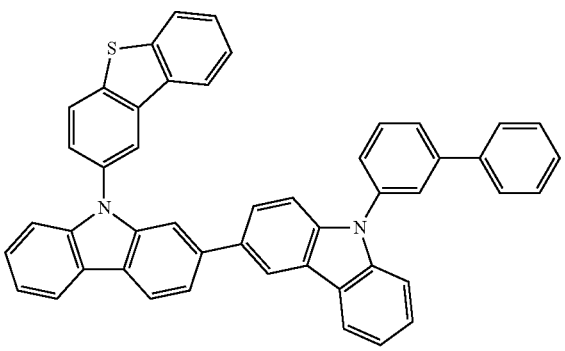
[B-82]
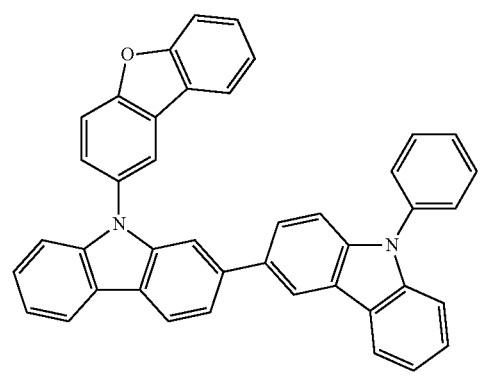
[B-86]
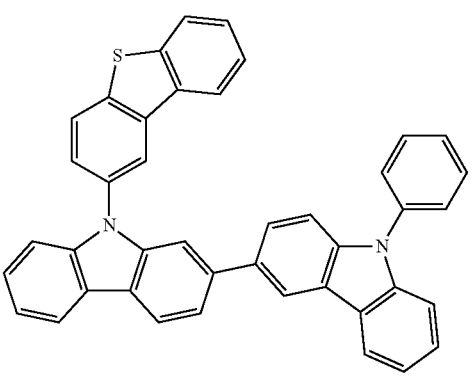
[B-87]
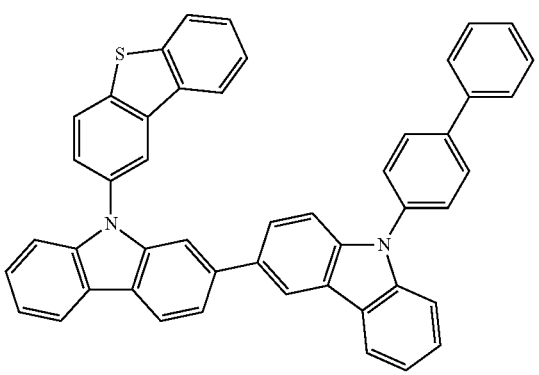
[B-83]
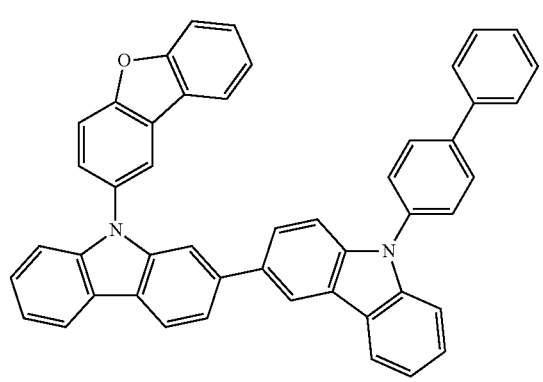
[B-84]
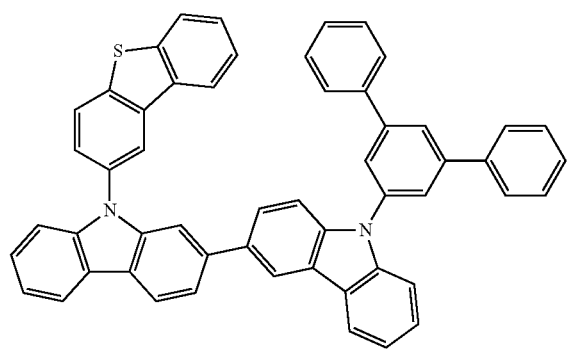
[B-88]
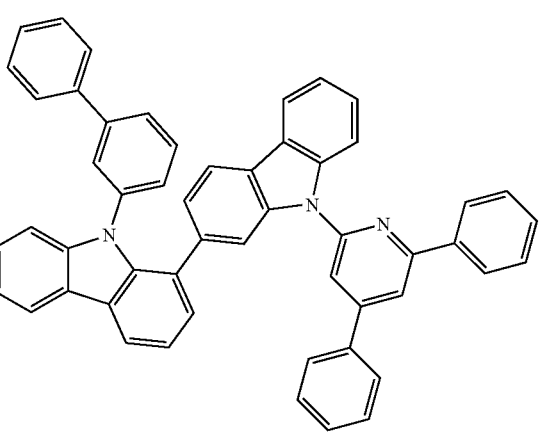

[B-89]
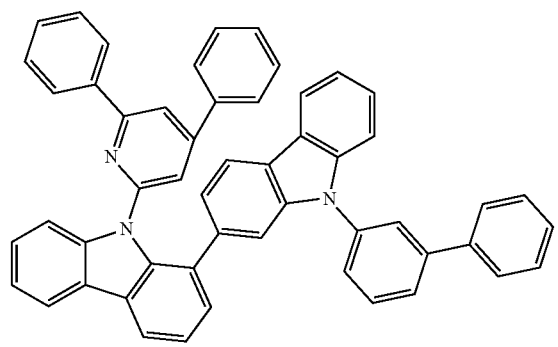
[B-90]
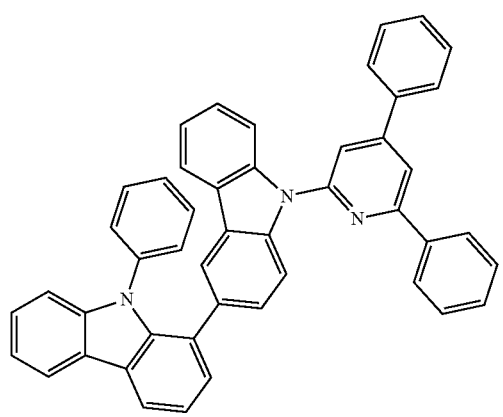
[B-91]
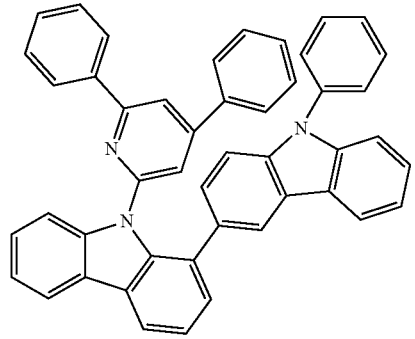
[B-92]
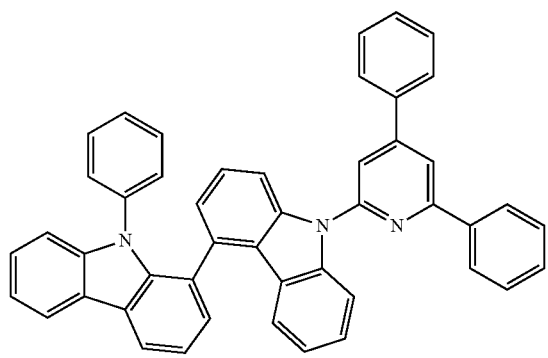
[B-93]
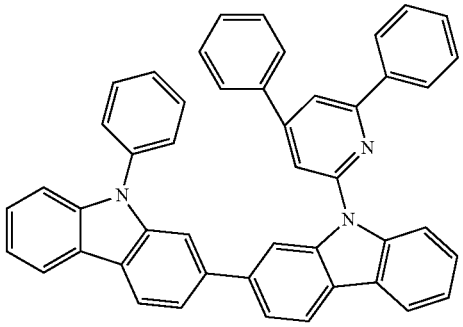
[B-94]
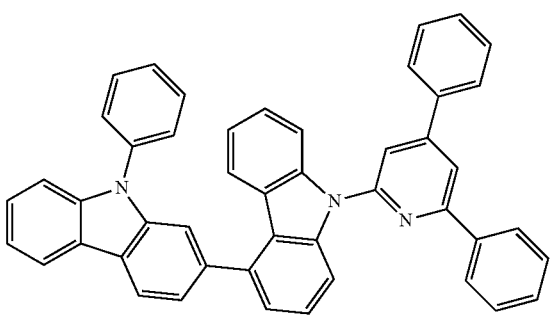
[B-95]
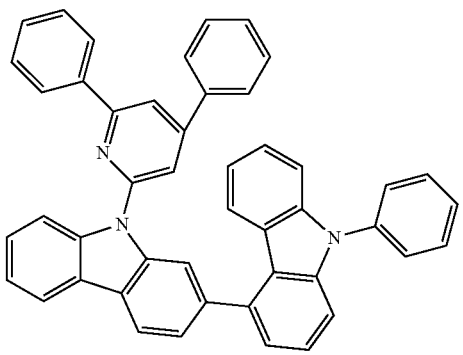
[B-96]
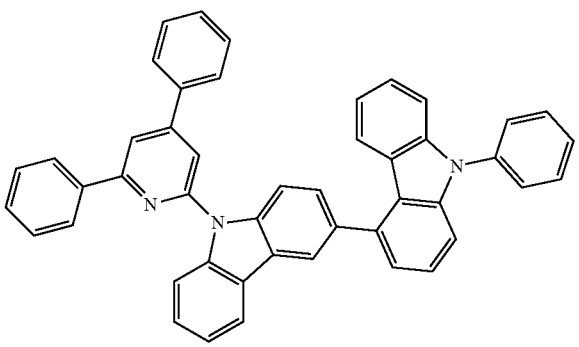

[B-97]
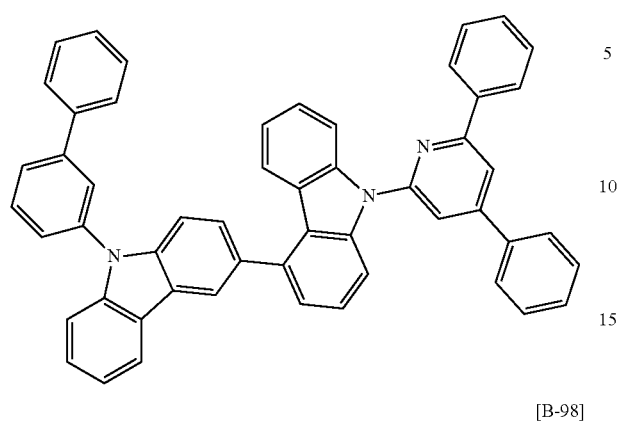
[B-98]
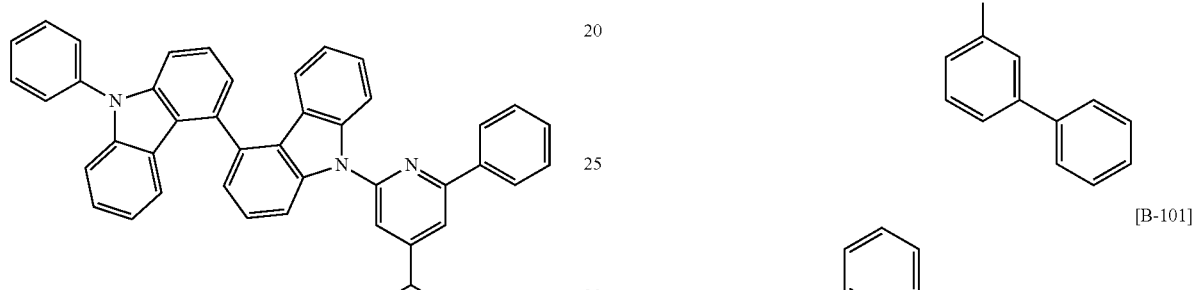
[B-99]
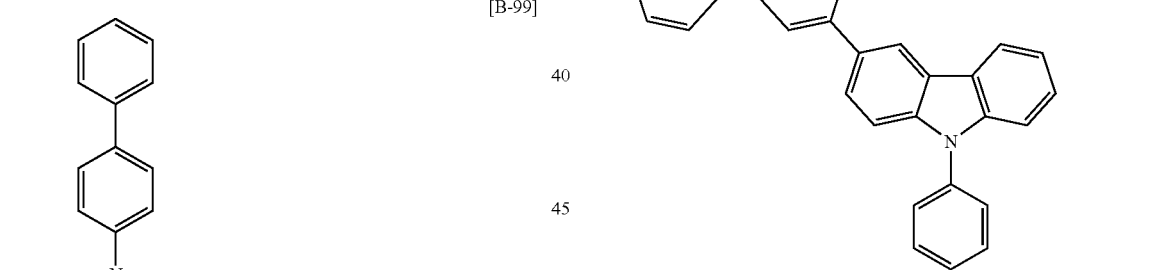
[B-100]
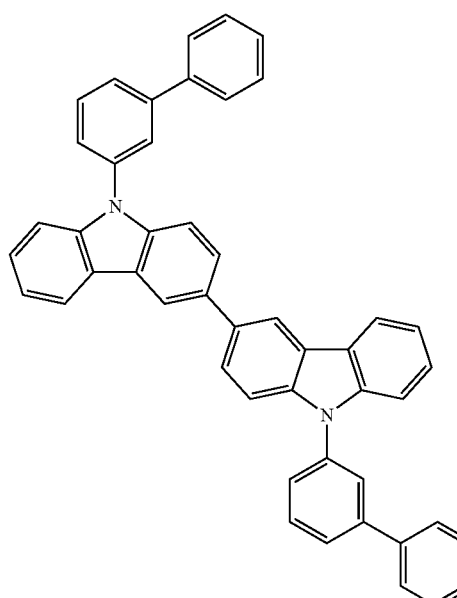
[B-101]
[B-102]
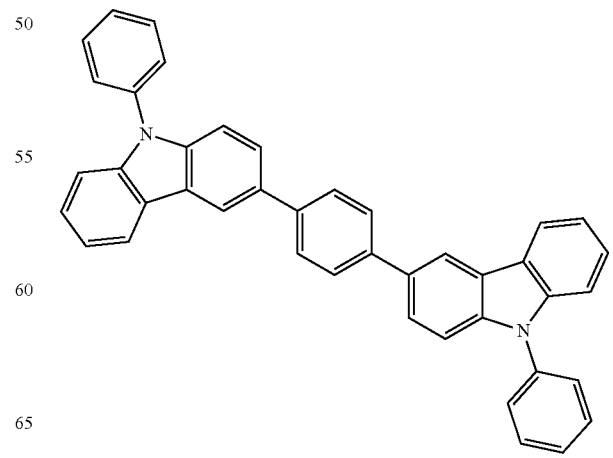

[B-103]
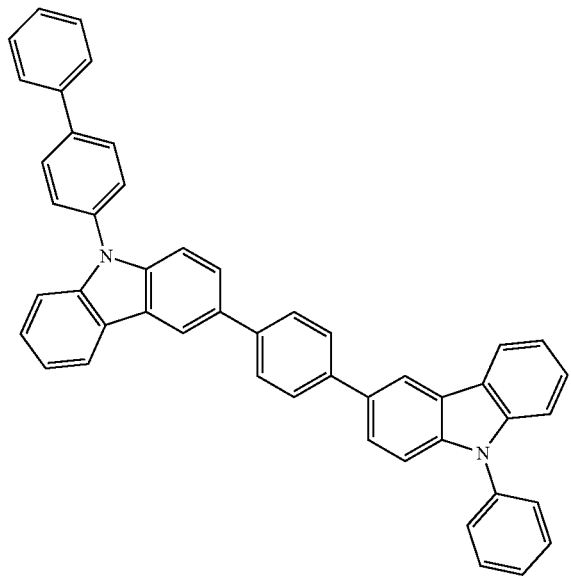
[B-106]
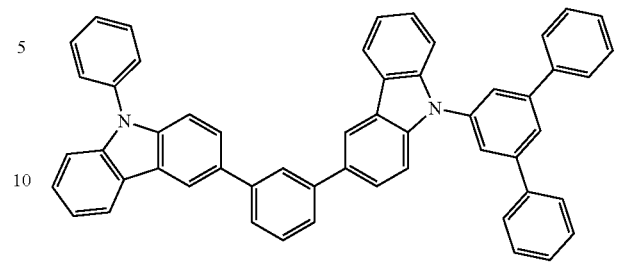
[B-107]
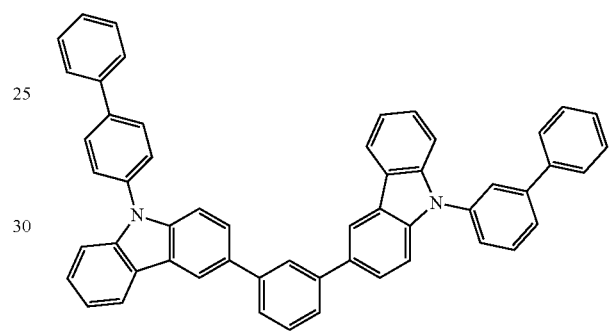
[B-104]
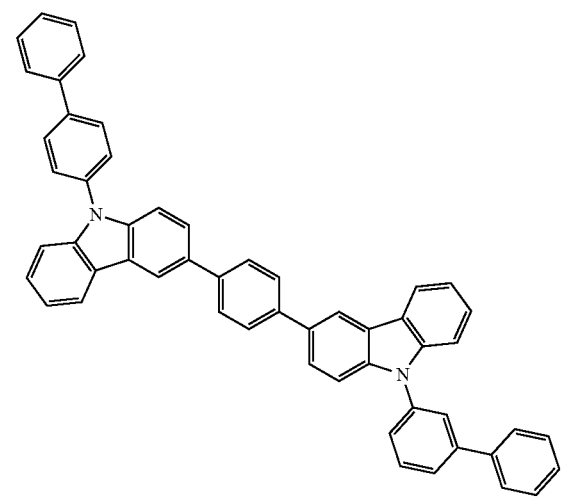
[B-108]
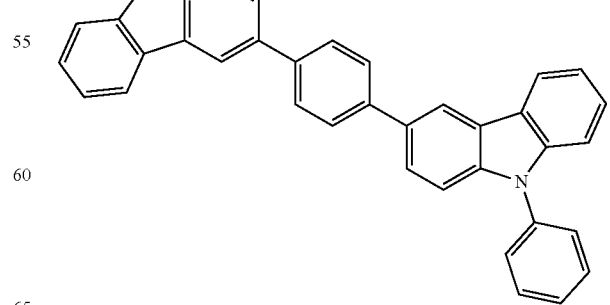
[B-105]
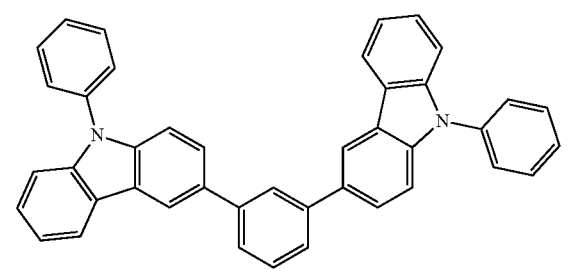

[B-109]
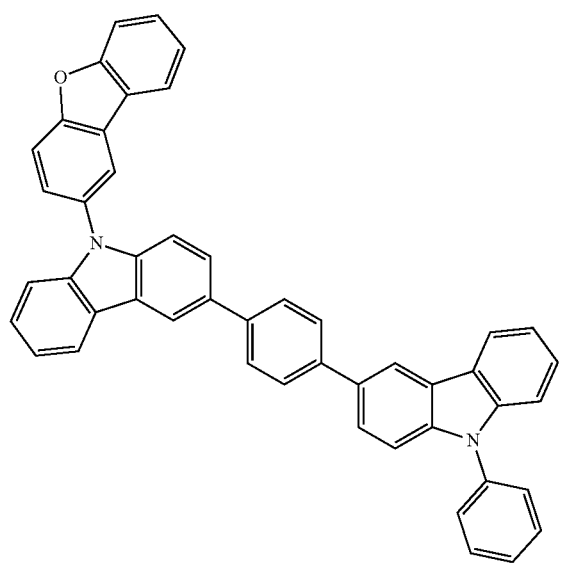
[B-110]
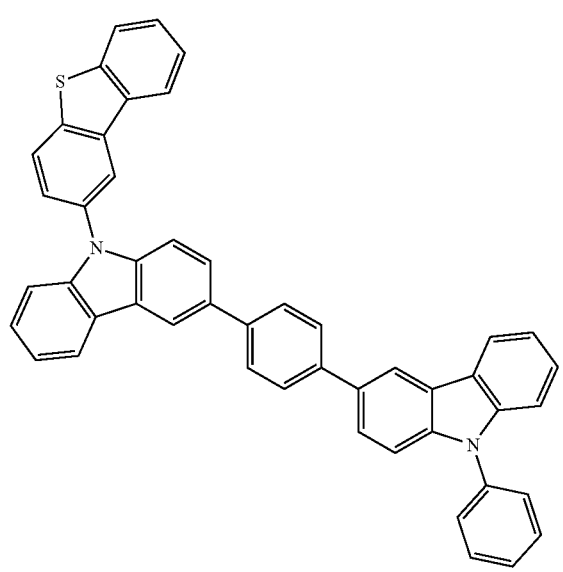
[B-111]
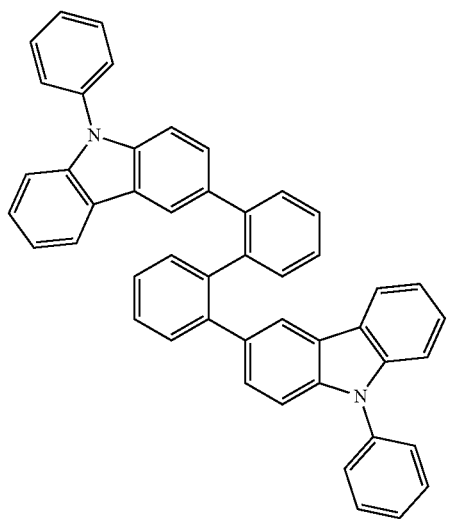
[B-112]
[B-113]
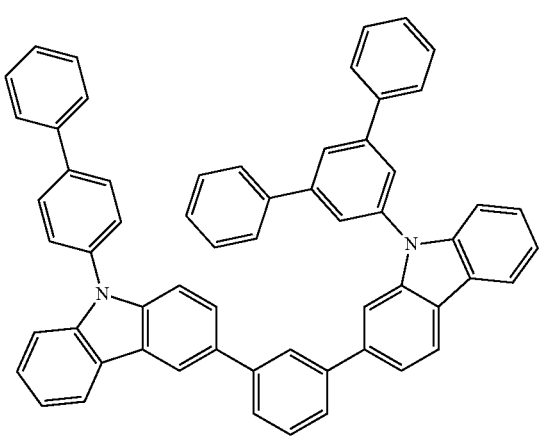

[B-114]
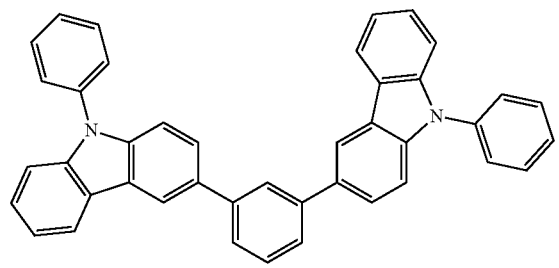
[B115]
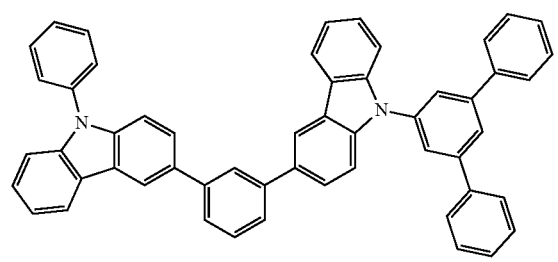
[B-116]
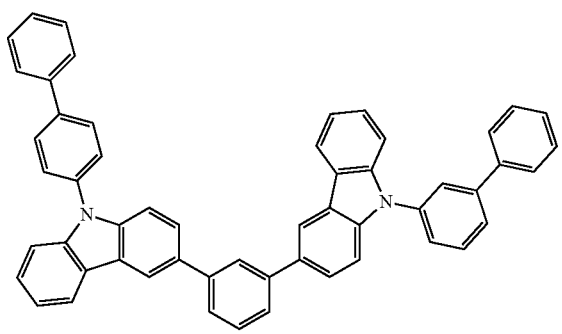
[B-117]
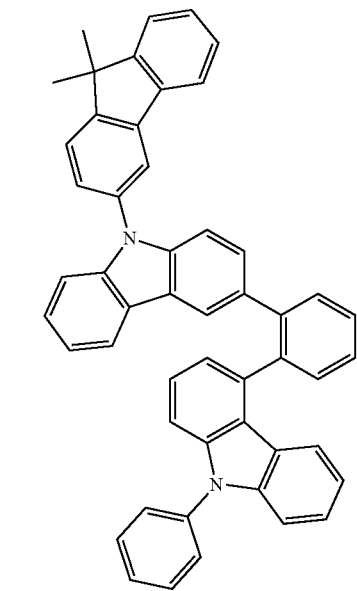
[B-118]
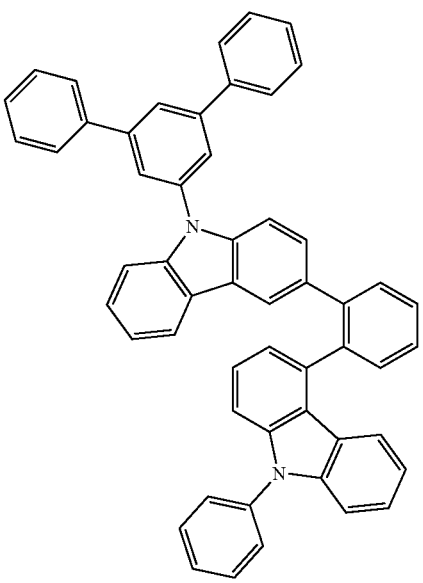
[B-119]
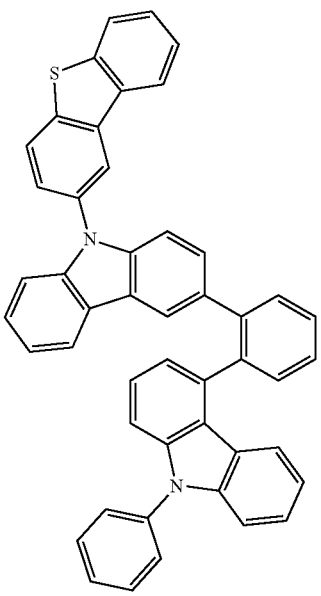

[B-120]
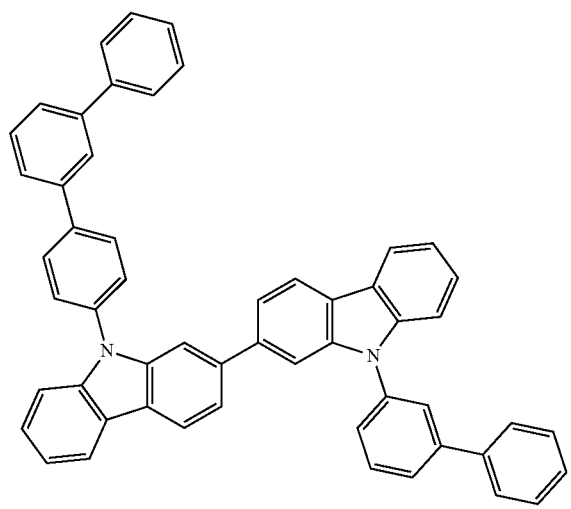
[B-123]
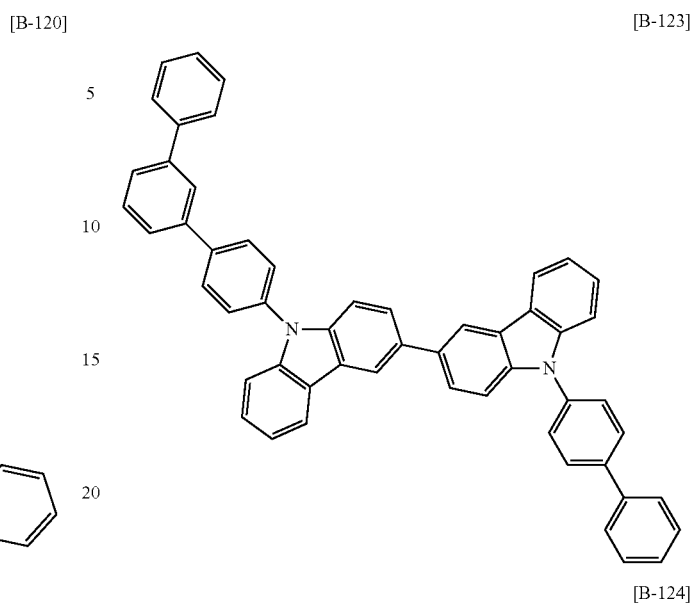
[B-121]
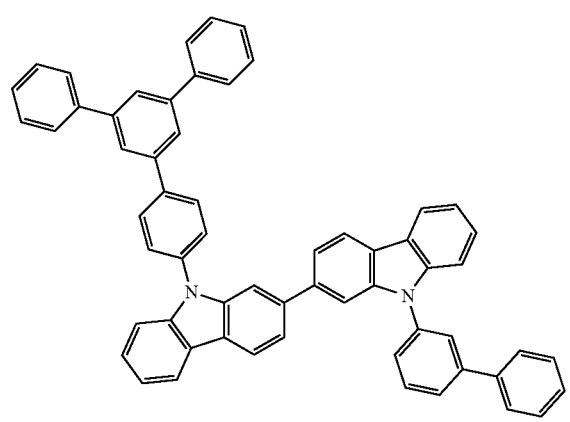
[B-124]
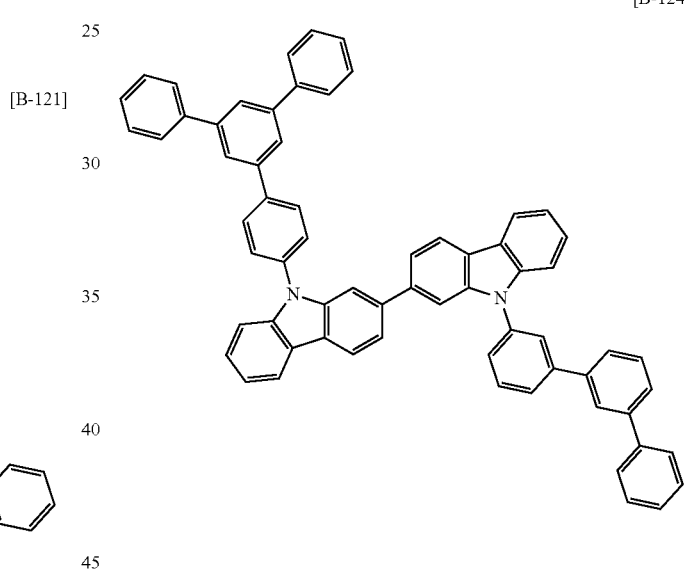
[B-122]
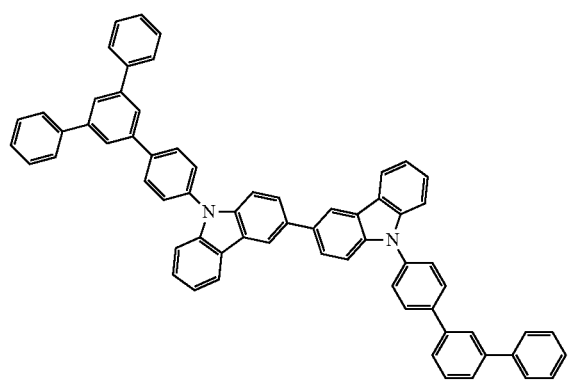
[B-125]
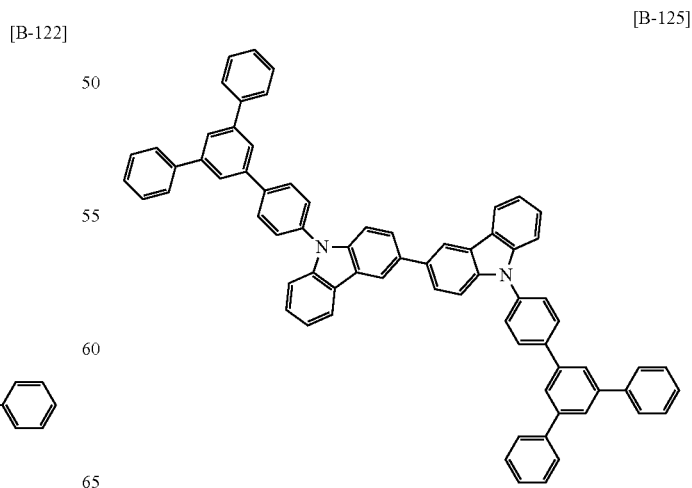

[B-126]
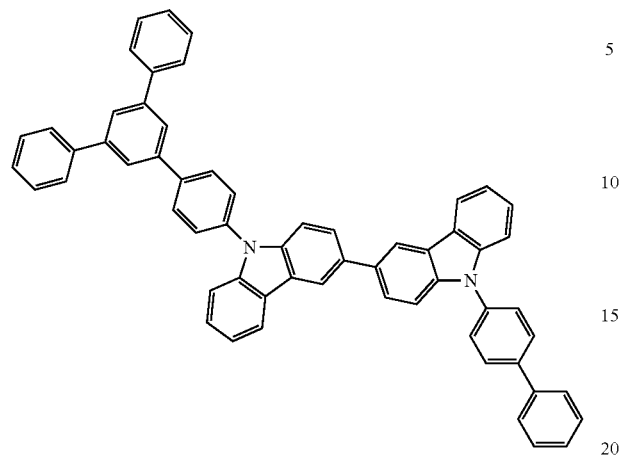
[B-127]
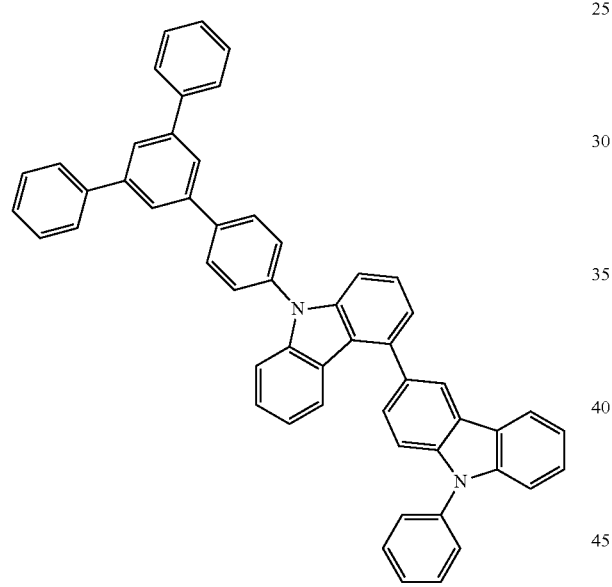
[B-128]
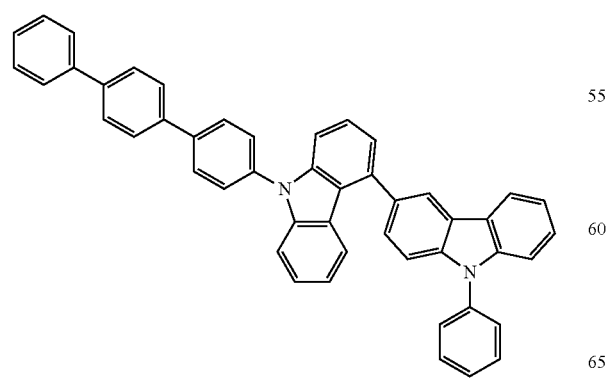
[B-129]
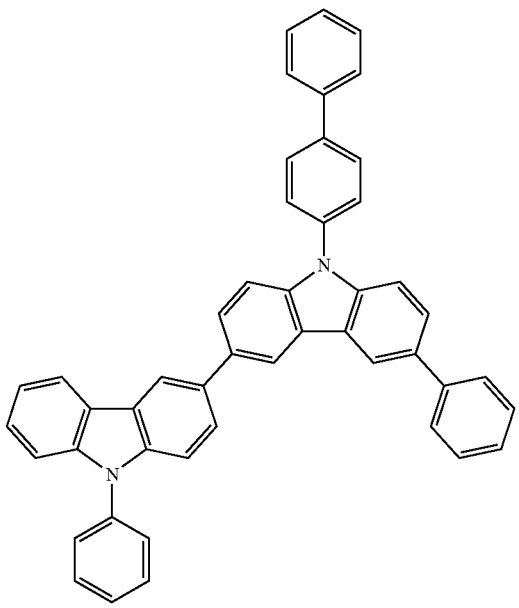
[B-130]
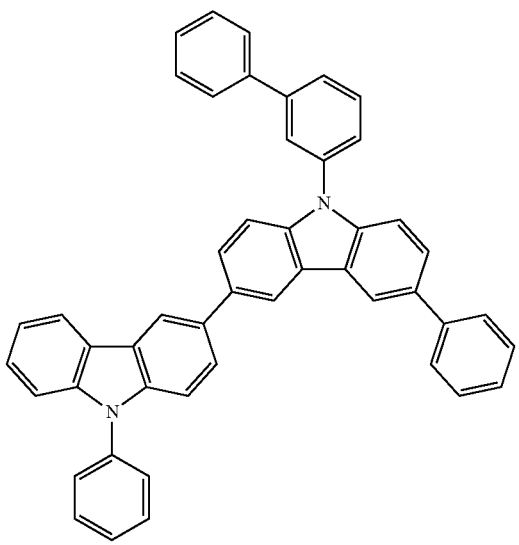

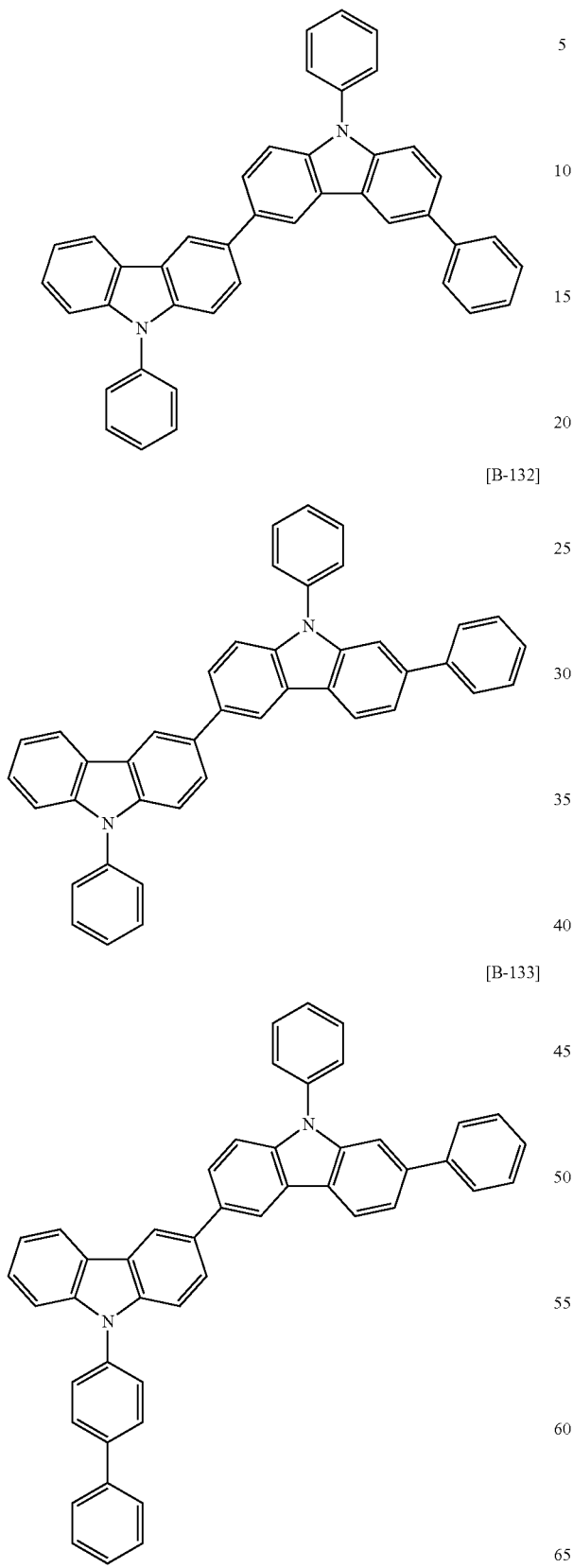
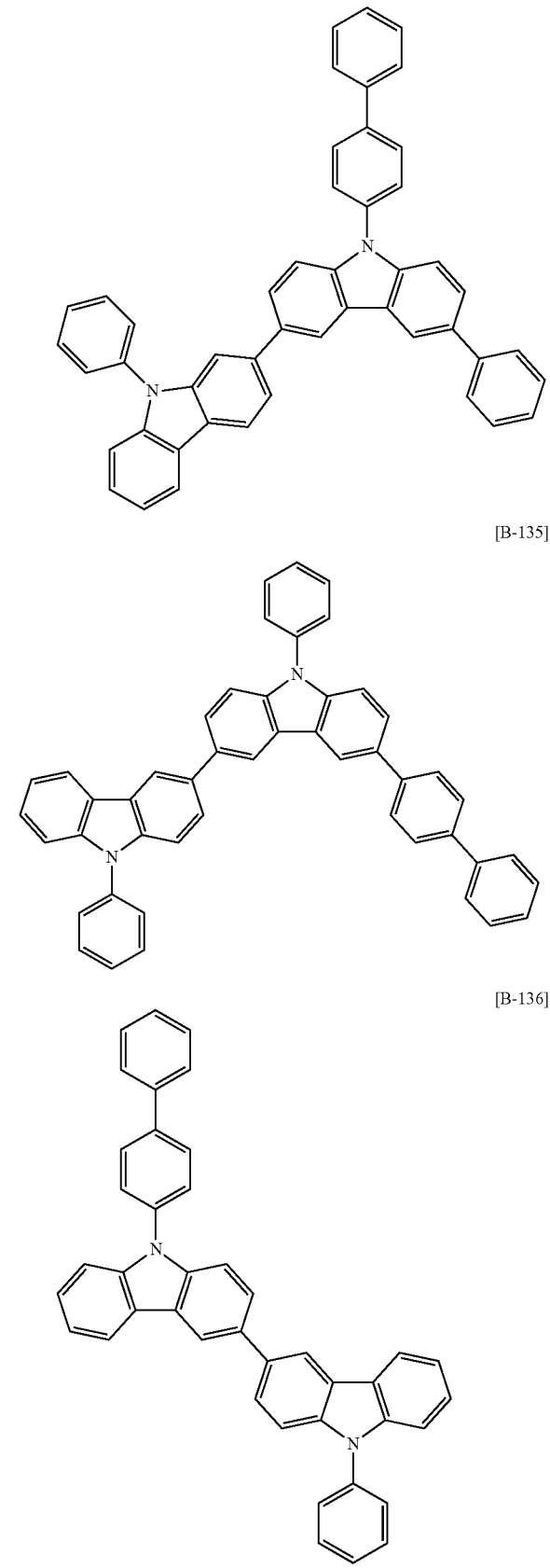

[B-137]

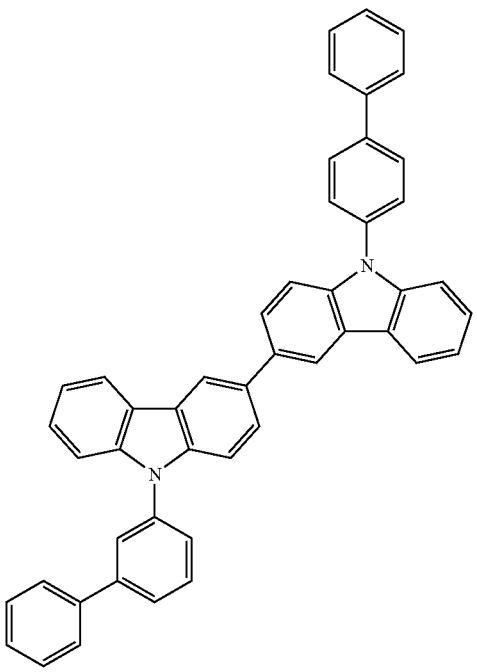

[B-138]

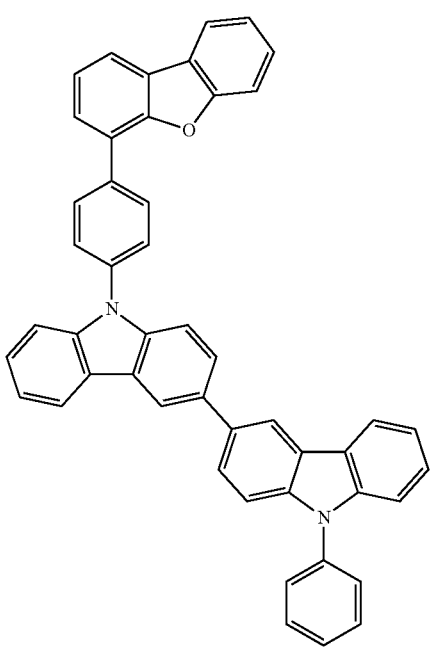

[B-139]

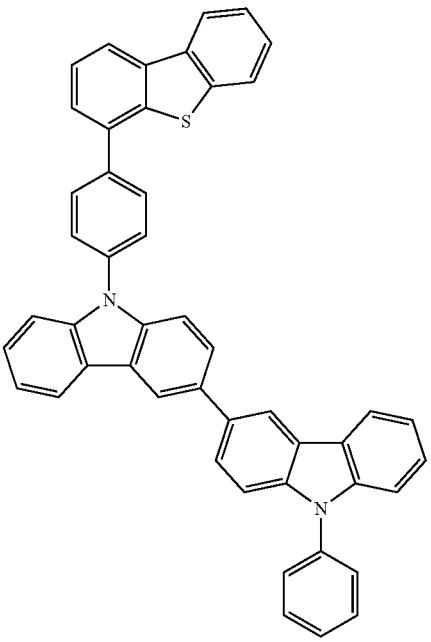

The second compound for an organic optoelectronic device is used with the first compound for an organic optoelectronic device in a light-emitting layer and thus charge mobility and stability are increased and thus luminous efficiency and life-span characteristics are improved. Charge mobility may be controlled by adjusting a ratio of the second compound for an organic optoelectronic device and the first compound for an organic optoelectronic device.

In addition, the first compound for an organic optoelectronic device and the second compound for an organic optoelectronic device may be for example included in a weight ratio of about 1:9 to 9:1, and specifically about 2:8 to 8:2, about 3:7 to 7:3, about 4:6 to 6:4, and about 5:5. Within the ranges, efficiency and life-span may be improved simultaneously.

As an example of the composition for an organic optoelectronic device, a first host represented by Chemical Formula 1-a1 or 1-c1 and a second lost represented by C-8 of Group III may be included.

For example, *—$Y^1$—$Ar^3$ and *—$Y^2$—$Ar^4$ of Chemical Formula 2 may be selected from B-1, B-2, B-3, B-18, and B-25 of Group IV.

The composition may further include one or more organic compound in addition to the first compound for an organic optoelectronic device and the second compound for an organic optoelectronic device.

The compound for an organic optoelectronic device may further include a dopant. The dopant may be a red, green, or blue dopant.

The dopant is a material in small amount to cause light emission and may be generally a material such as a metal complex that emits light by multiple excitation into a triplet or more. The dopant may be, for example an inorganic, organic, or organic/inorganic compound, and one or more kinds thereof may be used.

One example of the dopant may be a phosphorescent dopant, examples of the phosphorescent dopant may be an organometal compound including Ir, Pt, Os, Ti, Zr, Hf, Eu, Tb, Tm, Fe, Co, Ni, Ru, Rh, Pd, or a combination thereof.

The phosphorescent dopant may be, for example a compound represented by Chemical Formula Z, but is not limited thereto.

$$L_2MX \quad \text{[Chemical Formula Z]}$$

In Chemical Formula Z, M is a metal, and L and X are the same or different, and are a ligand to form a complex compound with M.

The M may be, for example, Ir, Pt, Os, Ti, Zr, Hf, Eu, Tb, Tm, Fe, Co, Ni, Ru, Rh, Pd, or a combination thereof and L and X may be, for example a bidendate ligand.

Hereinafter, an organic optoelectronic device including the compound for an organic optoelectronic device or the composition for an organic optoelectronic device is described.

An organic optoelectronic device according to another embodiment includes an anode and a cathode facing each other and at least one organic layer disposed between the anode and the cathode, wherein the organic layer includes the compound for an organic optoelectronic device or the composition for an organic optoelectronic device.

For example, the organic layer may include a light-emitting layer and the light-emitting layer may include the compound for an organic optoelectronic device or the composition for an organic optoelectronic device.

Specifically, the compound for an organic optoelectronic device or the composition for an organic optoelectronic device may be included as a blue host of the light-emitting layer.

In addition, the organic layer includes a light-emitting layer and at least one auxiliary layer selected from a hole injection layer, a hole transport layer, an electron blocking layer, an electron transport layer, an electron injection layer, and a hole blocking layer and the auxiliary layer may include the compound for an organic optoelectronic device or the composition for an organic optoelectronic device.

The auxiliary layer may further include an electron transport auxiliary layer that is adjacent to the light-emitting layer and the electron transport auxiliary layer may include the compound for an organic optoelectronic device, or the composition for an organic optoelectronic device.

The organic optoelectronic device may be any device to convert electrical energy into photoenergy and vice versa without particular limitation, and may be, for example an organic photoelectric diode, an organic light emitting diode, an organic solar cell, and an organic photo conductor drum.

Herein, an organic light emitting diode as one example of an organic optoelectronic device is described referring to drawings.

FIGS. 1 and 2 are cross-sectional views showing organic light emitting diodes according to embodiments.

Referring to FIG. 1, an organic light emitting diode 100 according to an embodiment includes an anode 120 and a cathode 110 facing each other and an organic layer 105 between the anode 120 and the cathode 110.

The anode 120 may be made of a conductor having a large work function to help hole injection, and may be for example a metal, a metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example a metal, a metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al and $BaF_2$/Ca, but is not limited thereto.

The organic layer 105 includes a light-emitting layer 130 including the compound for an organic optoelectronic device.

FIG. 2 is a cross-sectional view showing an organic light emitting diode according to another embodiment.

Referring to FIG. 2, an organic light emitting diode 200 further includes a hole auxiliary layer 140 in addition to the light-emitting layer 130. The hole auxiliary layer 140 may further increase hole injection and/or hole mobility and block electrons between the anode 120 and the light-emitting layer 130. The hole auxiliary layer 140 may be, for example a hole transport layer, a hole injection layer, and/or an electron blocking layer, and may include at least one layer.

The organic layer 105 of FIG. 1 or 2 may further include an electron injection layer, an electron transport layer, an electron transport auxiliary layer, a hole transport layer, a hole transport auxiliary layer, a hole injection layer, or a combination thereof even if they are not shown. The compound for an organic optoelectronic device of the present invention may be included in these organic layers. The organic light emitting diodes 100 and 200 may be manufactured by forming an anode or a cathode on a substrate, forming an organic layer using a dry film formation method such as a vacuum deposition method (evaporation), sputtering, plasma plating, and ion plating or a wet coating method such as spin coating, dipping, and flow coating, and forming a cathode or an anode thereon.

The organic light emitting diode may be applied to an organic light emitting diode display.

Hereinafter, the embodiments are illustrated in more detail with reference to examples. These examples, however, are not in any sense to be interpreted as limiting the scope of the invention Hereinafter, starting materials and reactants used in Examples and Synthesis Examples were purchased from Sigma-Aldrich Co. Ltd. or TCI Inc. as far as there in no particular comment or were synthesized by known methods. (Preparation of Compound for Organic Optoelectronic Device)

The compound as one specific examples of the present invention was synthesized through the following steps.

First Compound for Organic Optoelectronic Device

Synthesis Example 1: Synthesis of Intermediate I-1

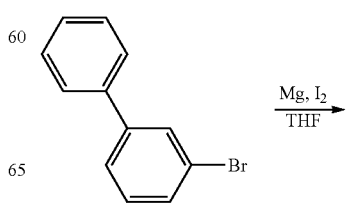

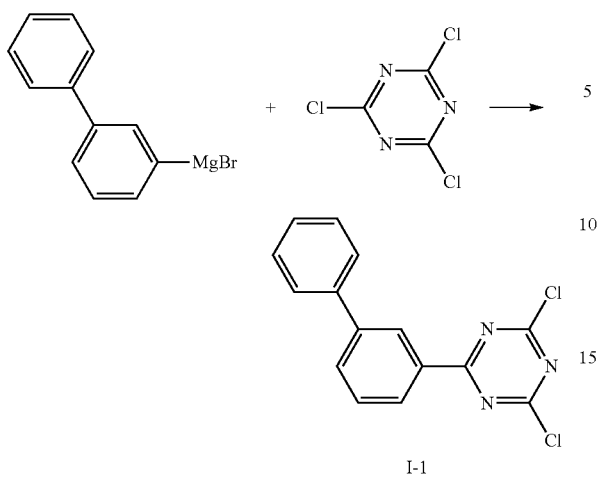

Magnesium (10.4 g, 429 mmol) and iodine (2.18 g, 8.58 mmol) were added to tetrahydrofuran (THF, 0.1 L) under a nitrogen environment and stirred therewith for 30 minutes, and 3-bromobiphenyl (100 g, 429 mmol) dissolved in THF (0.1 L) was slowly added thereto in a dropwise fashion at 0° C. for 30 minutes. The mixed solution was slowly added in a dropwise fashion to cyanuric chloride (94.9 g, 515 mmol) dissolved in THF (1.0 L) at 0° C. for 30 minutes. After the reaction was complete, water was added to the reaction solution, the mixture was extracted with dichloromethane (DCM) and treated with anhydrous MgSO4 to remove moisture, and the resultant was filtered and concentrated under a reduced pressure. A residue obtained in this way was separated and purified through flash column chromatography to obtain Intermediate I-1 (90.7 g, 70%).

HRMS (70 eV, EI+): m/z calcd for C15H9Cl2N3: 301.0174, found: 301.

Elemental Analysis: C, 60%; H, 3%

Synthesis Example 2: Synthesis of Intermediate I-2

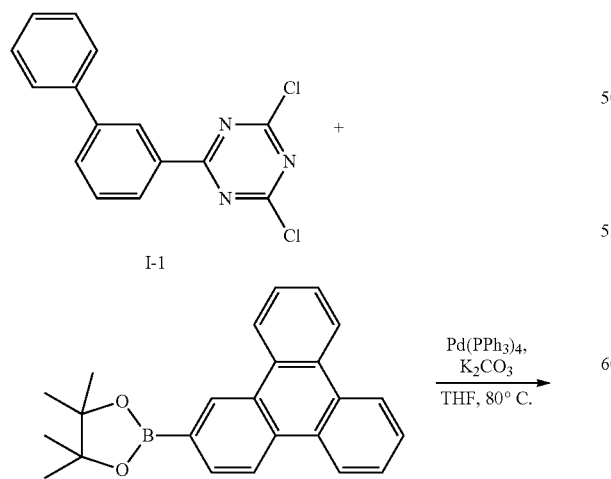

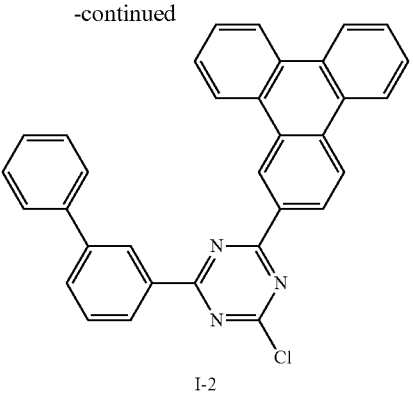

I-2

Intermediate I-1 (85 g, 281 mmol) was dissolved in tetrahydrofuran (THF, 0.9 L) under a nitrogen environment, 4,4,5,5-tetramethyl-2-(triphenylen-2-yl)-1,3,2-dioxaborolane (99.7 g, 281 mmol, purchased from P&H Tech Co., Ltd. (http://www.phtech.co.kr/)), tetrakis(triphenylphosphine) palladium (3.25 g, 2.81 mmol), and potassium carbonate saturated in water (97.1 g, 703 mmol) were added thereto, and the mixture was heated and refluxed at 80° C. for 12 hours. After the reaction was complete, water was added to the reaction solution, the mixture was extracted with dichloromethane (DCM) and treated with anhydrous MgSO4 to remove moisture, and the resultant was filtered and concentrated under a reduced pressure. A residue obtained in this way was separated and purified through flash column chromatography to obtain Intermediate I-2 (84.7 g, 61%).

HRMS (70 eV, EI+): m/z calcd for C33H20ClN3: 493.1346, found: 493.

Elemental Analysis: C, 80%; H, 4%

Synthesis Example 3: Synthesis of Intermediate I-3

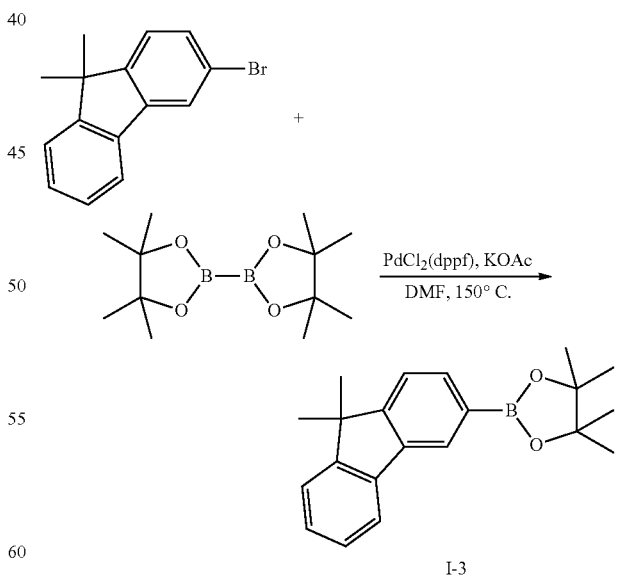

3-bromo-9,9-dimethylfluorene (100 g, 366 mmol, purchased from Zengzhon HQ Material Co., Ltd. (http://www.hqmat.com/)) was dissolved in dimethylforamide (DMF, 1.0 L) under a nitrogen environment, bis(pinacolato)diboron (112 g, 439 mmol) and (1,1'-bis(diphenylphosphine)ferrocene)dichloropalladium (II) (2.99 g, 3.66 mmol), and potassium acetate (108 g, 1,098 mmol) were added thereto, and the mixture was heated and refluxed at 150° C. for 5 hours. When a reaction was complete, water was added to the reaction solution, and the mixture was filtered and dried in a vacuum oven. A residue obtained in this way was separated and purified through flash column chromatography to obtain Intermediate I-3 (99.6 g, 85%).

HRMS (70 eV, EI+): m/z calcd for C21H25BO2: 320.1948, found: 320.

Elemental Analysis: C, 79%; H, 8%

Synthesis Example 4: Synthesis of Intermediate I-4

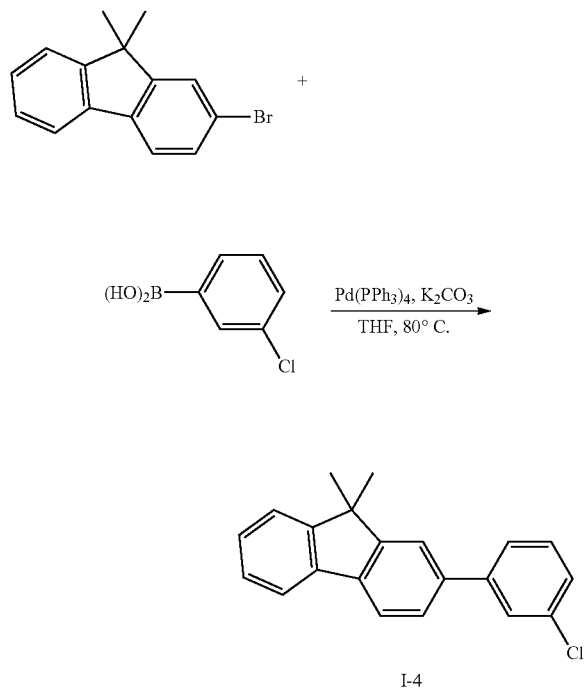

2-bromo-9,9-dimethylfluorene (100 g, 366 mmol, purchased from Sigma Aldrich (http://www.sigmaaldrich.com/)) was dissolved in tetrahydrofuran (THF, 0.8 L) under a nitrogen environment, 3-chlorophenylboronic acid (63.0 g, 403 mmol, purchased from Tokyo Chemical Industry Co., Ltd. (http://www.tcichemicals.com/)), tetrakis(triphenylphosphine)palladium (4.23 g, 3.66 mmol), and potassium carbonate saturated in water (126 g, 915 mmol) were added thereto, and the mixture was heated and refluxed at 80° C. for 8 hours. After the reaction was complete, water was added to the reaction solution, the mixture was extracted with dichloromethane (DCM) and treated with anhydrous MgSO4 to remove moisture, and the resultant was filtered and concentrated under a reduced pressure. A residue obtained in this way was separated and purified through flash column chromatography to obtain Intermediate I-4 (104 g, 93%).

HRMS (70 eV, EI+): m/z calcd for C21H17Cl: 304.1019, found: 304.

Elemental Analysis: C, 83%; 1-1, 6%

Synthesis Example 5: Synthesis of Intermediate I-5

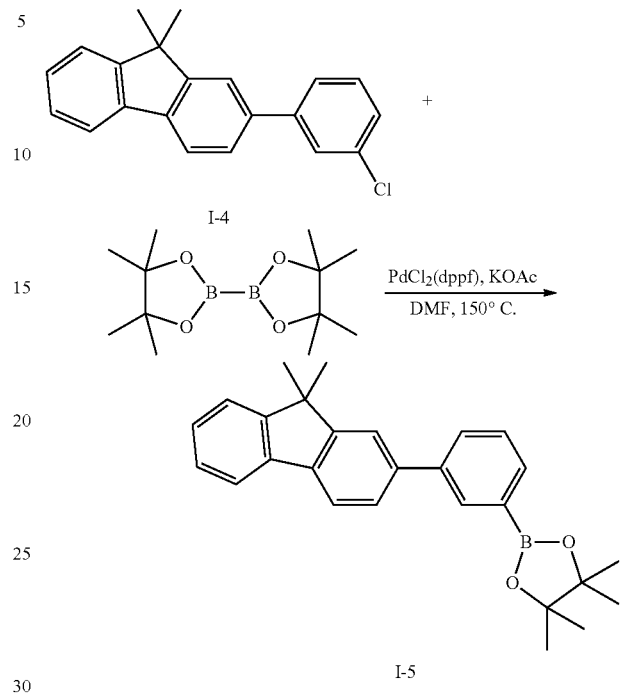

Intermediate I-4 (100 g, 328 mmol) was dissolved in dimethylforamide (DMF, 1.0 L) under a nitrogen environment, bis(pinacolato)diboron (100 g, 394 mmol), (1,1'-bis(diphenylphosphine)ferrocene)dichloropalladium (II) (2.68 g, 3.28 mmol), and potassium acetate (96.6 g, 984 mmol) were added thereto, and the mixture was heated and refluxed at 150° C. for 20 hours. When a reaction was complete, water was added to the reaction solution, and the mixture was filtered and dried in a vacuum oven. A residue obtained therefrom was separated and purified through flash column chromatography to obtain Intermediate I-5 (92.3 g, 71%).

HRMS (70 eV, EI+): m/z calcd for C27H29BO2: 396.2261, found: 396.

Elemental Analysis: C, 82%; H, 7%

Synthesis Example 6: Synthesis of Intermediate I-6

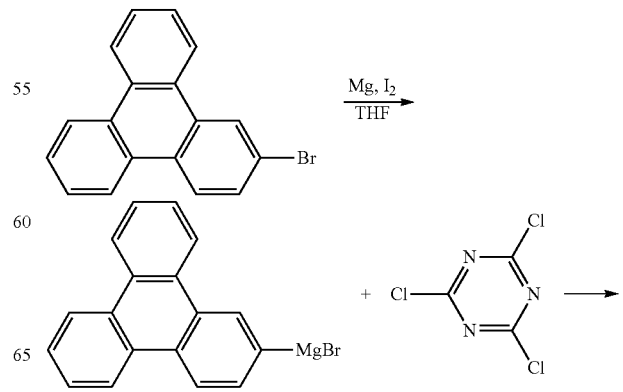

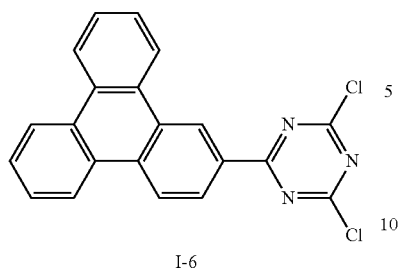

I-6

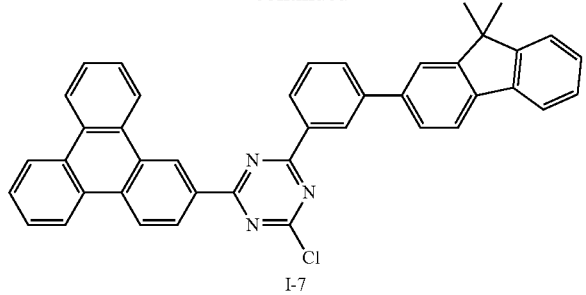

I-7

Magnesium (7.91 g, 326 mmol) and iodine (1.65 g, 6.52 mmol) were added to tetrahydrofuran (THF, 0.1 L) under a nitrogen environment and stirred therewith for 30 minutes, and 2-bromotriphenylene (100 g, 326 mmol, purchased from P&H Tech Co., Ltd. (http://www.phtech.co.kr/)) dissolved in THF (0.1 L) was slowly added thereto in a dropwise fashion at 0° C. for 30 minutes. This mixed solution was slowly added in a dropwise fashion to cyanuric chloride (72.1 g, 391 mmol) dissolved in THF (0.8 L) at 0° C. for 30 minutes. After the reaction was complete, water was added to the reaction solution, the mixture was extracted with dichloromethane (DCM) and treated with anhydrous MgSO4 to remove moisture, and the resultant was filtered and concentrated under a reduced pressure. A residue obtained in this way was separated and purified through flash column chromatography to obtain Intermediate I-6 (77.3 g, 63%).

HRMS (70 eV, EI+): m/z calcd for C21H11Cl2N3: 375.0330, found: 375.

Elemental Analysis: C, 67%; H, 3%

Synthesis Example 7: Synthesis of Intermediate I-7

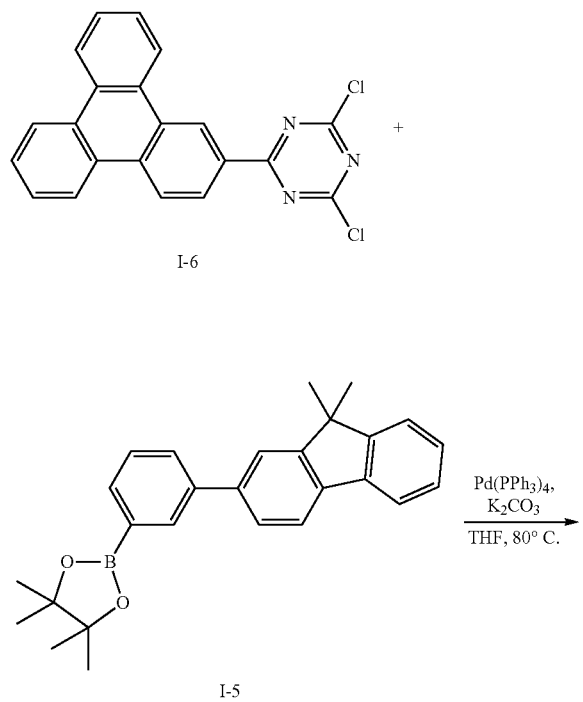

Intermediate I-6 (75 g, 199 mmol) was dissolved in tetrahydrofuran (THF, 0.8 L) under a nitrogen environment, Intermediate I-5 (79.0 g, 199 mmol), tetrakis(triphenylphosphine)palladium (2.30 g, 1.99 mmol), and potassium carbonate saturated in water (68.8 g, 498 mmol) were added thereto, and the mixture was heated and refluxed at 80° C. for 14 hours. After the reaction was complete, water was added to the reaction solution, the mixture was extracted with dichloromethane (DCM) and treated with anhydrous MgSO4 to remove moisture, and the resultant was filtered and concentrated under a reduced pressure. A residue obtained in this way was separated and purified through flash column chromatography to obtain Intermediate I-7 (80.1 g, 66%).

HRMS (70 eV, EI+): m/z calcd for C42H28ClN3: 609.1972, found: 609.

Elemental Analysis: C, 83%; H, 5%

Synthesis Example 8: Synthesis of Intermediate I-8

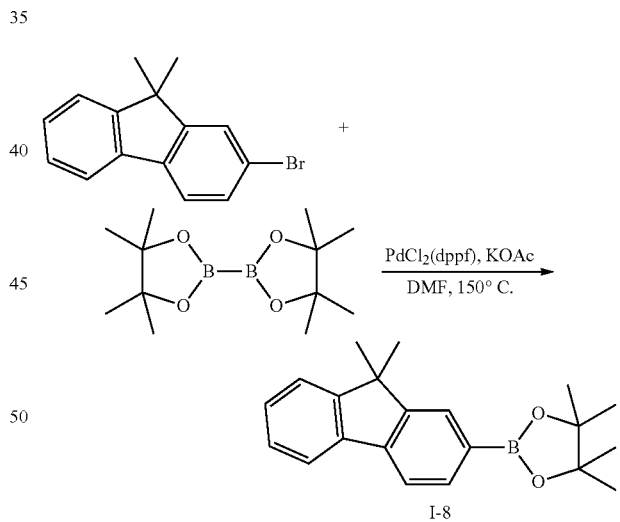

I-8

2-bromo-9,9-dimethylfluorene (100 g, 366 mmol, purchased from Sigma Aldrich Co., Ltd.) was dissolved in dimethylforamide (DMF, 1.1 L) under a nitrogen environment, bis(pinacolato)diboron (112 g, 439 mmol), (1,1'-bis(diphenylphosphine)ferrocene)dichloropalladium (II) (2.99 g, 3.66 mmol), and potassium acetate (108 g, 1,098 mmol) were added thereto, and the mixture was heated and refluxed at 150° C. for 5 hours. When a reaction was complete, water was added to the reaction solution, and the mixture was filtered and dried in a vacuum oven. A residue obtained in this way was separated and purified through flash column chromatography to obtain Intermediate I-8 (102 g, 87%).

HRMS (70 eV, EI+): m/z calcd for C21H25BO2: 320.1948, found: 320.

Elemental Analysis: C, 79%; H, 8%

Synthesis Example 9: Synthesis of Compound 1

Synthesis Example 10: Synthesis of Compound 2

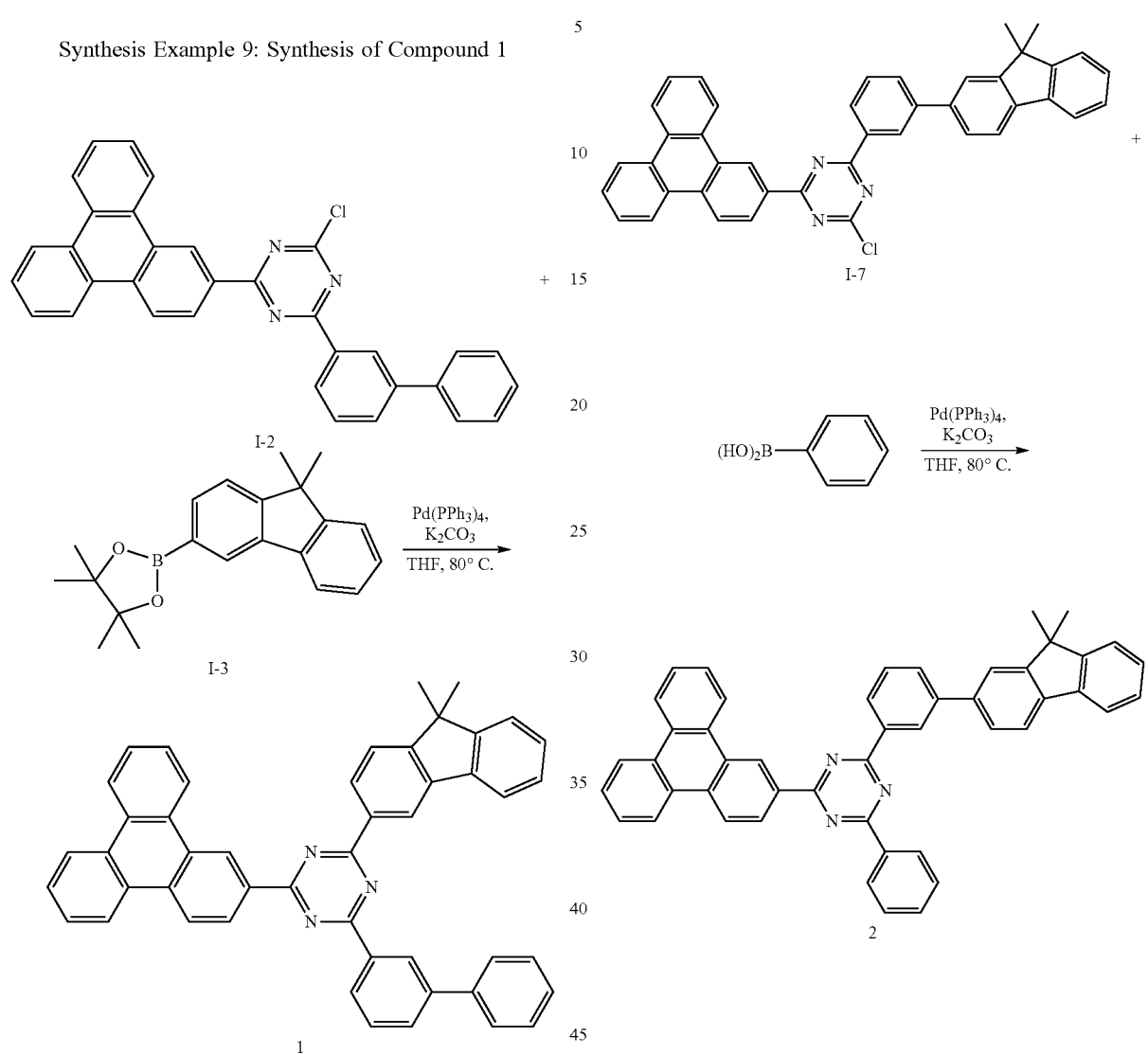

Intermediate I-2 (10 g, 20.2 mmol) was dissolved in tetrahydrofuran (THF, 0.1 L) under a nitrogen environment, Intermediate I-3 (7.13 g, 22.3 mmol), tetrakis(triphenylphosphine)palladium (0.23 g, 0.20 mmol), and potassium carbonate saturated in water (6.98 g, 50.5 mmol) were added thereto, and the mixture was heated and refluxed at 80° C. for 18 hours. After the reaction was complete, water was added to the reaction solution, the mixture was extracted with dichloromethane (DCM) and treated with anhydrous MgSO4 to remove moisture, and the resultant was filtered and concentrated under a reduced pressure. A residue obtained in this way was separated and purified through flash column chromatography to obtain Compound 1 (11.7 g, 89%).

HRMS (70 eV, EI+): m/z calcd for C48H33N3: 651.2674, found: 651.

Elemental Analysis: C, 88%; H, 5%

Intermediate I-7 (10 g, 16.4 mmol) was dissolved in tetrahydrofuran (THF, 0.1 L) under a nitrogen environment, phenylboronic acid (2.0 g, 16.4 mmol, purchased from Tokyo Chemical Industry Co., Ltd.), tetrakis(triphenylphosphine)palladium (0.18 g, 0.16 mmol), and potassium carbonate saturated in water (5.67 g, 41.0 mmol) were added thereto, and the mixture was heated and refluxed at 80° C. for 18 hours. After the reaction was complete, water was added to the reaction solution, the mixture was extracted with dichloromethane (DCM) and treated with anhydrous MgSO4 to remove moisture, and the resultant was filtered and concentrated under a reduced pressure. A residue obtained therefrom was separated and purified through flash column chromatography to obtain Compound 2 (10.2 g, 95%).

HRMS (70 eV, EI+): m/z calcd for C48H33N3: 651.2674, found: 651.

Elemental Analysis: C, 88%; H, 5%

Synthesis Example 11: Synthesis of Compound 6

Synthesis Example 12: Synthesis of Compound 7

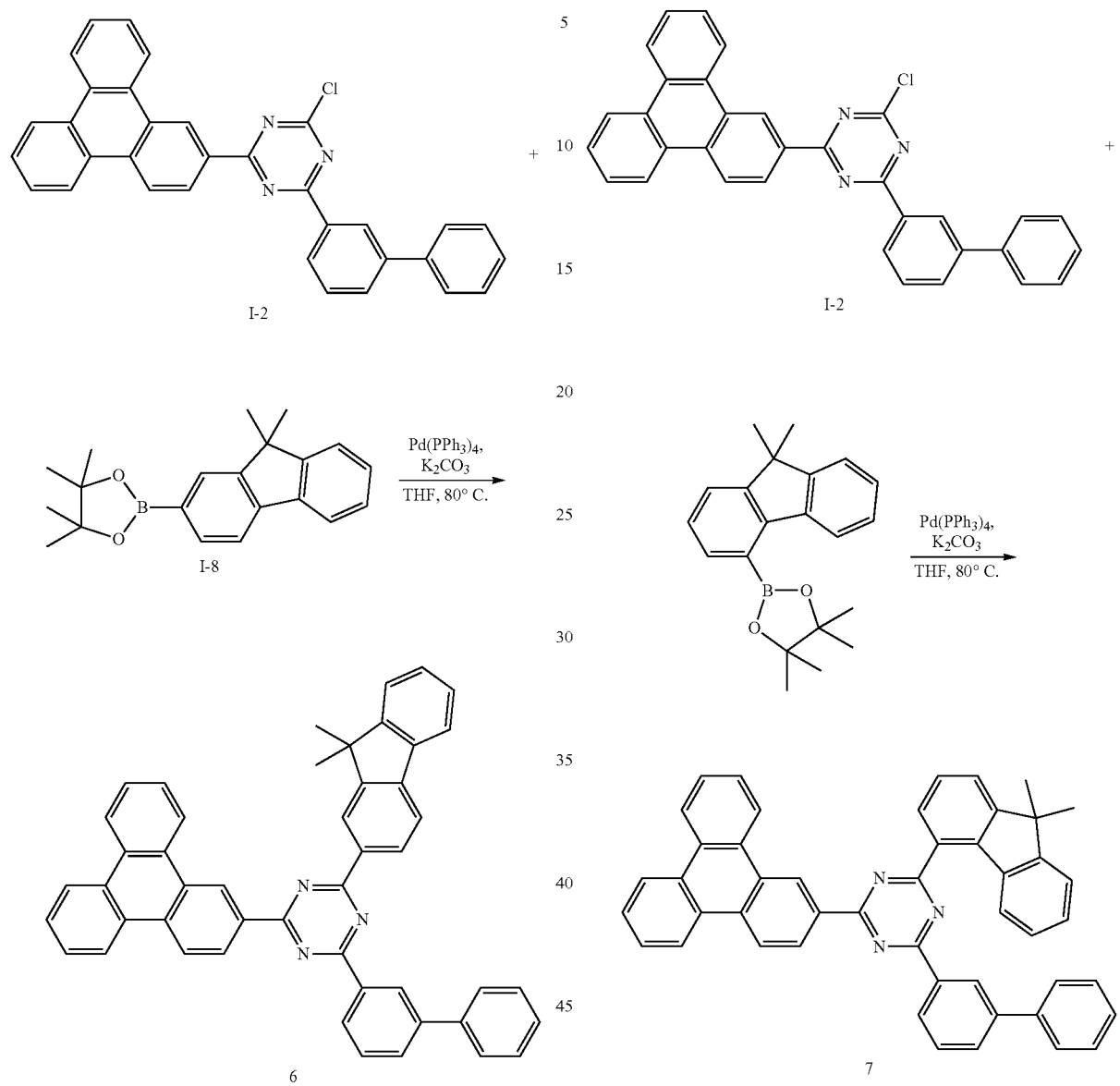

Intermediate I-2 (10 g, 20.2 mmol) was dissolved in tetrahydrofuran (THF, 0.1 L), Intermediate I-8 (7.13 g, 22.3 mmol), tetrakis(triphenylphosphine)palladium (0.23 g, 0.20 mmol), and potassium carbonate saturated in water (6.98 g, 50.5 mmol) were added thereto, and the mixture was heated and refluxed at 80° C. for 18 hours. After the reaction was complete, water was added to the reaction solution, the mixture was extracted with dichloromethane (DCM) and treated with anhydrous MgSO$_4$ to remove moisture, and the resultant was filtered and concentrated under a reduced pressure. A residue obtained in this way was separated and purified through flash column chromatography to obtain Compound 6 (11.8 g, 90%).

HRMS (70 eV, EI+): m/z calcd for C48H33N3: 651.2674, found: 651.

Elemental Analysis: C, 88%; H, 5%

Intermediate I-2 (10 g, 20.2 mmol) was dissolved in tetrahydrofuran (THF, 0.1 L) under a nitrogen environment, 4-(9,9-dimethyl-9H-fluoren-4-yl)-4,4,5,5-tetramethyl-1,3,2-dioxaborolane (7.13 g, 22.3 mmol, purchased from Zhengzhon HQ Material), tetrakis(triphenylphosphine)palladium (0.23 g, 0.20 mmol), and potassium carbonate saturated in water (6.98 g, 50.5 mmol) were added thereto, and the mixture was heated and refluxed at 80° C. for 18 hours. After the reaction was complete, water was added to the reaction solution, the mixture was extracted with dichloromethane (DCM) and treated with anhydrous MgSO$_4$ to remove moisture, and the resultant was filtered and concentrated under a reduced pressure. A residue obtained in this way was separated and purified through flash column chromatography to obtain Compound 7 (7.64 g, 58%).

HRMS (70 eV, EI+): m/z calcd for C48H33N3: 651.2674, found: 651.

Elemental Analysis: C, 88%; H, 5%

Synthesis Example 13: Synthesis of Compound 25

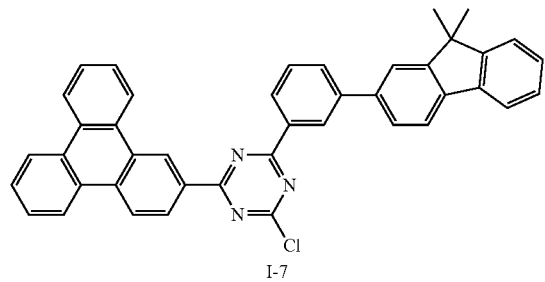

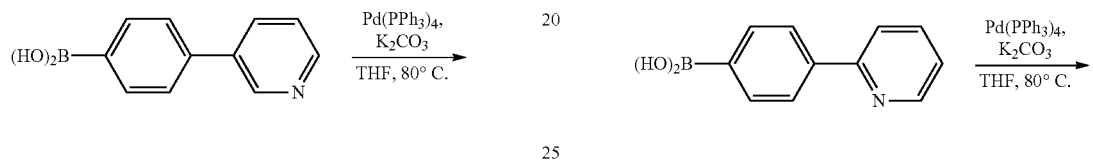

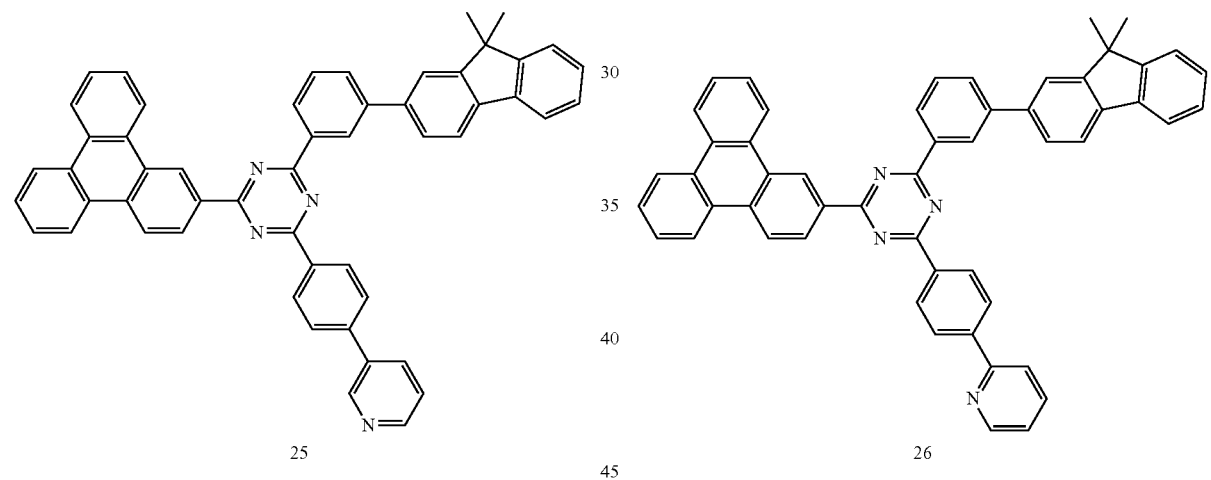

Intermediate I-7 (10 g, 16.4 mmol) was dissolved in tetrahydrofuran (THF, 0.1 L) under a nitrogen environment, 4-(pyridin-3-yl)phenylboronic acid (3.26 g, 16.4 mmol, purchased from Changsha Luxing Bio-chem Tech Co., Ltd. (http://www.luxingbc.com/)), tetrakis(triphenylphosphine) palladium (0.18 g, 0.16 mmol), and potassium carbonate saturated in water (5.67 g, 41.0 mmol) were added thereto, and the mixture was heated and refluxed at 80° C. for 18 hours. After the reaction was complete, water was added to the reaction solution, the mixture was extracted with dichloromethane (DCM) and treated with anhydrous $MgSO_4$ to remove moisture, and the resultant was filtered and concentrated under a reduced pressure. A residue obtained in this way was separated and purified through flash column chromatography to obtain Compound 25 (8.61 g, 72%).

HRMS (70 eV, EI+): m/z calcd for $C_{53}H_{36}N_4$: 728.2940, found: 728.

Elemental Analysis: C, 87%; H, 5%

Synthesis Example 14: Synthesis of Compound 26

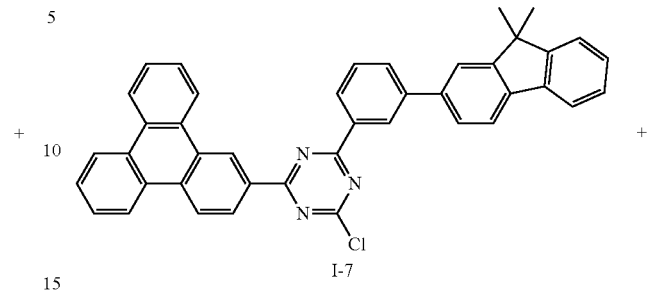

Intermediate I-7 (10 g, 16.4 mmol) was dissolved in tetrahydrofuran (THF, 0.1 L) under a nitrogen environment, 4-(pyridin-2-yl)phenylboronic acid (3.26 g, 16.4 mmol, purchased from Changsha Luxing Bio-chem Tech Co., Ltd. (http://www.luxingbc.com/)), tetrakis(triphenylphosphine) palladium (0.18 g, 0.16 mmol), and potassium carbonate saturated in water (5.67 g, 41.0 mmol) were added thereto, and the mixture was heated and refluxed at 80° C. for 18 hours. After the reaction was complete, water was added to the reaction solution, the mixture was extracted with dichloromethane (DCM) and treated with anhydrous $MgSO_4$ to remove moisture, and the resultant was filtered and concentrated under a reduced pressure. A residue obtained therefrom was separated and purified through flash column chromatography to obtain Compound 26 (8.25 g, 69%).

HRMS (70 eV, EI+): m/z calcd for $C_{53}H_{36}N_4$: 728.2940, found: 728.

Elemental Analysis: C, 87%; H, 5%

Comparative Synthesis Example 1: Synthesis of Compound Host 1

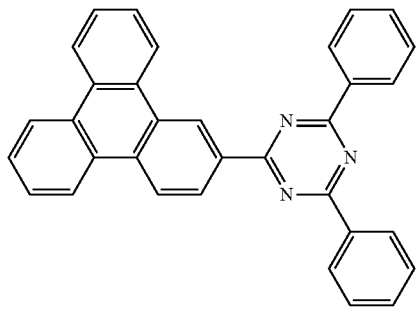

Host 1

Host 1 was synthesized referring to a synthesis method of Patent KR10-1618683.

HRMS (70 eV, EI+): m/z calcd for C33H21N3: 459.1735, found: 459.

Elemental Analysis: C, 86%; H, 5%

Comparative Synthesis Example 2: Synthesis of Compound Host 2

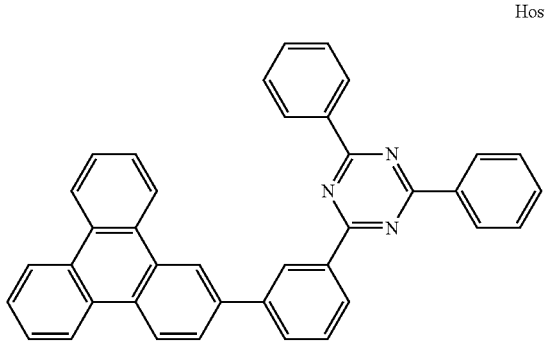

Host 2

Host 2 was synthesized referring to a synthesis method of Patent KR10-1618683.

HRMS (70 eV, EI+): m/z calcd for C39H25N3: 535.2048, found: 535.

Elemental Analysis: C, 87%; H, 5%

Comparative Synthesis Example 3: Synthesis of Compound Host 3

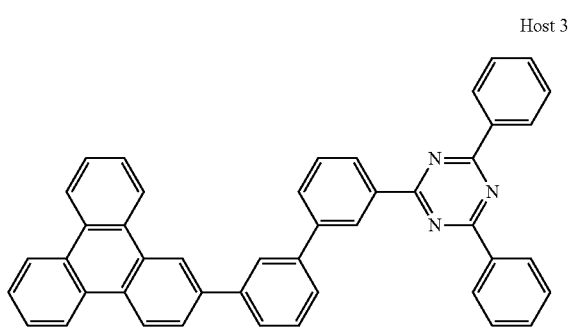 [SMILES: c1ccc(-c2nc(-c3ccccc3)nc(-c3cccc(-c4cccc(-c5ccc6c7ccccc7c7ccccc7c6c5)c4)c3)n2)cc1]

Host 3

Host 3 was synthesized referring to a synthesis method of Patent KR10-1618683.

HRMS (70 eV, EI+): m/z calcd for C45H29N3: 611.2361, found: 611.

Elemental Analysis: C, 88%; H, 5%

Evaluation 1: Confirmation of Glass Transition Temperature Effect (1) Glass Transition Temperature (Tg)

An energy input difference was measured as a function of a temperature by changing temperatures of a sample and a reference with a DSC1 equipment made by Metter Teledo Inc.

(2) Deposition Process Temperature (° C.)

A deposition temperature indicates a temperature at which a host of a light-emitting layer and specifically, a 1 Å-thick light-emitting layer per 1 second (Å/sec) was deposited during manufacture of an organic light emitting diode according to Example 1.

Tg and a deposition process temperature of a compound of the present invention and a comparative compound are shown in Table 1.

TABLE 1

| Compound | Molecular weight (g/mol) | Tg (° C.) | Tg/molecular weight | Deposition process temperature (° C.) | Deposition temperature/molecular weight |
|---|---|---|---|---|---|
| 1 | 651.80 | 135 | 0.21 | 228 | 0.35 |
| 2 | 651.80 | 129 | 0.20 | 223 | 0.34 |
| 6 | 651.80 | 138 | 0.21 | 225 | 0.35 |
| 7 | 651.80 | 136 | 0.21 | 227 | 0.35 |
| 25 | 728.88 | 150 | 0.21 | 235 | 0.32 |
| 26 | 728.88 | 148 | 0.20 | 234 | 0.32 |
| Host 1 | 459.54 | 85 | 0.18 | 212 | 0.46 |
| Host 2 | 535.64 | 95 | 0.18 | 218 | 0.41 |
| Host 3 | 611.73 | 110 | 0.18 | 225 | 0.37 |

As shown in Table 1, the compound of the present invention had high Tg of greater than or equal to 0.2 relative to a molecular weight, while the, comparative compound, Hosts 1 to 3 had low Tg. In general, a material having 0.2 of Tg/molecular weight has very high Tg and thus is not almost crystallized in a device, and accordingly, the compound of the present invention had an excellent effect compared with the comparative compound.

In addition, the compound of the present invention maintained a very low deposition temperature relative to a molecular weight and thus may realize a device having a long life-span compared with the comparative compound.

Manufacture of Organic Light Emitting Diode

Example 1

An organic light emitting diode was manufactured by using Compound 1 of Synthesis Example 9 as a host and Ir(PPy)$_3$ as a dopant.

A 1000 Å-thick ITO was used as an anode, and a 1000 Å-thick aluminum (Al) as a cathode. Specifically, the organic light emitting diode was manufactured in a method of cutting an ITO glass substrate having sheet resistance of 15 Ω/cm$^2$ into a size of 50 mm×50 mm×0.7 mm, ultrasonic wave-cleaning it in acetone, isopropyl alcohol, and pure water respectively for 15 minutes, and UV ozone-cleaning it for 30 minutes.

On the substrate, an 800 Å-thick hole transport layer was formed by depositing N4,N4'-di(naphthalen-1-yl)-N4,N4'- diphenylbiphenyl-4,4'-diamine (NPB) (80 nm) under a vacuum degree of 650×10$^{-7}$ Pa at a deposition rate of 0.1 to 0.3 nm/s. Subsequently, a 300 Å-thick light-emitting layer was formed by using Compound 1 according to Synthesis Example 16 under the same vacuum deposition condition as above, and a phosphorescent dopant, Ir(PPy)$_3$ (CAS Number: 94928-86-6) was simultaneously deposited. Herein, the phosphorescent dopant was deposited in an amount of 7 wt % based on 100 wt % of the total amount of the light-emitting layer by adjusting a deposition rate.

On the light-emitting layer, a 50 Å-thick hole blocking layer was formed by depositing bis(2-methyl-8-quinolinolate)-4-(phenylphenolato)aluminum (BAlq) under the same vacuum deposition condition as above. Subsequently, a 200 Å-thick electron transport layer was formed by depositing Alq$_3$ under the same vacuum deposition condition as above. On the electron transport layer, LiF and Al were sequentially deposited as a cathode, manufacturing the organic photoelectric device.

A structure of the organic photoelectric device is ITO/NPB (80 nm)/EML (Compound 1 (93 wt %)+Ir(PPy)$_3$ (7 wt %), 30 nm)/BAlq (5 nm)/Alq$_3$ (20 nm)/LiF (1 nm)/Al (100 nm).

Examples 2 to 6

Organic light emitting diodes of Examples 2 to 6 were manufactured according to the same method as Example 1 by respectively using the compound shown in Table 2 as a host, instead of Compound 1 of Synthesis Example 9.

Comparative Example 1

An organic light emitting diode was manufactured according to the same method as Example 1 except for using CBP instead of Compound 1 of Synthesis Example 9.

Comparative Example 2

An organic light emitting diode was manufactured according to the same method as Example 1 except for using Compound Host 2 of Synthesis Example 2 instead of Compound 1 of Synthesis Example 9.

Comparative Example 3

An organic light emitting diode was manufactured according to the same method as Example 1 except for using Compound Host 3 of Synthesis Example 3 instead of Compound 1 of Synthesis Example 9.

Evaluation 2

Current density changes, luminance changes, and luminous efficiency depending on a voltage of each organic light emitting diode according to Examples 1 to 6 and Comparative Examples 1 to 3 were measured.

Specific measurement methods are as follows, and the results are shown in Table 2.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and, the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

TABLE 2

| No. | Compound | Driving voltage (V) | Color (EL color) | Efficiency (cd/A) |
|---|---|---|---|---|
| Example 1 | 1 | 3.57 | Green | 89.5 |
| Example 2 | 2 | 3.55 | Green | 89.2 |
| Example 3 | 6 | 3.54 | Green | 90.0 |
| Example 4 | 7 | 3.56 | Green | 89.0 |
| Example 5 | 25 | 3.49 | Green | 88.6 |
| Example 6 | 26 | 3.50 | Green | 88.9 |
| Comparative Example 1 | CBP | 4.80 | Green | 31.4 |
| Comparative Example 2 | Host 2 | 3.65 | Green | 79.8 |
| Comparative Example 3 | Host 3 | 4.25 | Green | 74.3 |

Referring to the results of Table 2, the devices of Example 1 to Example 6 realize a low driving voltage and high efficiency compared with the devices of Comparative Example 1 to Comparative Example 3.

Evaluation 3: Energy Level System Using Gaussian Tool

An energy level of each material was calculated by a B3LYP/6-31G** method using program Gaussian 09 with Super Computer GAIA (IBM power 6), and the results are shown in Table 3.

TABLE 3

| Compound | HOMO (eV) | LUMO (eV) |
|---|---|---|
| 1 | −5.85 | −1.92 |
| 2 | −5.61 | −1.95 |
| 6 | −5.86 | −1.95 |
| 7 | −5.82 | −1.93 |
| 25 | −5.63 | −2.04 |
| 26 | −5.60 | −2.01 |
| Host 1 | −5.94 | −1.94 |
| Host 2 | −5.73 | −1.85 |
| Host 3 | −5.76 | −1.82 |

Referring to the results of Table 3, Compounds 1, 2, 6, 7, 25, and 26 turned out to have a low LUMO energy level compared with Compound Hosts 2 and 3. Accordingly, Compounds may easily make movement of electrons and realize a device having a low driving voltage. In addition, when a fluorene group having fast mobility is introduced into the compound, the compound may realize a device having high efficiency as well as a low driving voltage.

Manufacture of Organic Light Emitting Diode

Example 7

A glass substrate coated with ITO (indium tin oxide) as a 1500 Å-thick thin film was washed with distilled water. After washed with distilled water, the glass substrate was ultrasonic wave-washed with a solvent such as isopropyl alcohol, acetone, methanol, and the like and dried, moved to a plasma cleaner, cleaned with oxygen plasma for 10 minutes, and moved to a vacuum depositor. This obtained ITO transparent electrode was used as an anode, N4,N4'-diphenyl-N4,N4'-bis(9-phenyl-9H-carbazol-3-yl)biphenyl-4,4'-diamine (Compound A) was vacuum-deposited on the ITO substrate to form a 700 Å-thick hole injection layer, 1,4,5,8,9,11-hexaazatriphenylene-hexacarbonitrile (HAT-CN) (Compound B) was deposited to be 50 Å thick on the injection layer, and N-(biphenyl-4-yl)-9,9-dimethyl-N-(4-(9-phenyl-9H-carbazol-3-yl)phenyl)-9H-fluoren-2-amine (Compound C) was deposited to be 1020 Å thick to form a hole transport layer. A 400 Å-thick light-emitting layer was formed on the hole transport layer by vacuum-depositing Compound 1 of Synthesis Example 9 and Compound B-1 simultaneously as a host and 10 wt % of tris(2-phenylpyridine)iridium [Ir(ppy)₃] as a dopant. Herein, Compound 1 and Compound B-1 were used at a 1:1 ratio. Subsequently, 8-(4-(4,6-di(naphthalen-2-yl)-1,3,5-triazin-2-yl)phenyl)quinolone (Compound D) and Liq were vacuum-deposited simultaneously at a 1:1 ratio on the light-emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

The organic light emitting diode had a five-layered organic thin layer, and specifically ITO/Compound A (700 Å)/Compound B (50 Å)/Compound C (1020 Å)/EML [Compound 1:Compound B-1:Ir(ppy)₃=X:X:10%] (400 Å)/Compound D:Liq (300 Å)/Liq (15 Å)/Al (1200 Å). (X=a weight ratio)

Examples 8 to 15

Organic light emitting diodes of Examples 8 to 15 were manufactured according to the same method as Example 7 by respectively using the compound shown in Table 4, instead of the two hosts of Example 7.

Comparative Example 5

An organic light emitting diode was manufactured according to the same method as Example 10 except for using Compound Host 1 of Comparative Synthesis Example 1 instead of Compound 1.

Evaluation 4

Luminous efficiency and life-span characteristics of each organic light emitting diode according to Examples 7 to 15 and Comparative Example 5 were measured.

Specific measurement methods are as follows, and the results are shown in Table 4.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and, the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm²) were calculated by using the luminance, current density, and voltages (V) from the items (1) and (2).

TABLE 4

| | First host | Second host | First host:Second host | Driving voltage (V) | Efficiency (cd/A) |
|---|---|---|---|---|---|
| Example 7 | Compound 1 | B-1 | 1:1 | 3.55 | 90.0 |
| Example 8 | Compound 1 | B-22 | 1:1 | 3.51 | 89.5 |
| Example 9 | Compound 1 | B-25 | 1:1 | 3.50 | 99.5 |
| Example 10 | Compound 1 | B-31 | 1:1 | 3.55 | 89.9 |
| Example 11 | Compound 2 | B-31 | 1:1 | 3.48 | 90.5 |
| Example 12 | Compound 6 | B-31 | 1:1 | 3.50 | 89.9 |
| Example 13 | compound 7 | B-31 | 1:1 | 3.55 | 89.5 |
| Example 14 | Compound 29 | B-31 | 1:1 | 3.53 | 90.0 |
| Example 15 | Compound 30 | B-31 | 1:1 | 3.52 | 92.1 |
| Comparative Example 5 | Host 1 | B-31 | 1:1 | 4.20 | 59.2 |

Referring to Table 4, the organic light emitting diodes according to Examples 7 to 15 lowered a driving voltage while maintaining luminous efficiency compared with the organic light emitting diode according to Comparative Example 5. The reason is that the compound of the present invention appropriately brings about a synergy effect of a triphenylene group directly linked with an ET group to obtain a low LUMO, more than one meta substituent to obtain appropriate film characteristics, and a fluorene group preventing crystallization and having high electron mobility.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS 100, 200: organic light emitting diode
105: organic layer
110: cathode
120: anode
130: light-emitting layer
140: hole auxiliary layer

What is claimed is:
1. A compound for an organic optoelectronic device, wherein the compound is selected from compounds of Group 1:

[Group 1]

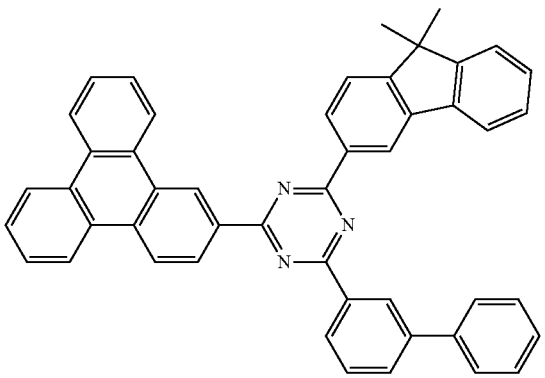

1

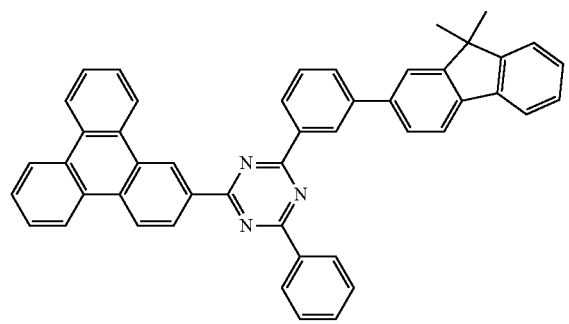
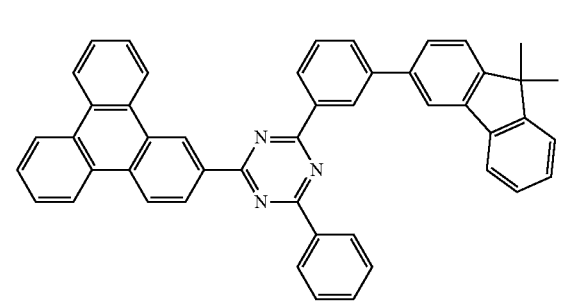
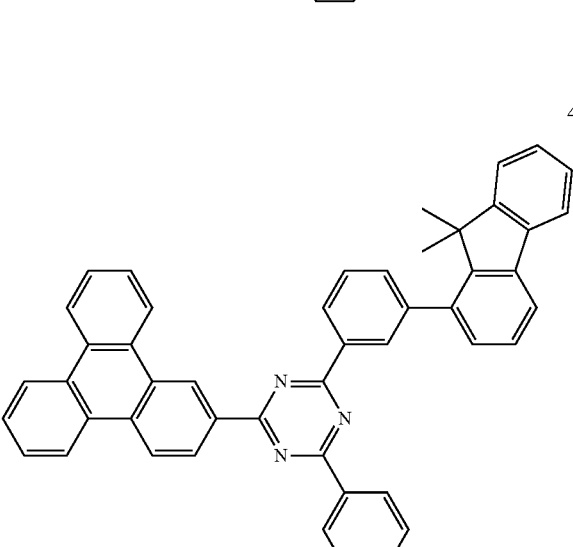
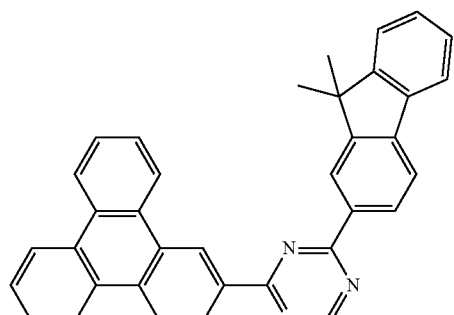

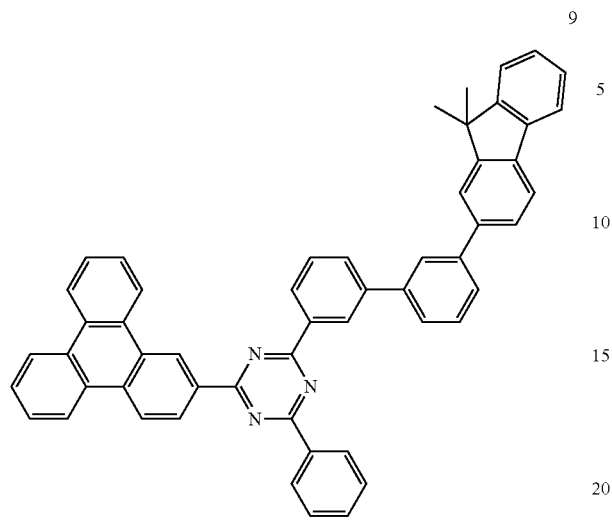
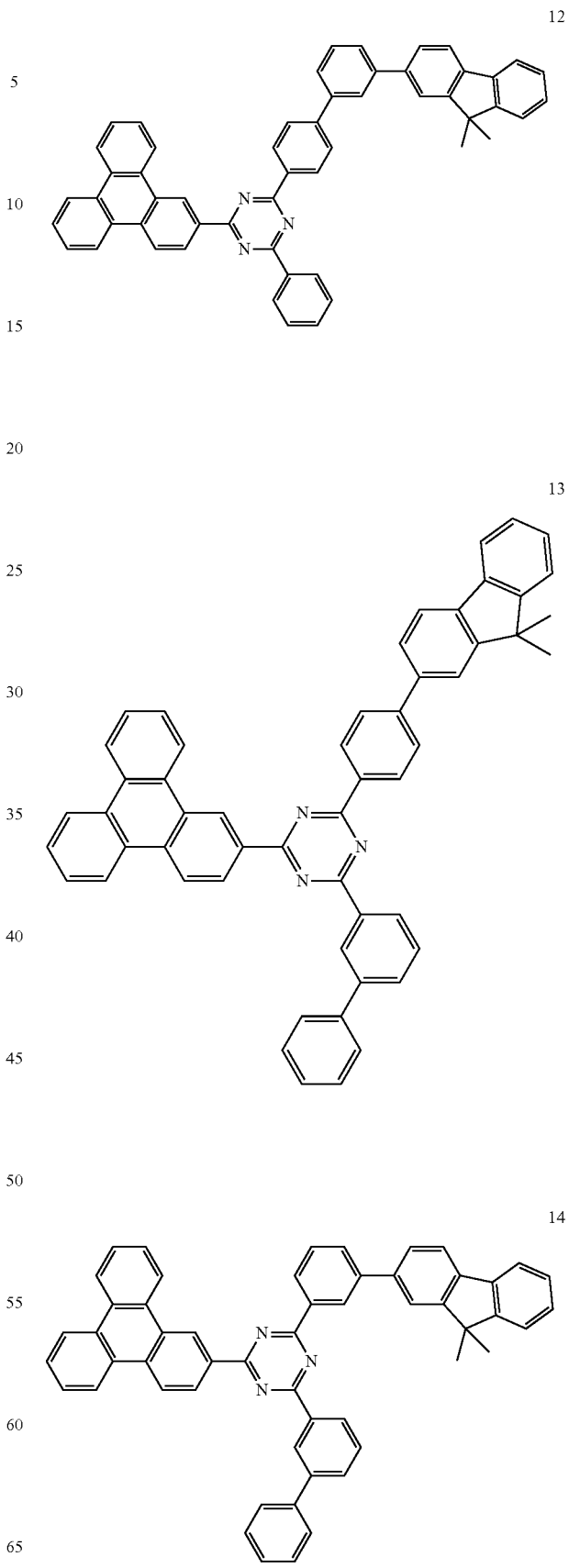

15
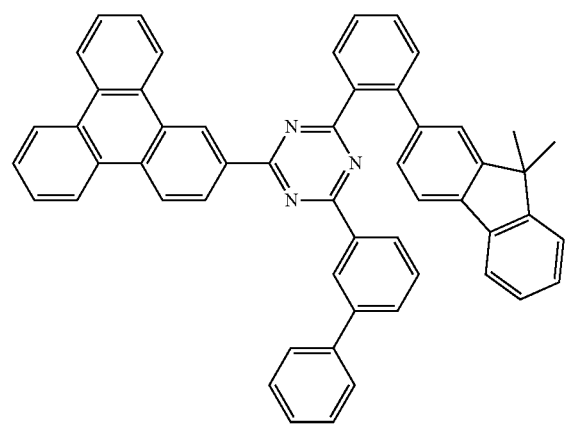
16
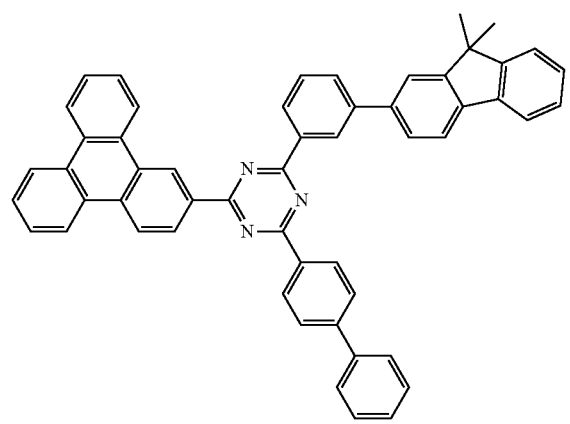
17
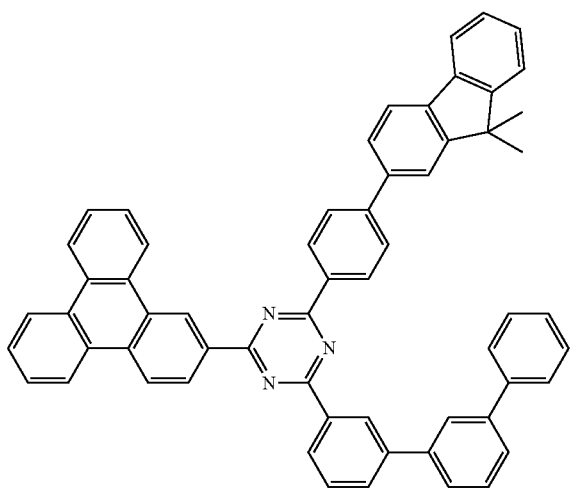
18
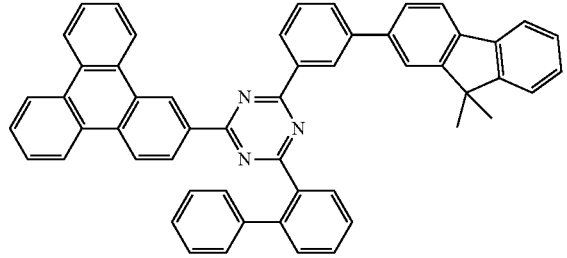
19
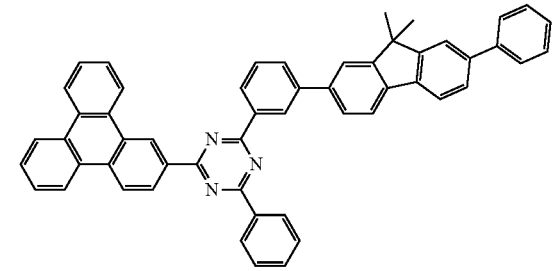
20
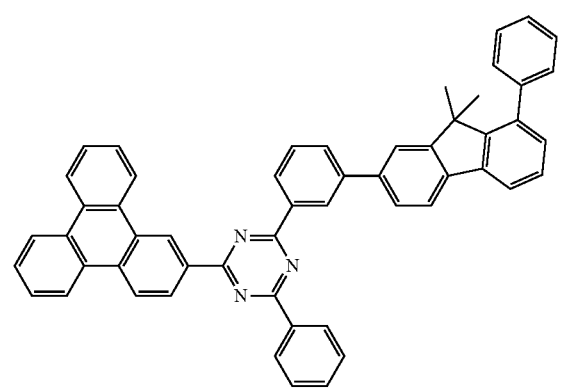
21
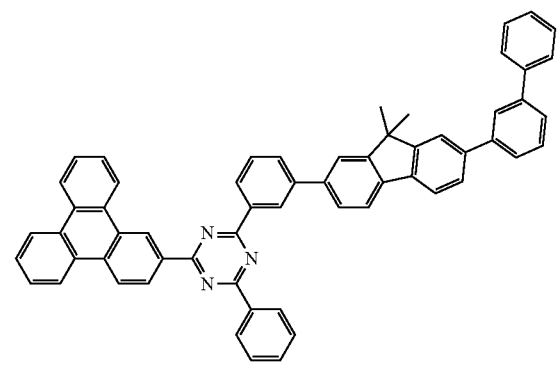

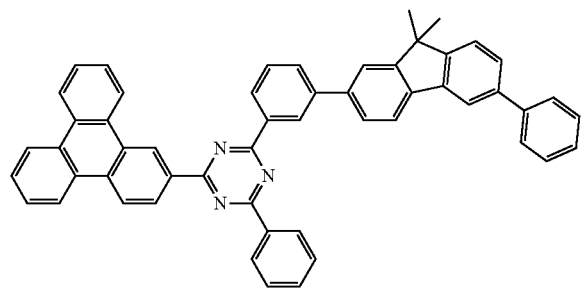
22
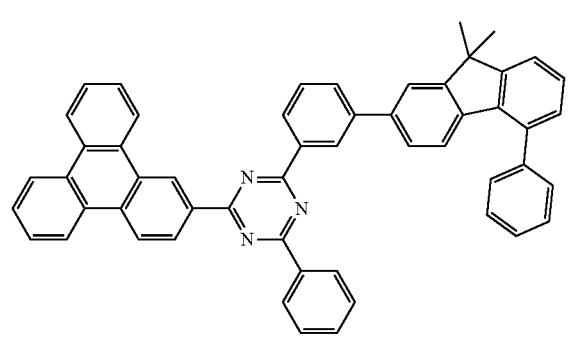
23
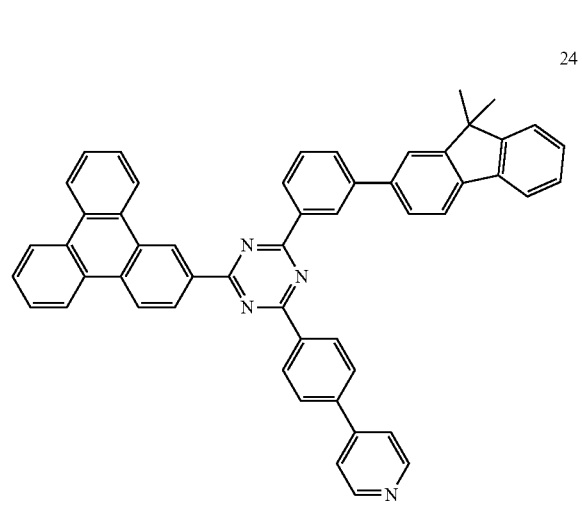
24
25
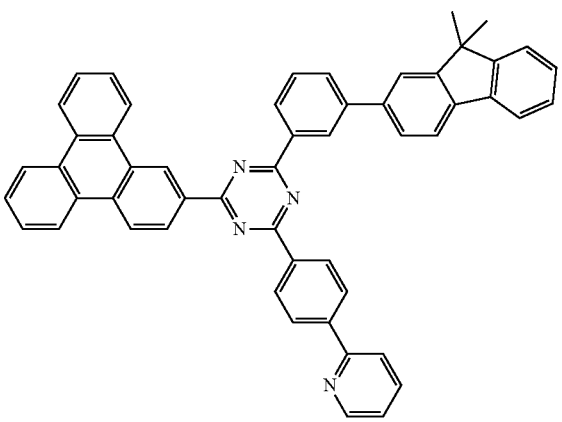
26

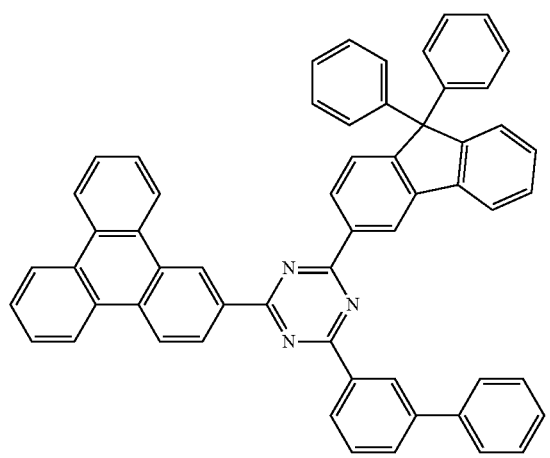
29
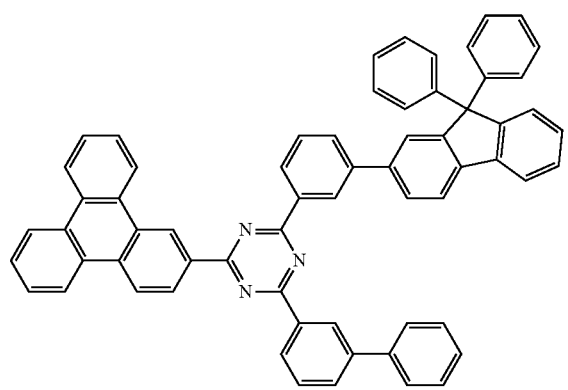
32
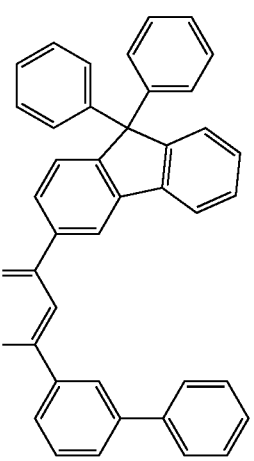
30
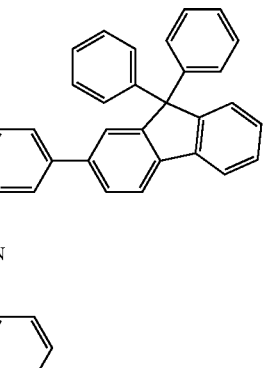
31
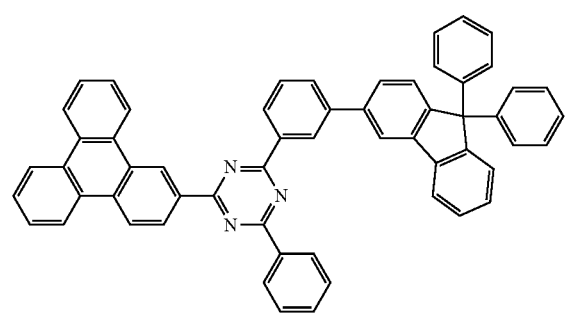
33
34
35

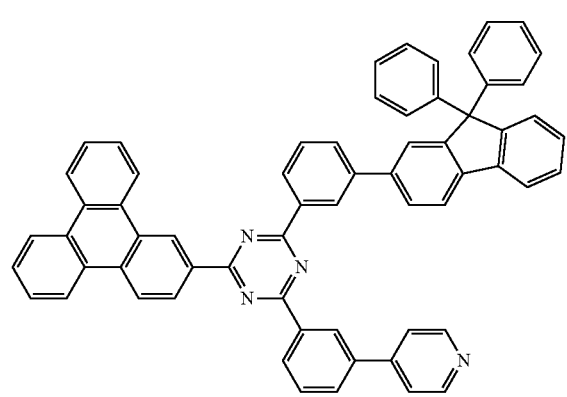
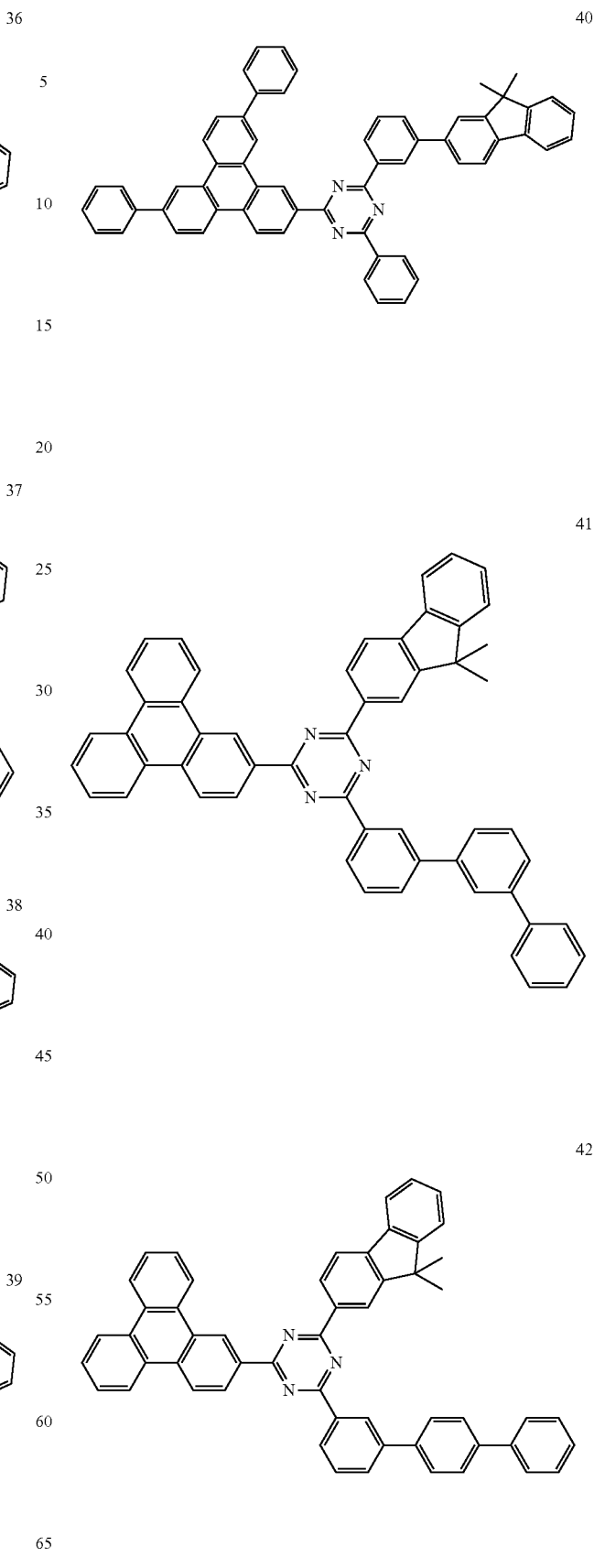

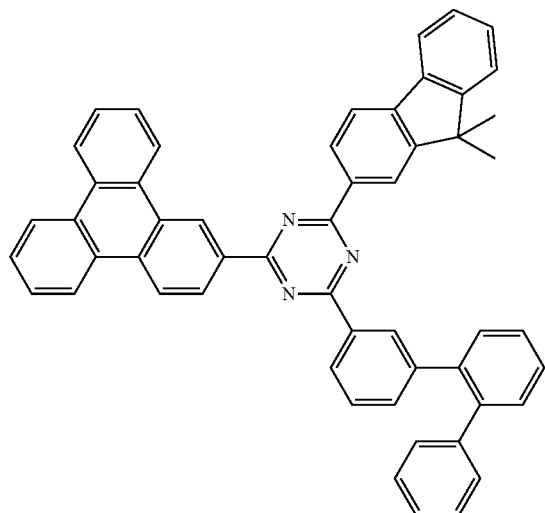
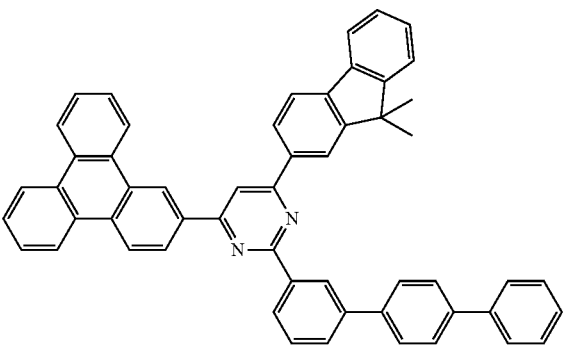
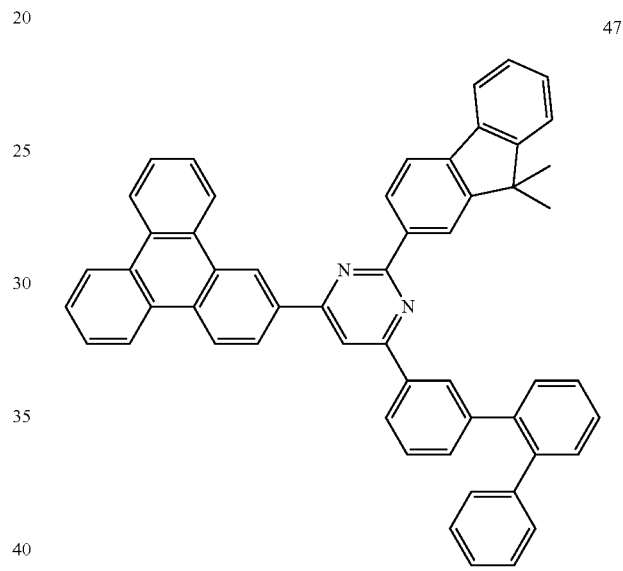
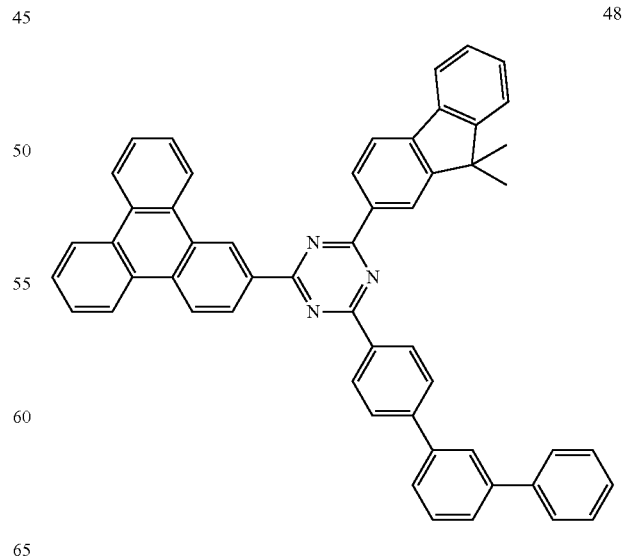

-continued

49
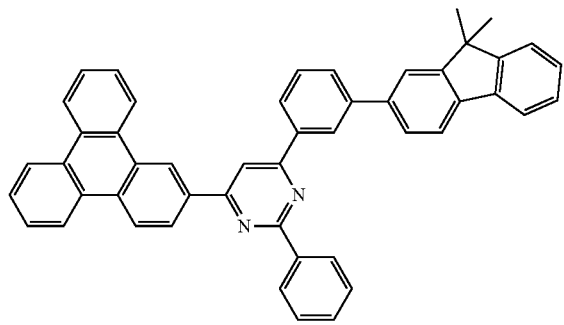

50
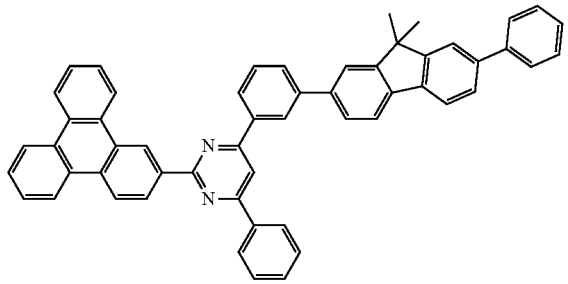

51
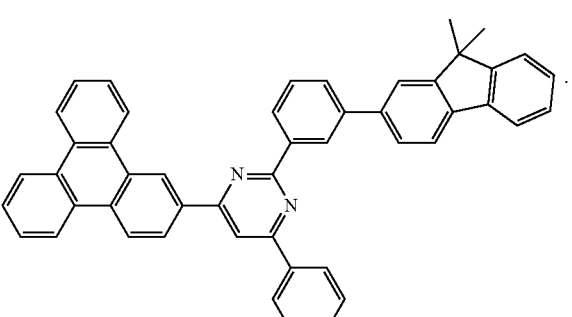

2. A composition for an organic optoelectronic device, comprising
the first compound for an organic optoelectronic device of claim 1; and
a second compound for an organic optoelectronic device represented by Chemical Formula 2:

[Chemical Formula 2]

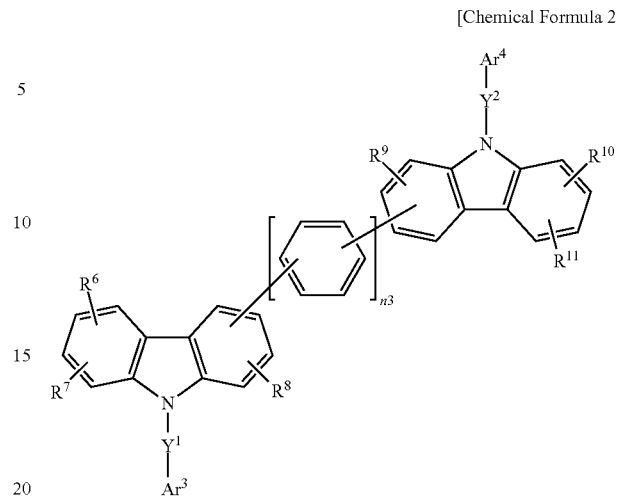

wherein, in Chemical Formula 2, $Y^1$ and $Y^2$ are independently a single bond, a substituted or unsubstituted C6 to C30 arylene group, a substituted or unsubstituted C2 to C30 heteroarylene group, or a combination thereof, $Ar^3$ and $Ar^4$ are independently a substituted or unsubstituted C6 to C30 aryl group, a substituted or unsubstituted C2 to C30 heterocyclic group, or a combination thereof, $R^6$ to $R^{11}$ are independently hydrogen, deuterium, a substituted or unsubstituted C1 to C20 alkyl group, a substituted or unsubstituted C6 to C30 aryl group, a substituted or unsubstituted C2 to C50 heterocyclic group, or a combination thereof, and n3 is an integer of 0 to 2;

wherein the "substituted" refers to replacement of at least one hydrogen by deuterium, a C1 to C4 alkyl group, a C6 to C18 aryl group, or a C2 to C18 heteroaryl group.

3. The composition for an organic optoelectronic device of claim 2, wherein $Ar^3$ and $Ar^4$ of Chemical Formula 2 are independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted pyridinyl group, a substituted or unsubstituted pyrimidinyl group, a substituted or unsubstituted quinazolyl group, a substituted or unsubstituted isoquinazolyl group, a substituted or unsubstituted dibenzothiophenyl group, a substituted or unsubstituted dibenzofuranyl group, a substituted or unsubstituted carbazolyl group, a substituted or unsubstituted fluorenyl group, or a combination thereof.

4. The composition for an organic optoelectronic device of claim 2, wherein Chemical Formula 2 has one of structures of Group III,

*—Y¹—Ar³ and *—Y²—Ar⁴ are one of substituents of Group IV:
[Group III]
C-1
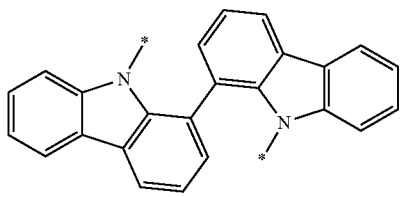
C-2
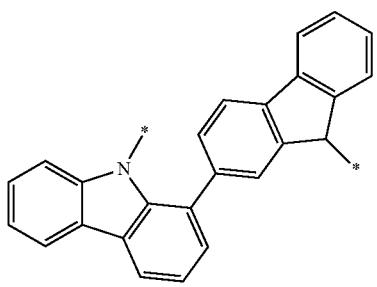
C-3
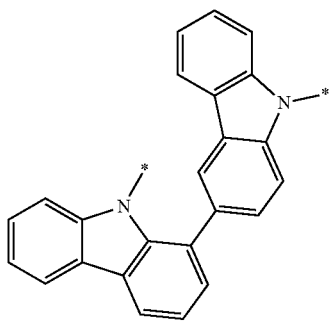
C-4
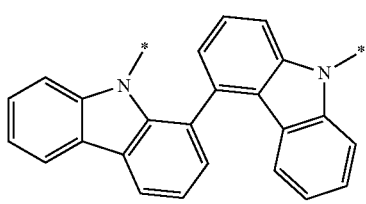
C-5
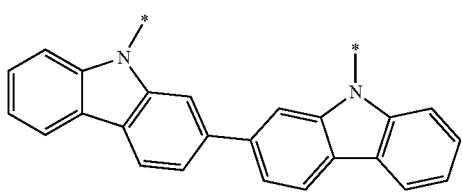
C-6
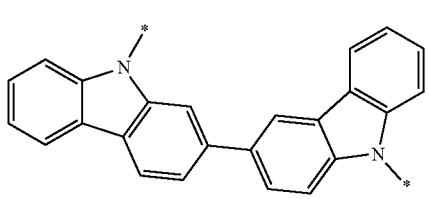
C-7
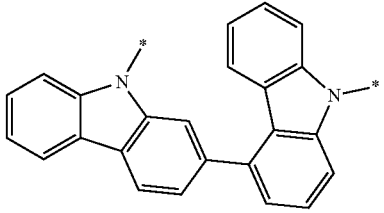
C-8
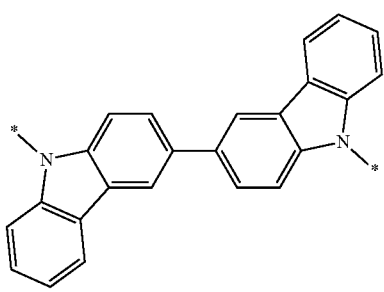
C-9
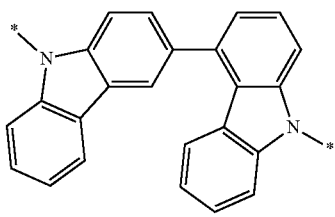
C-10
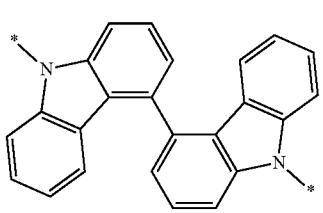
C-11
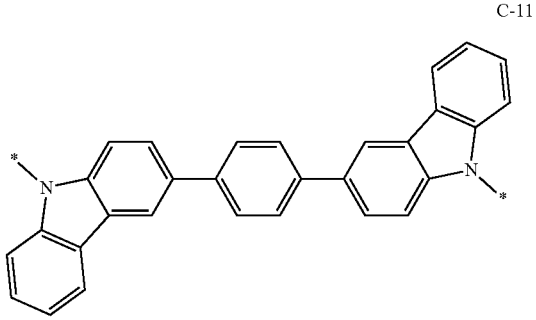
C-12
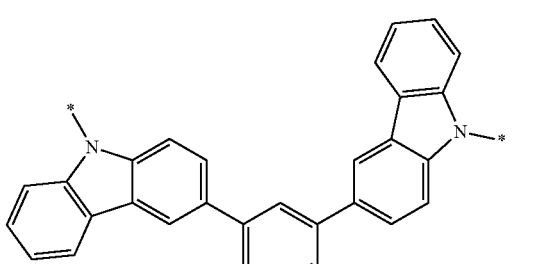

C-13
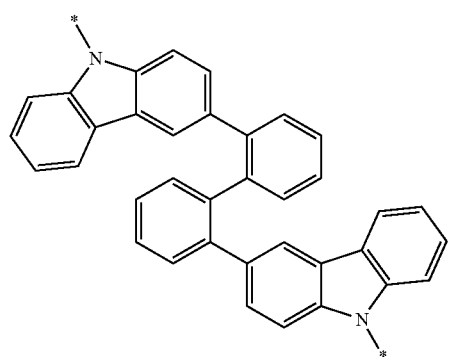
C-14
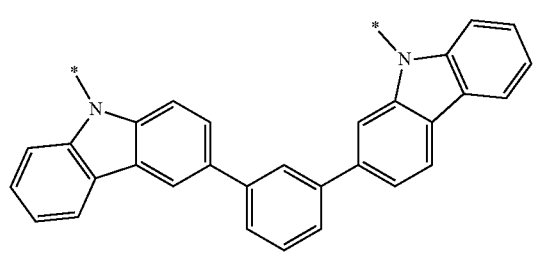
C-15
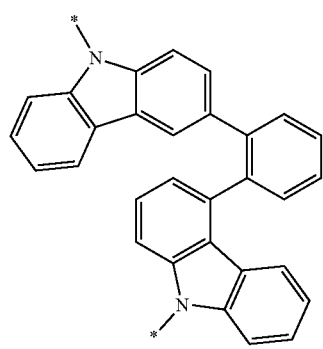
C-16
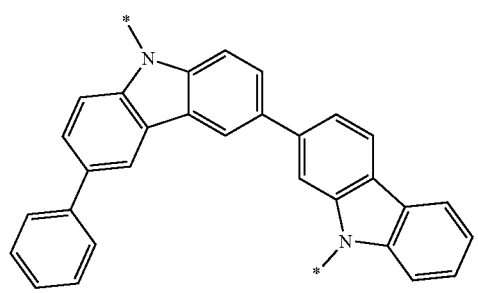
C-17
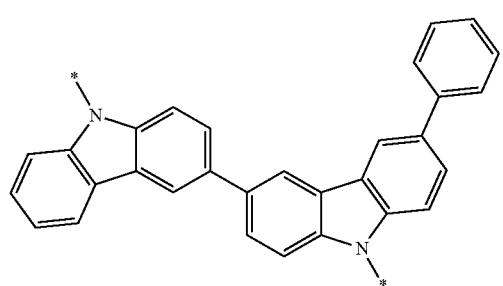
C-18
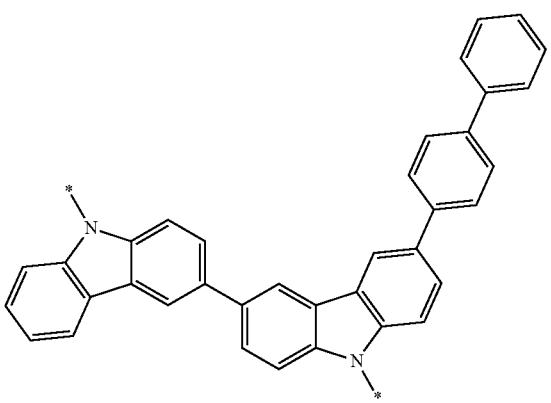
[Group IV]
B-1
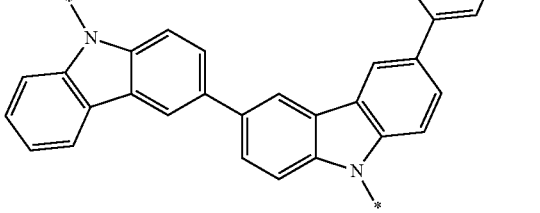
B-2
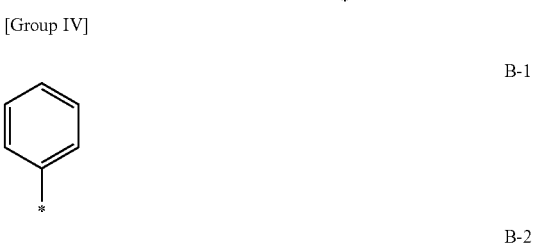
B-3
B-4
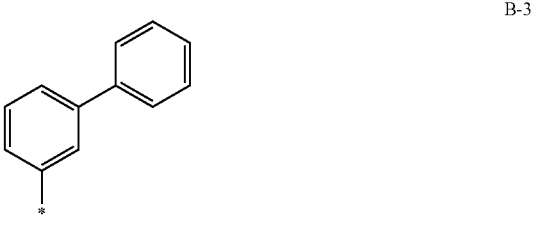
B-5
B-6
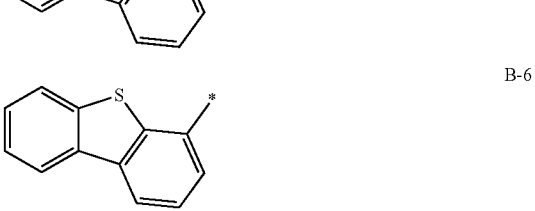

B-7 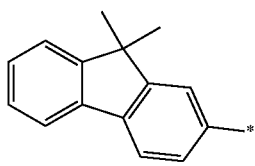
B-8 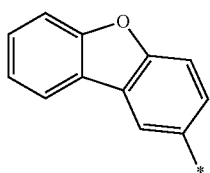
B-9 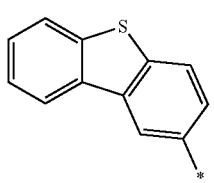
B-10 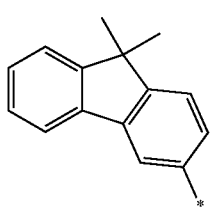
B-11 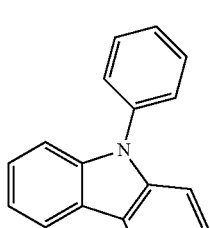
B-12 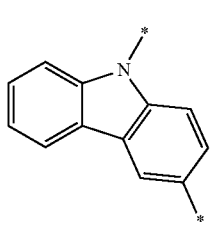
B-13 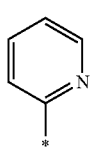
B-14 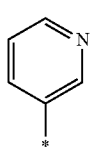
B-15 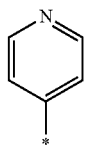
B-16 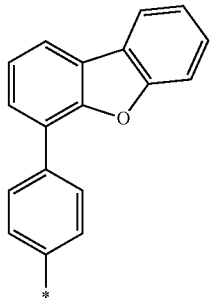
B-17 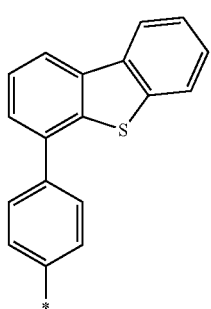
B-18 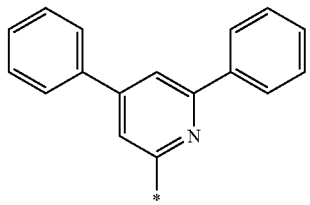
B-19 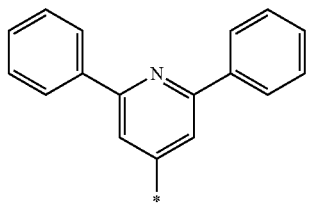
B-20 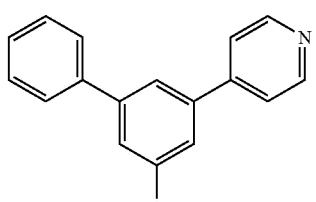
B-21 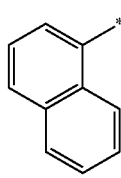

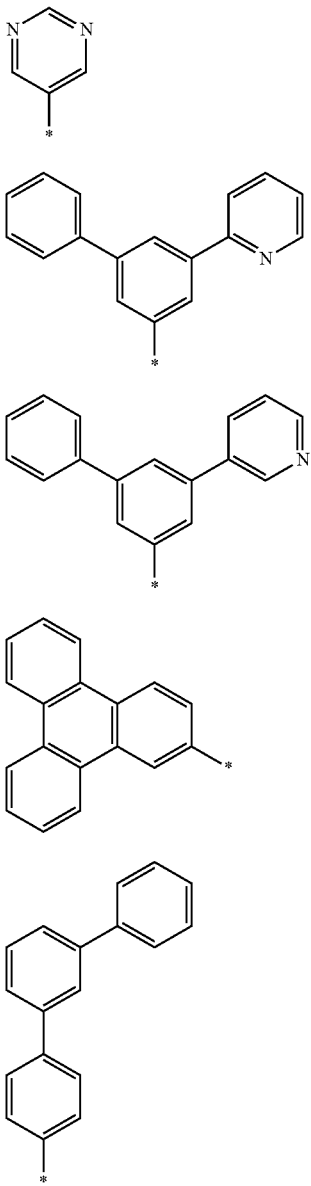

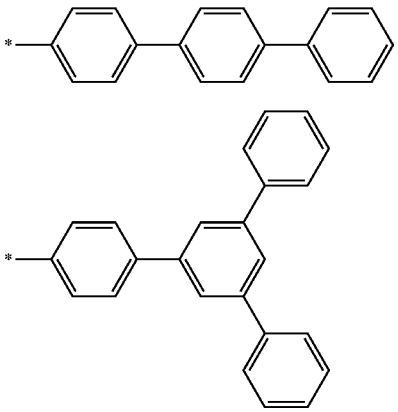

wherein, in Group III and Group IV, * is a linking point.

5. An organic optoelectronic device, comprising
an anode and a cathode facing each other, and
at least one organic layer disposed between the anode and the cathode,
wherein the organic layer includes the compound for an organic optoelectronic device of claim 1; or
the composition for an organic optoelectronic device of claim 2.

6. The organic optoelectronic device of claim 5, wherein the organic layer includes a light-emitting layer, and
the light-emitting layer includes the compound for an organic optoelectronic device or the composition for an organic optoelectronic device.

7. The organic optoelectronic device of claim 6, wherein the compound for an organic optoelectronic device or the composition for an organic optoelectronic device is included as a host of the light-emitting layer.

8. The organic optoelectronic device of claim 6, wherein the organic layer further includes an electron transport auxiliary layer that is adjacent to the light-emitting layer, and
the electron transport auxiliary layer includes the compound for an organic optoelectronic device; or the composition for an organic optoelectronic device.

9. A display device comprising the organic optoelectronic device of claim 5.

* * * * *